(12) United States Patent
Mazurek et al.

(10) Patent No.: US 9,546,141 B2
(45) Date of Patent: Jan. 17, 2017

(54) SALTS

(71) Applicant: Sprout Pharmaceuticals, Inc., Raleigh, NC (US)

(72) Inventors: Jaroslaw Mazurek, Rijswijk (NL); Mihaela Pop, Amsterdam (NL)

(73) Assignee: Sprout Pharmaceuticals, Inc., Raleigh, NC (US)

( * ) Notice: Subject to any disclaimer, the term of this patent is extended or adjusted under 35 U.S.C. 154(b) by 0 days.

(21) Appl. No.: 14/484,900

(22) Filed: Sep. 12, 2014

(65) Prior Publication Data

US 2015/0126524 A1    May 7, 2015

Related U.S. Application Data

(63) Continuation of application No. 13/131,926, filed as application No. PCT/EP2009/067007 on Dec. 14, 2009, now abandoned.

(30) Foreign Application Priority Data

Dec. 15, 2008 (EP) .................... 08171699

(51) Int. Cl.
| | | |
|---|---|---|
| *A61K 31/496* | (2006.01) | |
| *C07C 309/04* | (2006.01) | |
| *C07C 309/29* | (2006.01) | |
| *C07C 55/07* | (2006.01) | |
| *C07D 235/26* | (2006.01) | |
| *C07D 309/30* | (2006.01) | |
| *C07D 275/06* | (2006.01) | |
| *C07D 279/28* | (2006.01) | |
| *C07C 55/08* | (2006.01) | |
| *C07C 309/30* | (2006.01) | |

(52) U.S. Cl.
CPC ........... *C07D 235/26* (2013.01); *A61K 31/496* (2013.01); *C07C 55/07* (2013.01); *C07C 55/08* (2013.01); *C07C 309/04* (2013.01); *C07C 309/29* (2013.01); *C07C 309/30* (2013.01); *C07D 275/06* (2013.01); *C07D 279/28* (2013.01); *C07B 2200/13* (2013.01)

(58) Field of Classification Search
CPC ... A61K 31/496; C07C 309/04; C07C 309/29; C07C 55/07; C07C 55/08; C07B 2200/13; C07D 235/26; C07D 309/30; C07D 275/06; C07D 279/28
See application file for complete search history.

(56) References Cited

U.S. PATENT DOCUMENTS

| | | | |
|---|---|---|---|
| 3,472,854 A | 10/1969 | Archer | |
| 4,438,091 A | 3/1984 | Gruber et al. | |
| 4,954,503 A | 9/1990 | Strupezewski et al. | |
| 5,281,585 A | 1/1994 | Duggan et al. | |
| 5,407,686 A | 4/1995 | Patel et al. | |
| 5,482,948 A | 1/1996 | Soyka et al. | |
| 5,576,290 A | 11/1996 | Hadley | |
| 5,576,318 A | 11/1996 | Bietti et al. | |
| 5,883,094 A | 3/1999 | Fliri et al. | |
| 6,051,555 A | 4/2000 | Hadley | |
| 6,281,218 B1 | 8/2001 | Cereda et al. | |
| 6,627,646 B2 | 9/2003 | Bakale et al. | |
| 7,183,410 B2 | 2/2007 | Bombarda et al. | |
| 7,241,805 B2 | 7/2007 | Oberegger et al. | |
| 7,420,057 B2 | 9/2008 | Bombarda et al. | |
| 7,973,043 B2 | 7/2011 | Migaly | |
| 8,030,314 B2 | 10/2011 | Beck | |
| 8,545,886 B2 | 10/2013 | Eisenreich et al. | |
| 8,658,207 B2 | 2/2014 | Eisenreich et al. | |
| 8,722,682 B2 | 5/2014 | Volz et al. | |
| 8,785,458 B2 | 7/2014 | Ceci et al. | |
| 2002/0052370 A1 | 5/2002 | Barber et al. | |
| 2002/0091115 A1 | 7/2002 | Dyatkin et al. | |
| 2003/0055070 A1 | 3/2003 | Harrison et al. | |
| 2003/0083228 A1 | 5/2003 | Carpino et al. | |
| 2003/0104980 A1 | 6/2003 | Borsini et al. | |
| 2003/0119850 A1 | 6/2003 | Bombarda et al. | |
| 2004/0048877 A1 | 3/2004 | Friedl et al. | |
| 2004/0147581 A1 | 7/2004 | Taylor et al. | |
| 2004/0198706 A1 | 10/2004 | Carrara et al. | |
| 2005/0090550 A1 | 4/2005 | Barrett | |
| 2005/0159430 A1 | 7/2005 | Bombarda et al. | |
| 2006/0252773 A1 | 11/2006 | Ceci | |
| 2006/0258640 A1 | 11/2006 | Ceci et al. | |

(Continued)

FOREIGN PATENT DOCUMENTS

BE    904945 A1    12/1986
CA    2 515 426 C    1/2012

(Continued)

OTHER PUBLICATIONS

Borsini et al.,"Flibanserin:Antidepressant, 5-HT(1A) receptor agonist, 5-HT2 receptor antagonist", Jan. 1998 (Jan. 1998), Drugs of the Future 199801 ES, vol. 23, NR. 1, pp. 9-16. ISSN: 0377-8282.*
Berge, Stephen M., et al.; Pharmaceutical Salts; Journal of Pharmaceutical Sciences (1977) vol. 66, No. 1 pp. 1-19.
Borsini, F, et al; Flibanserin: Antidepressant, 5-HT(1A) Receptor Agonist 5-HT2 Receptor Antagonist; Drugs of the Future (1998) vol. 23, No. 1 pp. 9-16.
International Search Report and Written Opinion for PCT/EP2009/067007 mailed Nov. 3, 2010.
Kumar, Lokesh, et al; An Overview of Automated Systems Relevant in pharmaceutical Salt Screening; Drug Discovery Today (2007) vol. 12, No. 23-24 pp. 1046-1053.
Stahl, P. Heinrich, et al; Handbook of Pharmaceutical Salts: Properties, Selection, and Use; Verl. Helvetica Chimica Acta (2002) pp. 1-7.

(Continued)

*Primary Examiner* — Alexander R Pagano
*Assistant Examiner* — Ebenezer O Sackey
(74) *Attorney, Agent, or Firm* — Additon, Higgins & Pendleton, P.A.

(57) ABSTRACT

The present invention relates to new crystalline salt forms of flibanserine which have valuable pharmacological properties, to a process for their manufacture, to pharmaceutical formulations containing them and to their use as medicament.

8 Claims, 15 Drawing Sheets

(56) References Cited

U.S. PATENT DOCUMENTS

| | | |
|---|---|---|
| 2007/0032654 A1 | 2/2007 | Bombarda et al. |
| 2007/0032655 A1 | 2/2007 | Bombarda et al. |
| 2008/0038346 A1 | 2/2008 | Eisenreich et al. |
| 2008/0038347 A1 | 2/2008 | Eisenreich et al. |
| 2008/0069873 A1 | 3/2008 | Pearnchob et al. |
| 2008/0103155 A1 | 5/2008 | Mendla et al. |
| 2009/0054458 A1 | 2/2009 | Bombarda et al. |
| 2009/0318469 A1 | 12/2009 | Pyke |
| 2010/0093754 A1 | 4/2010 | Boeck |
| 2013/0172304 A1 | 7/2013 | Boeck |
| 2013/0203671 A1 | 8/2013 | Castro et al. |
| 2013/0203766 A1 | 8/2013 | Mendla et al. |

FOREIGN PATENT DOCUMENTS

| | | | |
|---|---|---|---|
| EP | 0200322 A1 | | 11/1986 |
| EP | 0 526 434 A1 | | 2/1993 |
| EP | 0 526 434 | * | 3/1993 |
| EP | 0547517 A1 | | 6/1993 |
| EP | 1 256 343 A1 | | 11/2002 |
| GB | 2023594 A | | 1/1980 |
| JP | 58134033 | | 8/1983 |
| WO | 98/19668 A1 | | 5/1998 |
| WO | 99/64002 A1 | | 12/1999 |
| WO | 00/64441 A2 | | 11/2000 |
| WO | 02/072586 A1 | | 9/2002 |
| WO | 02/074288 A2 | | 9/2002 |
| WO | 03/013539 A1 | | 2/2003 |
| WO | 03/014079 A1 | | 2/2003 |
| WO | 03/030869 A1 | | 4/2003 |
| WO | 2005/087207 A1 | | 9/2005 |
| WO | 2006/019715 A1 | | 2/2006 |
| WO | 2006/024471 A1 | | 3/2006 |
| WO | 2008/006838 A1 | | 1/2008 |
| WO | 2008/019996 A2 | | 2/2008 |
| WO | 2008/116890 A2 | | 10/2008 |

OTHER PUBLICATIONS

Office Action in commonly owned European Patent Application No. 06807537.3; dated Mar. 8, 2013, 3 pages.
Office Action in commonly owned Canadian Patent Application No. 2,649,938; dated May 7, 2013, 3 pages.
Office Action in commonly owned Canadian Patent Application No. 2,654,798; dated May 7, 2013, 2 pages.
Office Action in commonly owned Canadian Patent Application No. 2,672,957; dated Nov. 1, 2013, 2 pages.
Office Action in counterpart Canadian Patent Application No. 2,563,743; dated Aug. 8, 2012, 2 pages.
Office Action in commonly owned Canadian Patent Application No. 2,802,600; dated Nov. 28, 2013, 2 pages.
Office Action in commonly owned Canadian Patent Application No. 2,682,015; dated Aug. 26, 2014, 2 pages.
Office Action in commonly owned Canadian Patent Application No. 2,802,600; dated Sep. 25, 2014, 2 pages.
New Collegiate Dictionary, 1981, p. 311 (i.e. definition of the term "diagnosis" as provided).
Office Action in commonly owned Korean Patent Application No. 10-2013-7033147; dated Feb. 28, 2014, 7 pages.
Office Action in commonly owned Chinese Patent Application No. 201310074677.5; dated Mar. 24, 2014, 8 pages.
Dennerstein et al.; Hypoactive Sexual Desire Disorder in Menopausal Women: A Survey of Western European Women; Journal of Sexual Medicine 2006; No. 3, 11 pages.
Leiblum et al.; Hypoactive Sexual Desire Disorder in Postmenopausal Women: US Results from the Women's International Study of Health and Sexuality (WISHeS); Menopause: The Journal of The North American Menopause Society 2006; vol. 13, No. 1, 11 pages.
Simon et al.; Efficacy and Safety of Flibanserin in Postmenopausal Women with Hypoactive Sexual Desire Disorder: Results of the SNOWDROP Trial; Menopause: The Journal of The North American Menopause Society 2013; vol. 21, No. 6, 8 pages.
Office Action in commonly owned Canadian Patent Application No. 2,699,414; dated Oct. 30, 2014, 3 pages.
Crenshaw; The Sexual Aversion Syndrome; J. Sex Marital Ther.; 1985; vol. 11, Issue 4, abstract; 1 page.
Muir et al.; Dose Optimization of Intravenous Magnesium Sulfate After Acute Stroke; Stroke; May 1998; 29:918-923; 7 pages.
Khaled; Role of 5-HT Receptors in Treatment of Overactive Bladder; Drugs Today (Barc). Aug. 2003; 39 (8); 599-607 (abstract only); 2 pages.
Invernizzi; Flibanserin, a Potential Antidepressant Drug, Lowers 5-HT and Raises Dopamine and Noradrenaline in the Rat Prefrontal Cortex Dialysate: Role of 5-HT1A Receptors; British Journal of Pharmacology (2003) 39, 1281-1288; 8 pages.
Nitti; Duloxetine: A New Pharmacologic Therapy for Stress Urinary Incontinence; Reviews in Urology; 2004; vol. 6 (Suppl. 3): S48-S55; 8 pages.
Rezakhaniha; Efficacy of Desmopressin in Treatment of Nocturia in Elderly Men; J Res Med Sci.; Apr. 2011; 16 (4): 516-523; 8 pages.
Mayo Clinic: Overactive Bladder, 2015; http://www.mayoclinic.org/diseases-conditions/overactive-bladder/basics/prevention/con-2; 3 pages.
Urinary Incontinence—Prevention—NHS Choices, 2014, http://www.nhs.uk/Conditions/Incontinence-urinary/Pages/Prevention.aspx.
Borsini et al.; Flibanserin: Antidepressant, 5-HT(1A) Receptor Agonist 5-HT2 Receptor Antagonist; Drugs of the Future; (1998) vol. 23, No. 1; pp. 9-16; 8 pages.
Dow; Using Dow Excipients for Controlled Release of Drugs in Hydrophilic Matrix Systems, 2006; pp. 1-34,36 pages.
Rueter et al.; Electrophysiological Examination of the Effects of Sustained Flibanserin Administration on Serotonin Receptors in Rat Brain; British Journal of Pharmacology 1999; 126, 627-638; 12 pages.
Steiner M: "Recognitiion of premenstrual dysphoric disorder and its treatment" Lancet The, Lancet Limited. London, GB, vol. 356, No. 9236, Sep. 30, 2000 (Sep. 30, 2000), pp. 1126-1127.
Office Action in commonly owned Canadian Patent Application No. 2,682,015; dated Dec. 20, 2013, 3 pages.
International Search Report for PCT/US00/18217 mailed Oct. 26, 2000.
International Search Report for PCT/EP00/08891 mailed Jan. 30, 2001.
International Search Report for PCT/US05/24623 mailed Nov. 4, 2005.
International Search Report for PCT/EP02/08466 mailed Nov. 21, 2002.
International Search Report for PCT/EP02/11103 mailed Jan. 14, 2003.
International Search Report for PCT/EP03/02184 mailed Aug. 12, 2003.
International Search Report for PCT/EP03/05226 mailed Sep. 17, 2003.
Borsini et al.; Further Characterization of Potential Antidepressant Action of Flibanserin; Psychopharmacology; (2001) 159:64-69; 7 pages.
International Search Report for PCT/EP05/04081 mailed Oct. 11, 2005.
International Search Report for PCT/EP05/04086 mailed Oct. 11, 2005.
International Search Report for PCT/EP06/64825 mailed Nov. 17, 2006.
International Search Report for PCT/EP07/57064 mailed Nov. 6, 2007.
International Search Report for PCT/EP07/58301 mailed Jul. 24, 2008.
International Search Report for PCT/EP07/58302 mailed Jun. 4, 2008.
International Search Report for PCT/EP08/53592 mailed Jun. 4, 2009.
Office Action in counterpart Canadian Patent Application No. 2,563,743; dated Apr. 3, 2013, 2 pages.
Office Action in commonly owned Korean Patent Application No. 10-2008-7013699; dated Jun. 12, 2013, 10 pages.

(56) References Cited

OTHER PUBLICATIONS

Office Action in commonly owned Brazilian Patent Application No. PI0211601-4; dated Sep. 20, 2012 9 pages.
Gao et al., "Efficacy and Safety of Flibanserin in Women with Hypoactive Sexual Desire Disorder: A Systematic Review and Meta-Analysis", J Sex Med, 2015, vol. 12, pp. 2095-2104.
Robinson, et al., "First Pharmacological Therapy for Hypoactive Sexual Desire Disorder in Premenopausal Women: Flibanserin", Annals of Pharmacotherapy, 2016, vol. 50(2), pp. 125-132.
Jaspers et al., "Efficacy and Safety of Flibanserin for the Treatment of Hypoactive Sexual Desire Disorder in Nomen: A Systematic Review and Meta-analysis", Abstract downloaded at http://www.ncbi.nlm.nih.gov/pubmed/26927498 on May 19, 2016, pp. 1-2.
Borsini et al., Behavioral Effects of Flibanserin (BIMT 17), Sep. 1999, Biochemistry and Behavior, vol. 64, Issue 1, pp. 137-146.
CMU Pharmaceutical Polymorphism, CMU Seed Fund Project on Detection and Control of Pharmaceutical Polymorphism, http://andrew.cmu.edu/user/suter/polymorph.html, as downloaded Apr. 3, 2008, 2002, pp. 1-3.
Bechard et al., Film Coating: Effect of Titanium Dioxide Concentration and Film Thickness on the Photostability of Nifedipine, International Journal of Pharmaceutics, 87 (1992), pp. 133-139.
U.S. Pharmacopia #23, 1995, pp. 1843-1844.
Borsini et al., Pharmacology of Flibanserin, 2002, CNS Drug Reviews, vol. 8, No. 2, pp. 117-142, 26 pages.
Taavoni et al.; Psychogeriatrics, Hormone Replacement Therapy: Post-Menopausal Sex Life and Attitudes Towards Sex, 2005; 5:9-14, 6 pages.
Selective Serotonin Reuptake Inhibitors (SSRIs) Information; http://www.fda.gov/Drugs/DrugSafety/InformationbyDrugClass/ucm283587.htm as downloaded on Feb. 16, 2016; 2 pages.
Kurtel et al.; Journal of the American Society of Hypertension, Impaired Vasomotor Function Induced by the Combination of Hypertension and Hypercholesterolemia, 2013; 7(1) pp. 14-23,10 pages.
Menopause Practice: A Clinician's Guide 3rd edition (NAMS 2007), 7 pages.
Katz et al.; Journal of Sex and Marital Therapy, The Relationship between Worry, Sexual Aversion, and Low Sexual Desire, 1999, vol. 25, Issue 4, abstract, 9 pages.
Office Action in European Patent Office in EP 09709701.8 on Oct. 22, 2015.
Kibbe et al.; Hydroxypropyl Methylcellulose: Handbook of Pharmaceutical Excipients, 2000, 6 pages, XP-002376679.
Office Action in counterpart European Patent Application No. 09774901.4; dated Aug. 9, 2013, 4 pages.
Office Action in counterpart European Patent Application No. 07728833.0; dated Aug. 21, 2012, 5 pages.
Office Action in counterpart European Patent Application No. 06764270.2; dated Mar. 6, 2012, 4 pages.
Office Action in counterpart Australian Patent Application No. 2006311038; dated Aug. 25, 2011, 2pages.
Office Action in counterpart Australian Patent Application No. 2007247094; dated Aug. 30, 2011, 2 pages.
Office action in counterpart Brazilian Patent Application No. PI0311189-0; dated Jun. 26, 2012, 10 pages.
Office Action in counterpart European Patent Application No. 07787338.8; dated Jul. 6, 2012, 4 pages.
Office Action in commonly owned Brazilian Patent Application No. PI0213358-0; dated Jul. 24, 2015, 4 pages.
Sexual and Gender Identity Disorders, Diagnostic and Statistical Manual of Mental Disorders, Fourth Edition Text Revision, American Psychiatric Association, 2000, 34 pages, 535-566.
Katz et al.; Efficacy of Flibanserin in Women with Hypoactive Sexual Desire Disorder: Results from the Begonia Trial; J Sex Med 2013, 10, 9 pages 1807-1815.
Singhal et al., Drug Polymorphism and Dosage Form Design: A Practical Perspective, Advanced Drug Delivery Reviews, 2004, 56 pages 335-347.
Otsuka et al., Effect of Polymorphic Forms of Bulk Powders on Pharmaceutical Properties of Carbamazepine Granules, Chem. Pharm. Bull., 1999, 47(6) pp. 852-856.
Gould, Salt selection for basic drugs, International Journal of Pharmaceutics vol. 33, Issues 1-3, Nov. 1986, pp. 201-217.
Giron et al.: "Thermal analysis and calorimetric methods in the characterization of polymorphs and solvates" Thermochimica Acta, Elsevier Science Publishers, Amsterdam, NL, vol. 248, 1995, pp. 1-59.
Thrombolytic Therapy: MedlinePlus Medical Encyclopedia, http://www.nim.nih.gov/medlineplus/ency/article/007089.htm, accessed Sep. 17, 2015, pp. 1-5.
Byrn, et al., Solid State Chemistry of Drugs, 1999, Chapter 11: "Hydrates and Solvates," pp. 233-247.
Walsh et al.; Sexual Dysfunction in the Older Woman, An Overview of the Current Understanding and Management; Drugs Aging 2004; 21 (10); pp. 656-675.
International Search Report for PCT/IB04/02286 mailed Sep. 24, 2004.
Semkova et al., Neuroprotective effect of 5-HT1A receptor agonist, Bay x 3702, demonstrated in vitro and in vivo, 1998, European Journal of Pharmacology, vol. 359, pp. 251-260.
Office Action in commonly owned Brazilian Patent Application No. 122012029907-3; dated Mar. 24, 2015, 11 pages.
Elger et al., Oedema reduction by levemopamil in focal cerebral ischemia of spontaneously hypertensive rats studied by magnetic resonance imaging, 1994, European Journal of Pharmacology, vol. 254, pp. 65-71.
Borsini et al., BIMT 17: a putative antidepressant with a fast onset of action?, 1997, Psychopharmacology, vol. 134, pp. 378-386.
Office Action in counterpart Canadian Patent Application No. 2,617,546; dated Mar. 25, 2013, 2 pages.
Vippagunta, et al., Advanced Drug Delivery Reviews, 2001; 48:3-26.
Office Action in counterpart Canadian Patent Application No. 2,626,134; dated Aug. 24, 2012, 2 pages.
Office Action in counterpart Canadian Patent Application No. 2,626,797; dated Aug. 21, 2012, 3 pages.
Poster, presented Nov. 6, 2009 at Sexual Medicine Society of North American 2009 Fall Scientific Meeting, 3 pages.
Transcript of Poster, presented Nov. 6, 2009 at Sexual Medicine Society of North American 2009 Fall Scientific Meeting, "Pooled Clinical Trial Analysis of Flibanserin Safety and Tolerability in Premenopausal Women with Hypoactive Sexual Desire Disorder", 7 pages.
Office Action in commonly owned Canadian Patent Application No. 2,649,938; dated Jan. 10, 2014, 3 pages.
Office Action in commonly owned Canadian Patent Application No. 2,654,798; dated Jan. 23, 2014, 2 pages.
Office Action in commonly owned Canadian Patent Application No. 2,617,546; dated Jul. 26, 2012, 2 pages.
Borsini F et al.: "BIMT 17, A 5-HT2A Receptor Antagonist and 5-HT1A Receptor Full Agonist in Rat Cerebral Cortex" Naunyn-Schmiedeberg's Archives of Pharmacology, Springer, Berlin, DE, vol. 352, No. 3, Sep. 1995 (Sep. 1995), 7 pages 276-282.
Office Action in commonly owned Japanese Patent Application No. 2005-530787; dated Jun. 30, 2014, 2 pages.
Office Action in commonly owned European Patent Application No. 07728833.0; dated Apr. 9, 2013, 1 page.
Office Action in commonly owned Korean Patent Application No. 10-2008-7013699; dated Mar. 21, 2014, 5 pages.
Office Action in commonly owned Brazilian Patent Application No. PI0211601-4; dated Feb. 27, 2012 8 pages.
Office Action in commonly owned Chinese Patent Application No. 201310074677.5; dated Dec. 5, 2014, 8 pages.

\* cited by examiner

Figure 1.1a X-ray powder diffraction diagram of HCl1 = chloride, form I
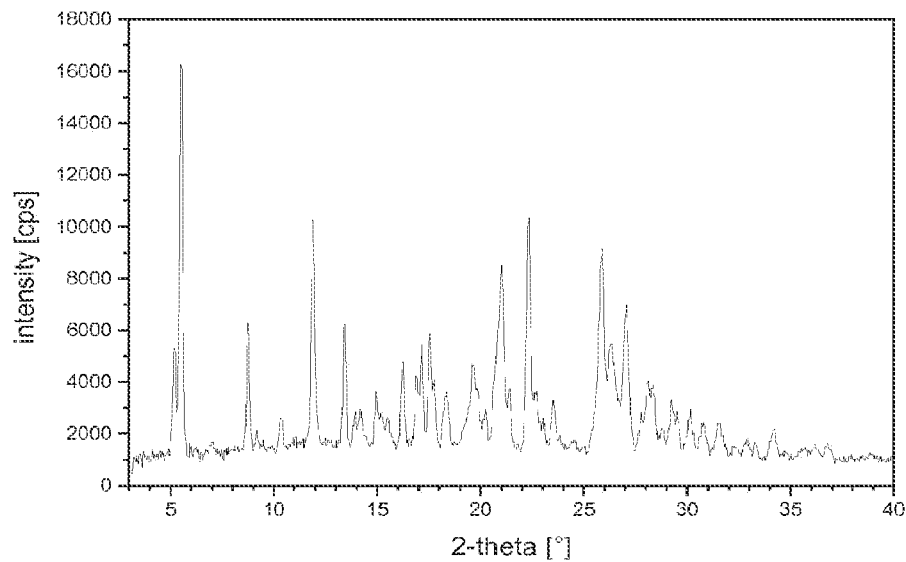
Figure 1.1b X-ray powder diffraction diagram of HCl3 = chloride, form III
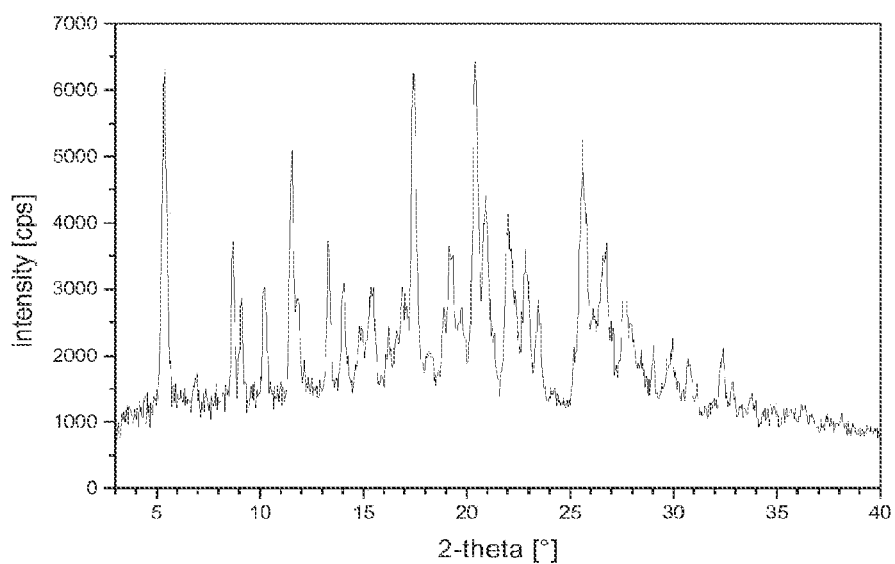

Figure 1.2a X-ray powder diffraction diagram of HBr1 = hydrobromid, form I
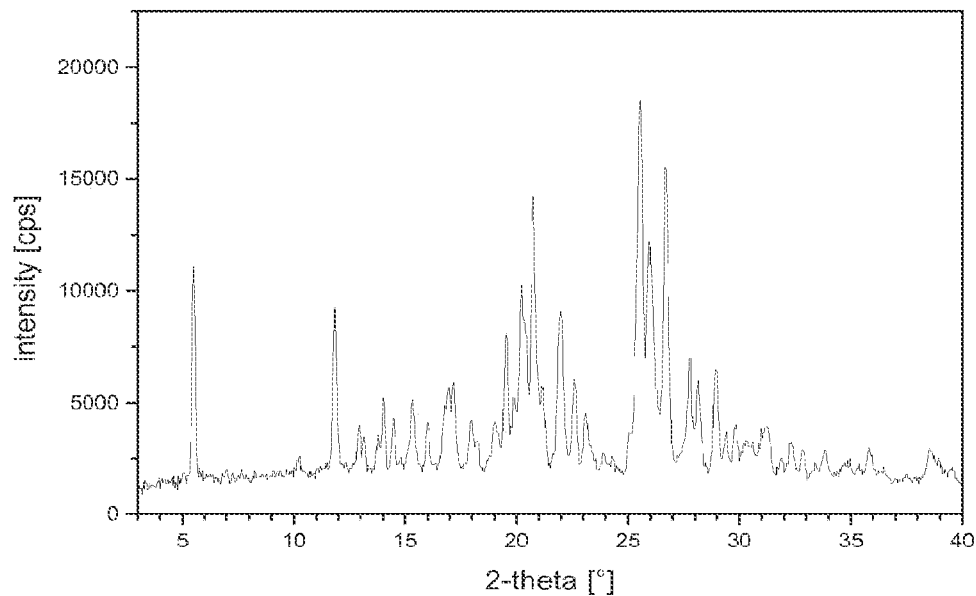
Figure 1.2b X-ray powder diffraction diagram of HBr3 = hydrobromid, form III
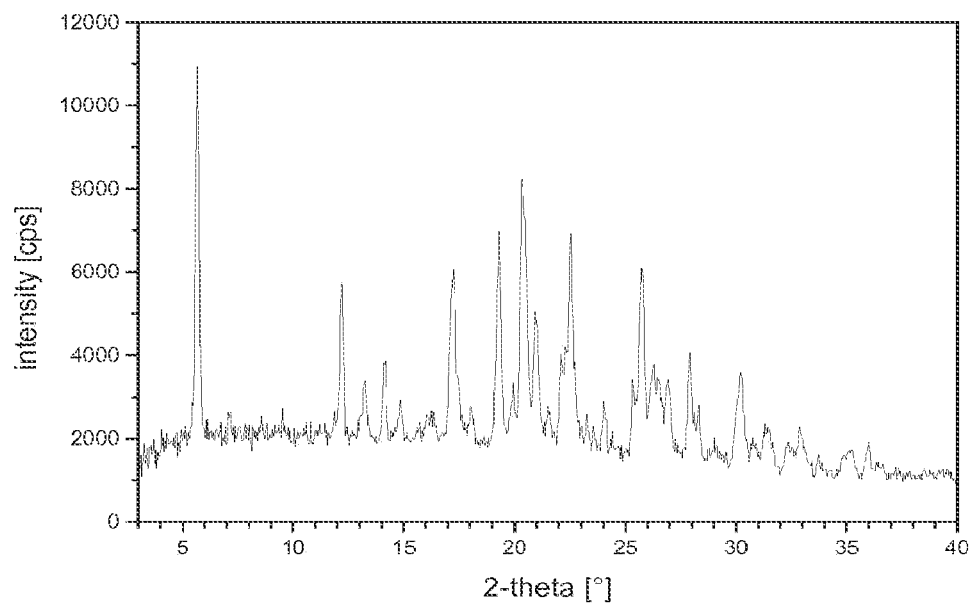

Figure 1.3 X-ray powder diffraction diagram of Eds1 = edisylate, form I
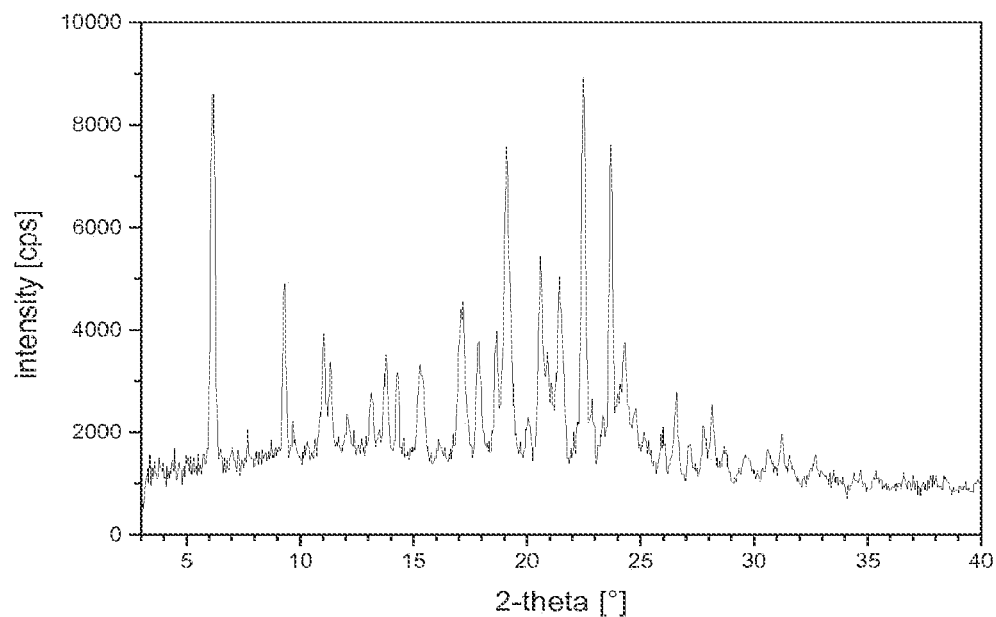
Figure 1.4 X-ray powder diffraction diagram of Tos1 = tosylate, form I
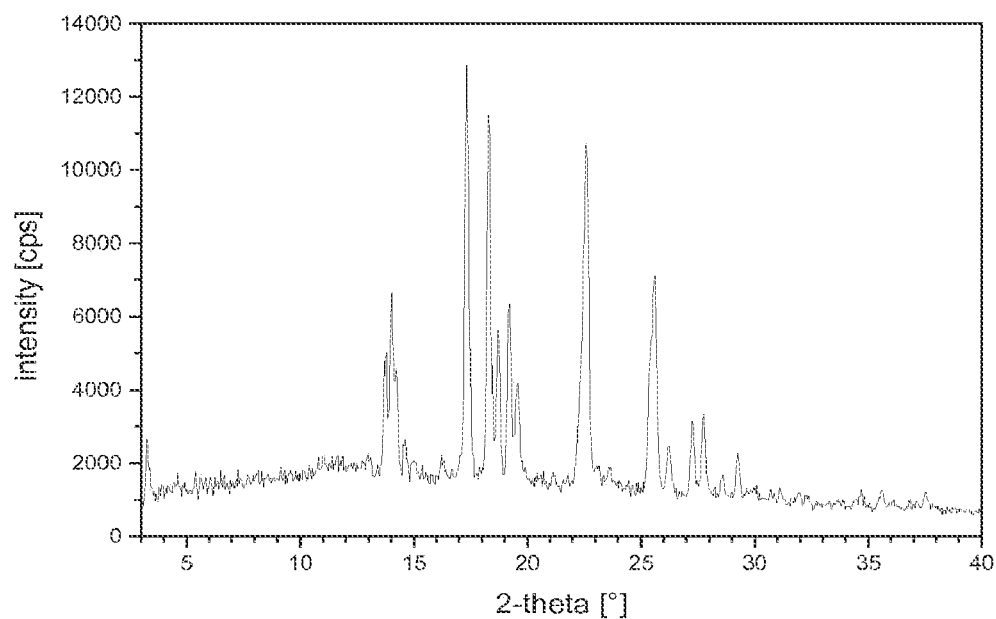

Figure 1.5 X-ray powder diffraction diagram of Mes1 = mesylate, form I
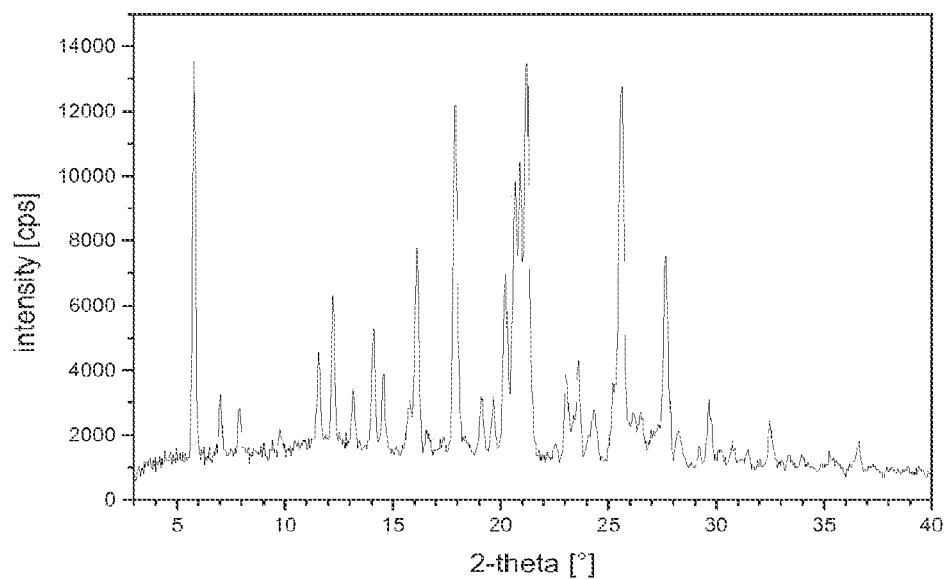
Figure 1.6 X-ray powder diffraction diagram of Bes1 = besylate, form I
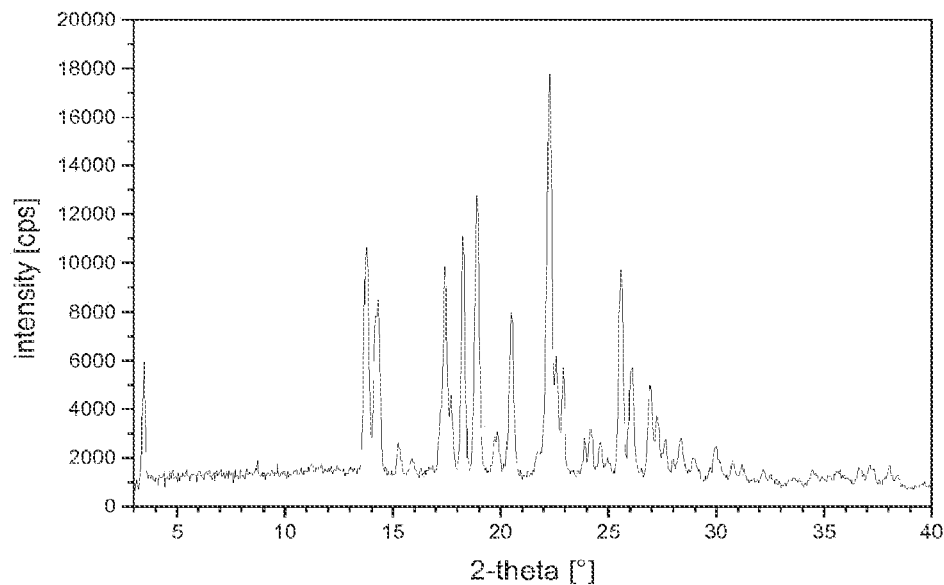

Figure 1.7a X-ray powder diffraction diagram of Oxa 1 = oxalate, form I
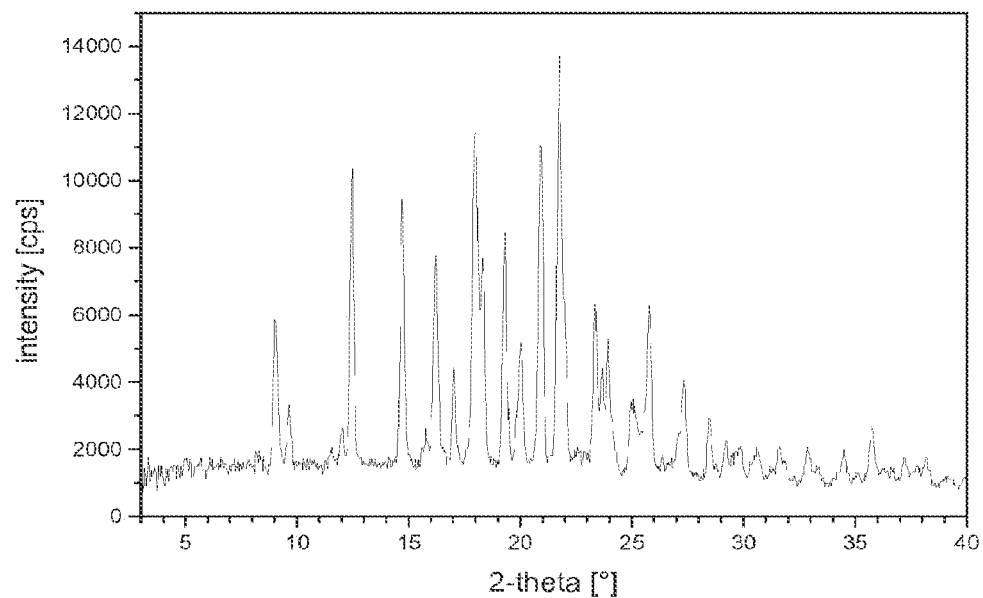
Figure 1.7b X-ray powder diffraction diagram of Oxa 5 = oxalate, form V
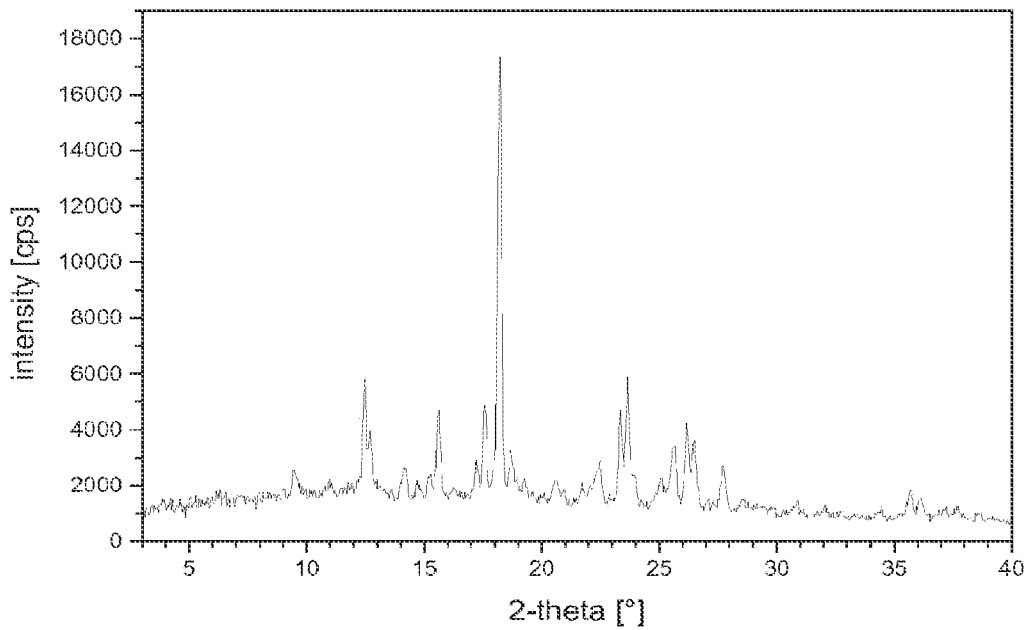

Figure 1.8 X-ray powder diffraction diagram of Sac 1 = sacharinate, form I
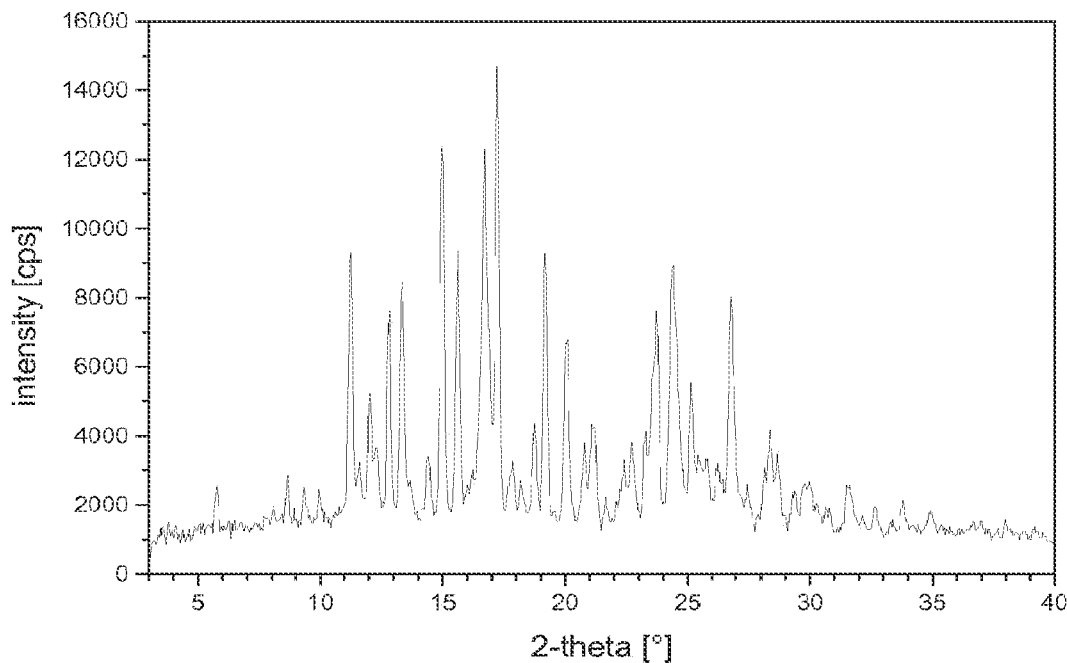
Figure 1.9 X-ray powder diffraction diagram of Pho1 = phosphate, form I
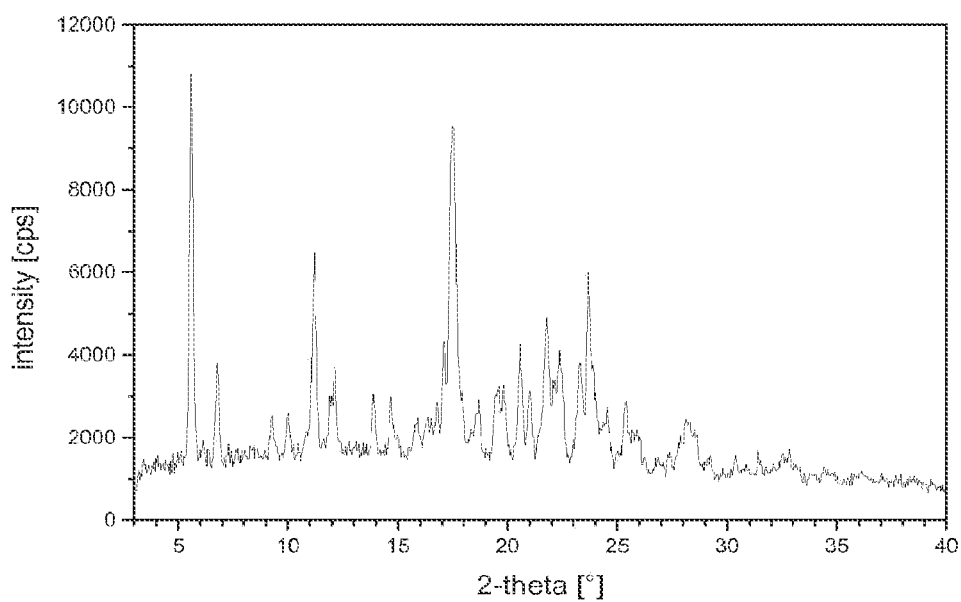

Figure 1.10a: X-ray powder diffraction diagram of Mae 1 = maleate, form I
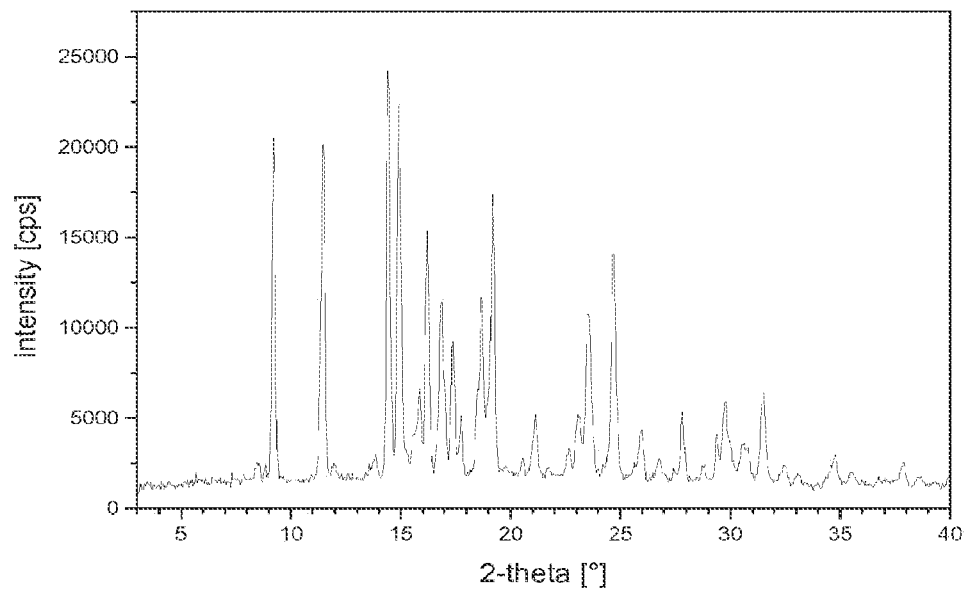
Figure 1.10b: X-ray powder diffraction diagram of Mae 3 = maleate, form III
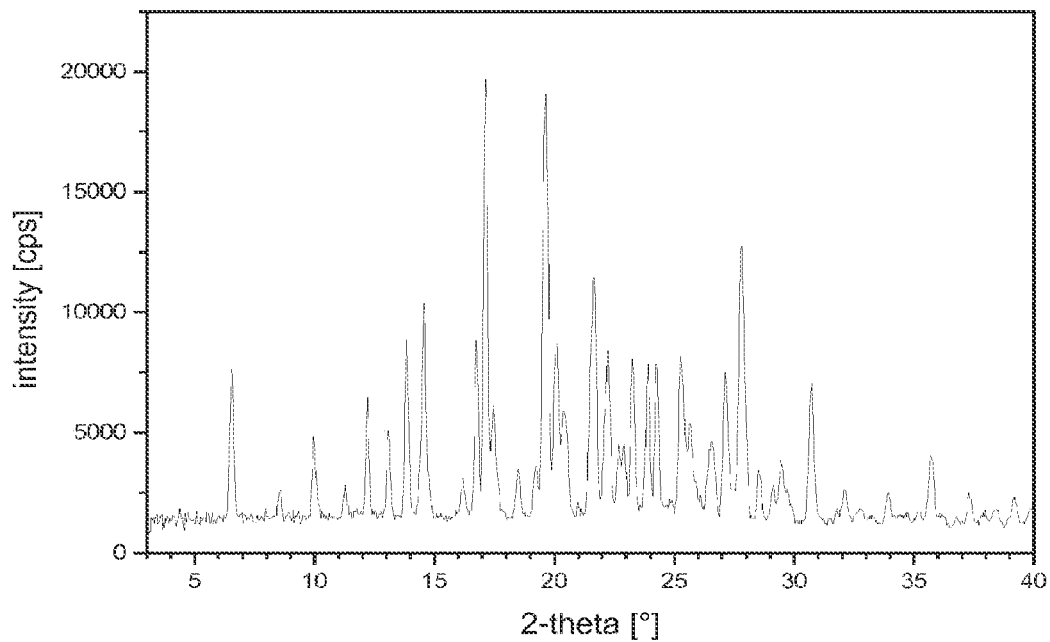

Figure 1.11: X-ray powder diffraction diagram of Ets 1 = ethanesulfonate, form I
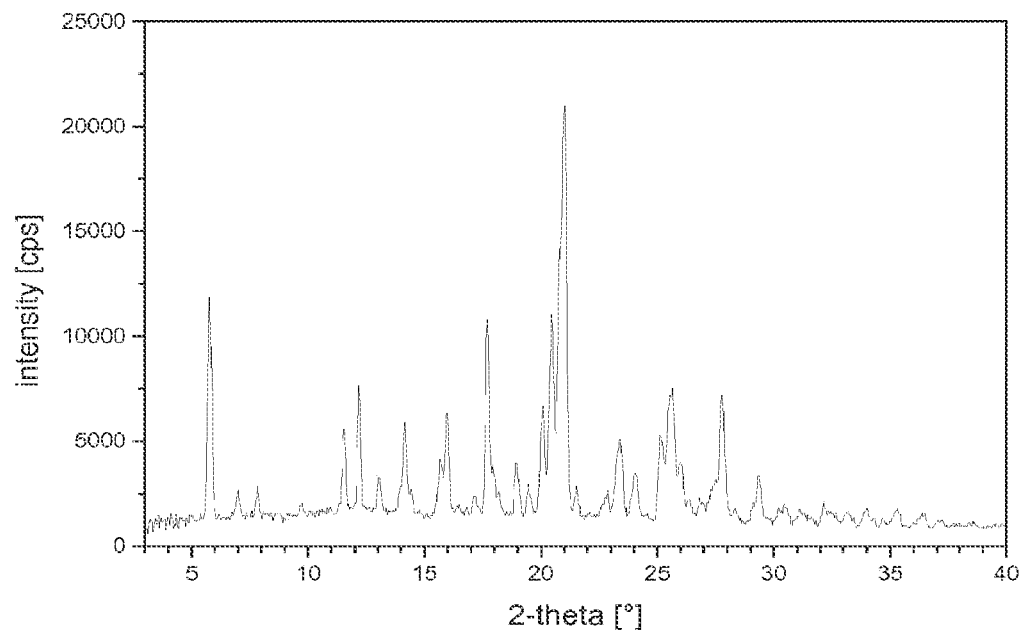
Figure 1.12 X-ray powder diffraction diagram of Cas1 = camphorsulfonate, form I
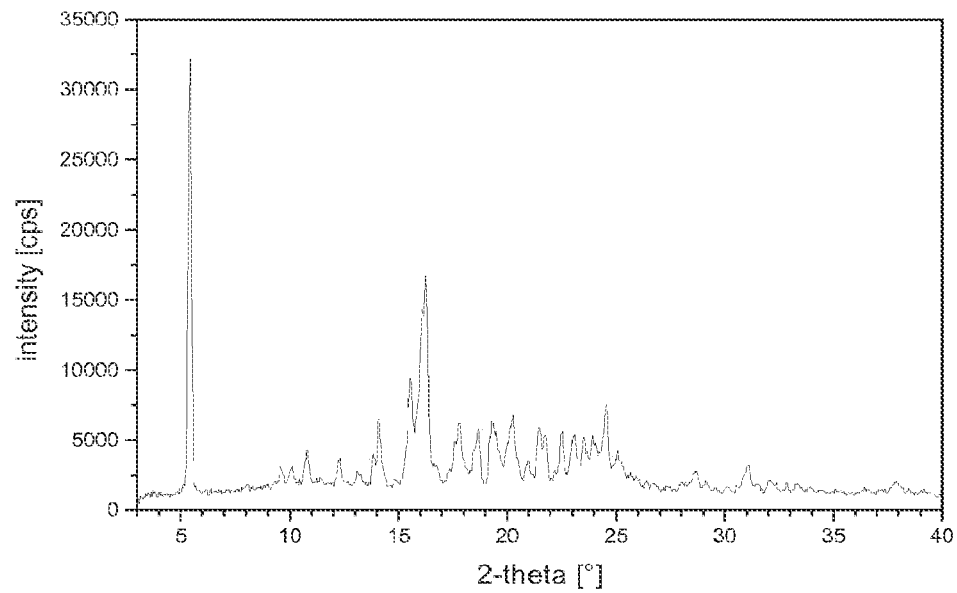

Figure 1.13: X-ray powder diffraction diagram of Mao 1 = malonate, form I
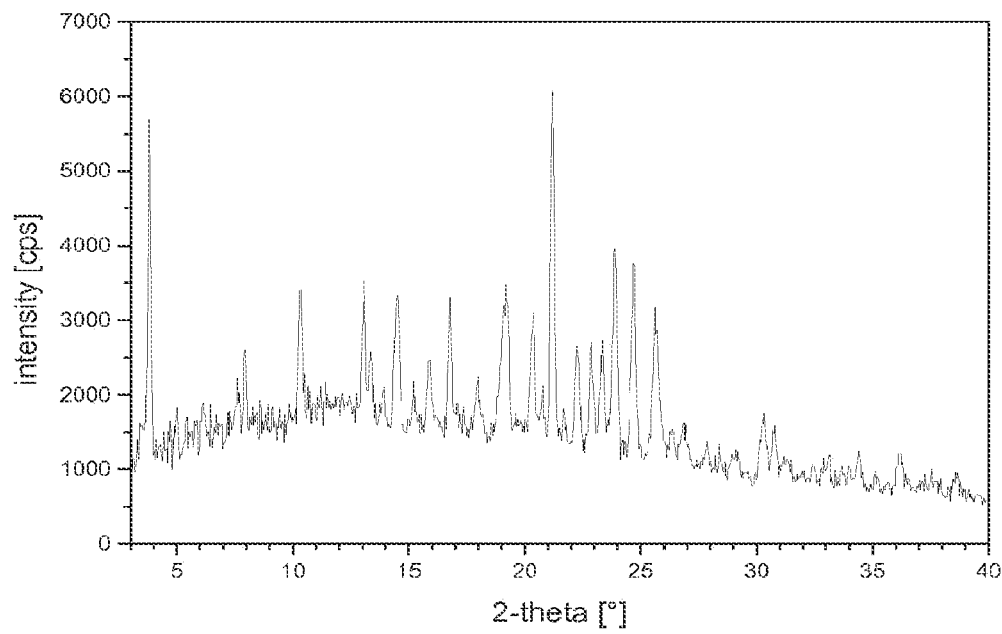
Figure 1.14: X-ray powder diffraction diagram of L-Tar 1 = L-tartrate, form I
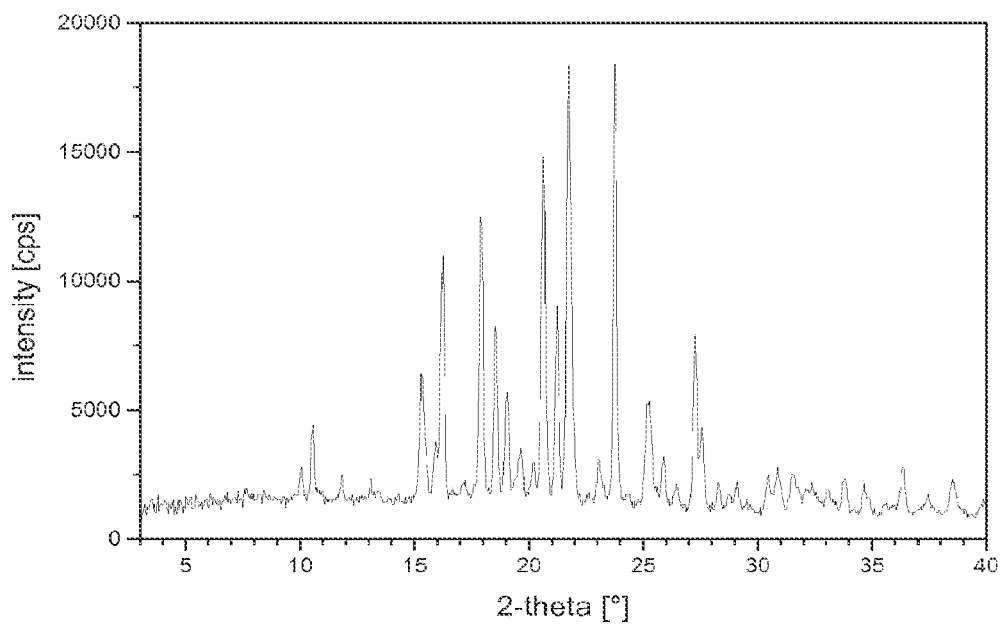

Figure 1.15a: X-ray powder diffraction diagram of Fum 1 = fumarate, form I
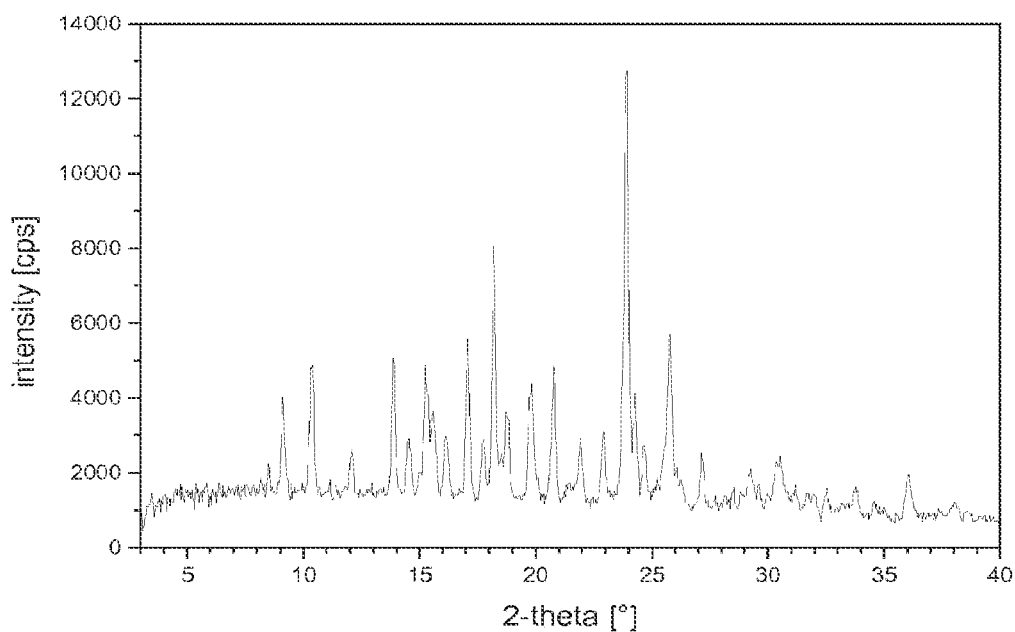
Figure 1.15b: X-ray powder diffraction diagram of Fum 2 = fumarate, form II
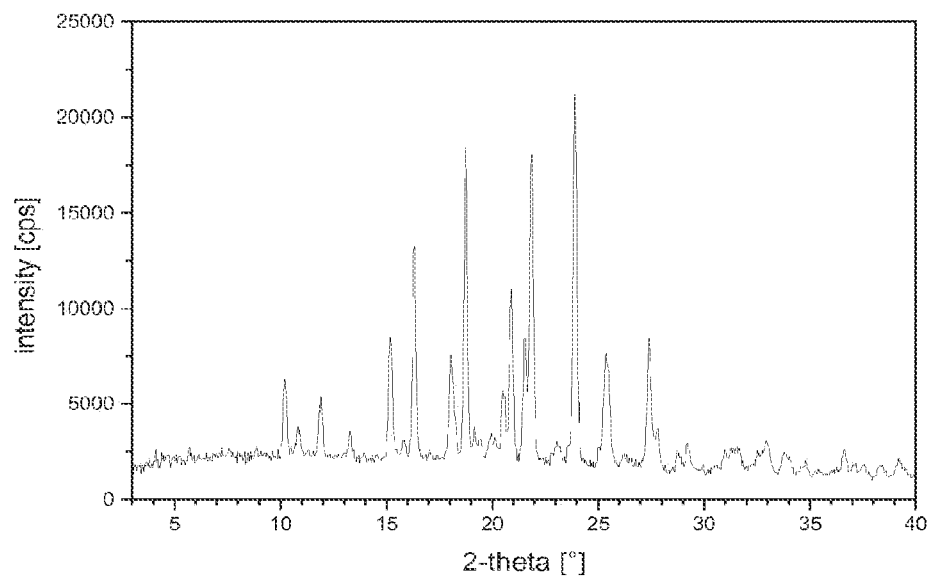

Figure 1.16 X-ray powder diffraction diagram of Gly1 = glycolate, form I
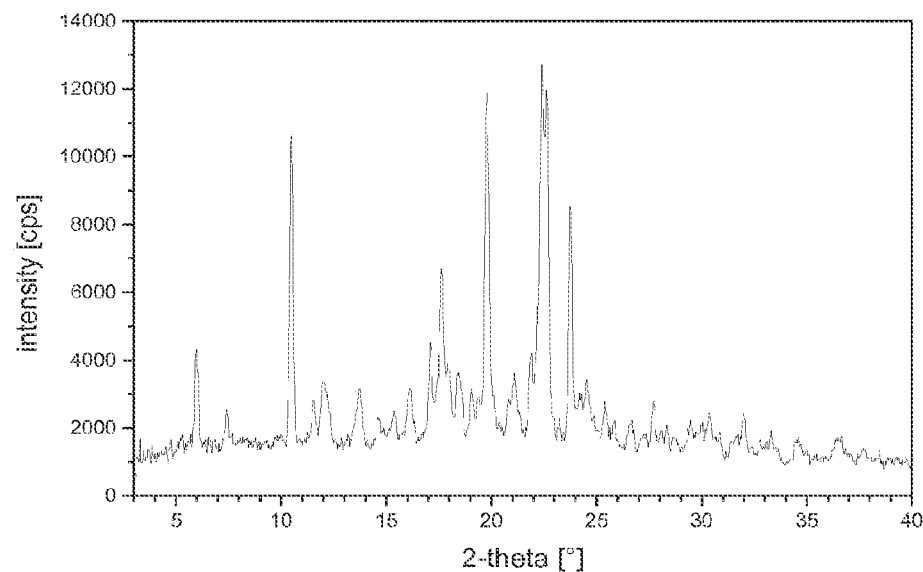
Figure 1.17: X-ray powder diffraction diagram of Cit 1 = citrate, form I
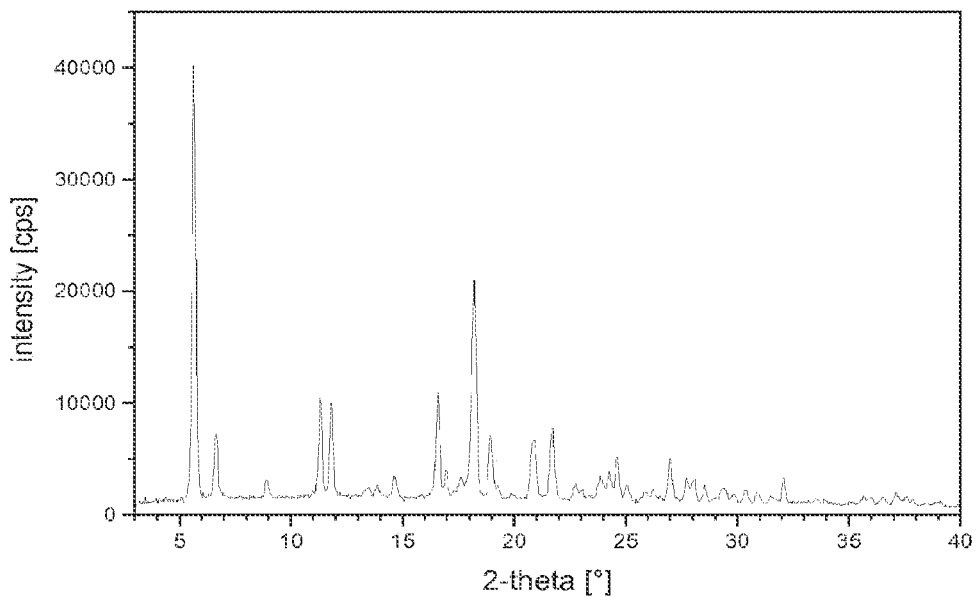

Figure 1.18: X-ray powder diffraction diagram of Man 1 = mandelate, form I
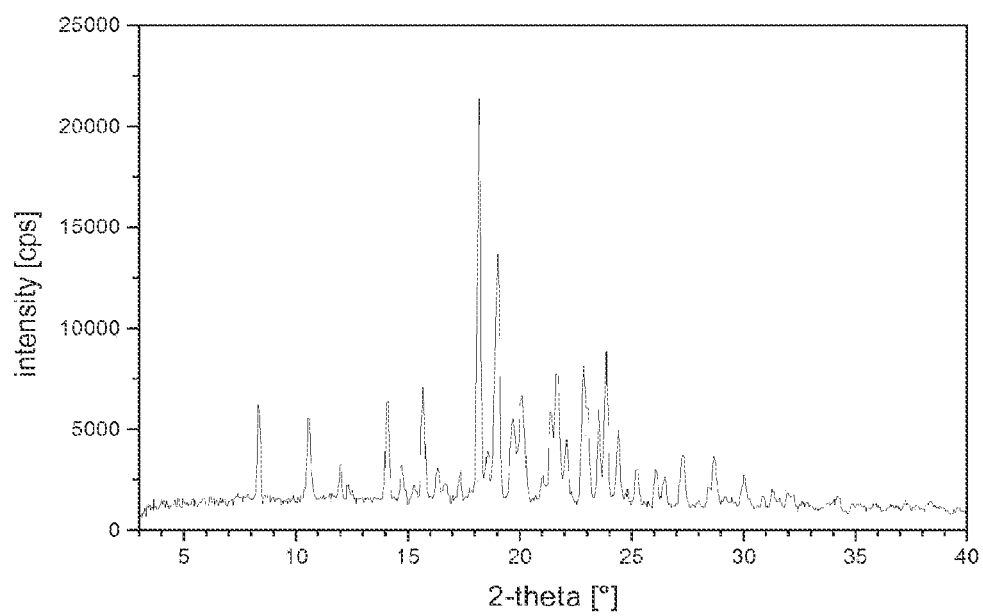
Figure 1.19: X-ray powder diffraction diagram of L-Mal 1 = L-malate, form I
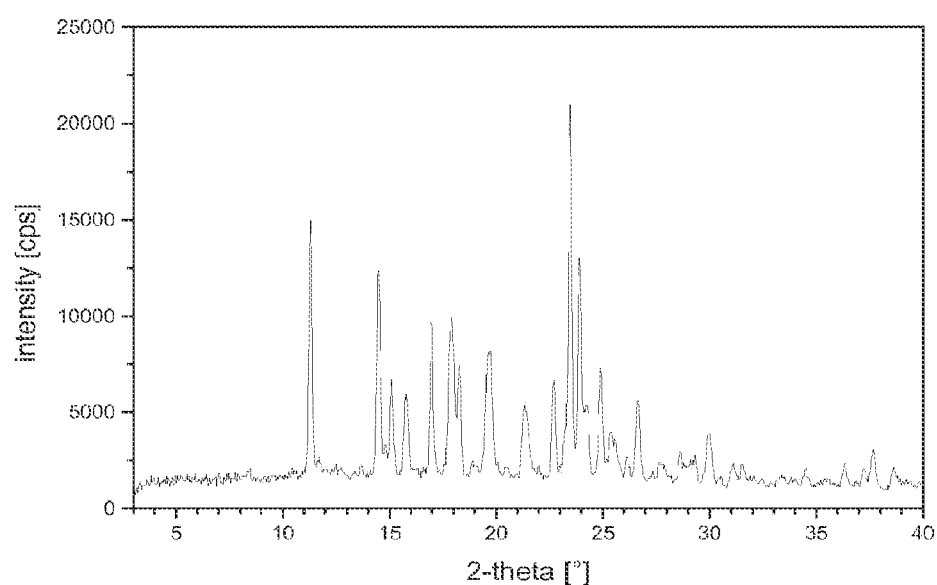

Figure 1.20 X-ray powder diffraction diagram of Nas1 = naphtalene-sulfonate, form I
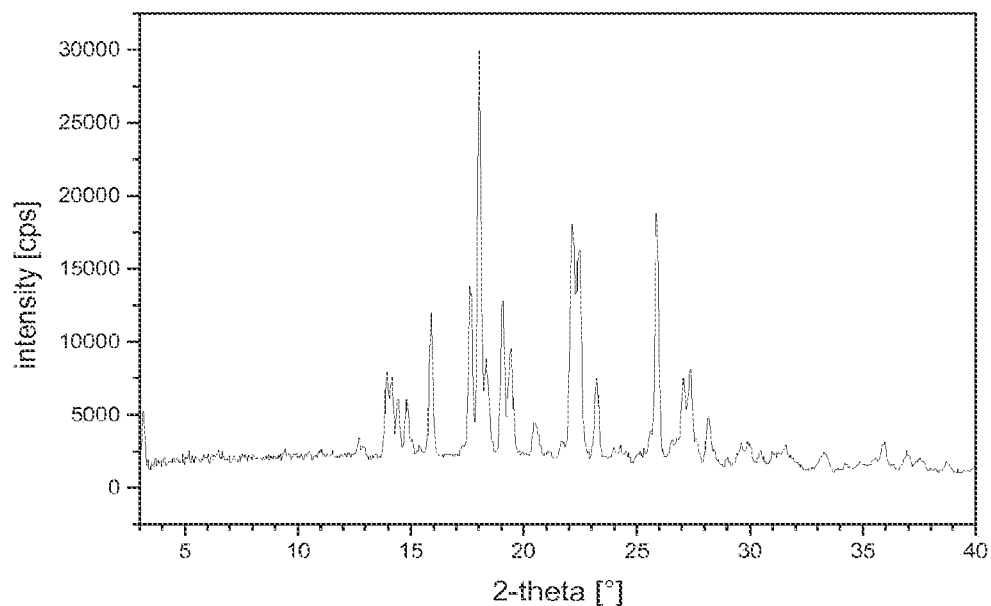
Figure 1.21: X-ray powder diffraction diagram of Fum 3 = fumarate, form III
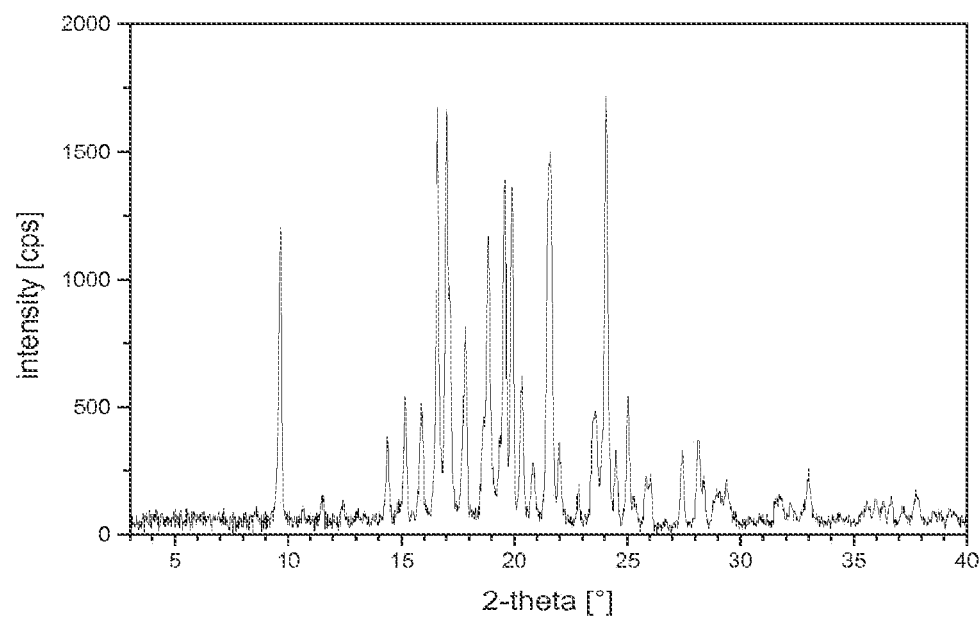

Figure 1.22: X-ray powder diffraction diagram of TOS 2 = tosylate, form II
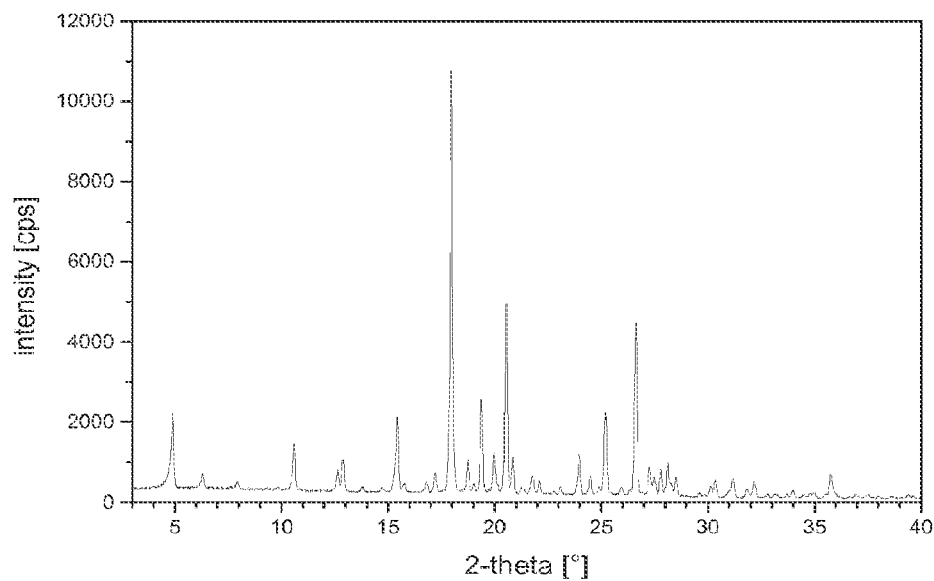
Figure 1.23: X-ray powder diffraction diagram of Cas 2 = camphorsulfonate, form II
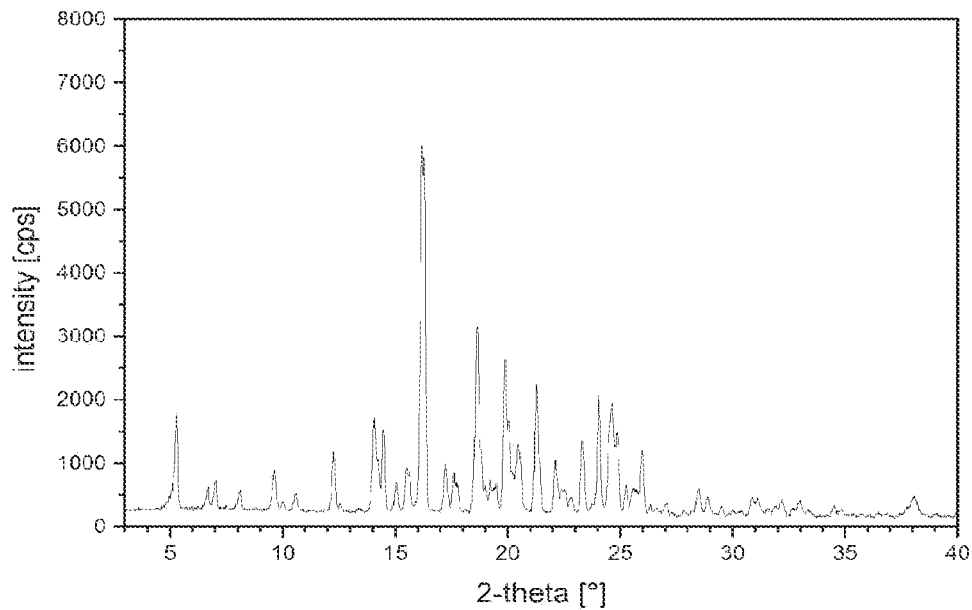

Figure 1.24: X-ray powder diffraction diagram of Gly 3 = glycolate, form II
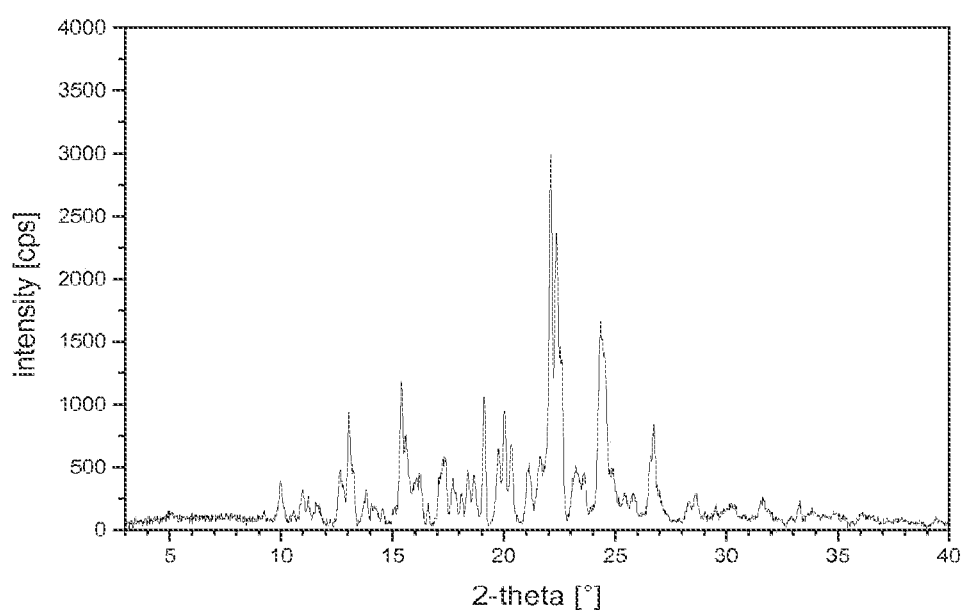

SALTS

CROSS-REFERENCE TO PRIORITY APPLICATIONS

This application is a continuation of U.S. patent application Ser. No. 13/131,926 for New Salts, filed May 31, 2011, which is the national phase entry under 35 U.S. C. §371 of International Application No. PCT/EP2009/067007, filed Dec. 14, 2009, which claims priority to European Patent Application No. 08171699.5, filed Dec. 15, 2008, the contents of which are hereby incorporated by reference in their entireties.

The present invention relate to crystalline salts of flibanserin, 1-[2-(4-(3-trifluoro-methyl-phenyl)piperazin-1-yl)ethyl]-2,3-dihydro-1H-benzimidazol-2-one, to a process for their manufacture, to pharmaceutical formulations containing them and to their use as medicament.

BACKGROUND TO THE INVENTION

The compound 1-[2-(4-(3-trifluoro-methyl-phenyl)piperazin-1-yl)ethyl]-2,3-dihydro-1H-benzimidazol-2-one is known EP 0 526 434 B1 and has the following chemical structure, depicted below as Formula (I)

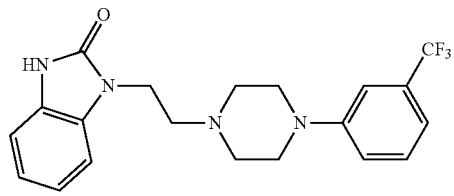

Furthermore the free base of this compound is known from EP 1 414 816 B1 in its polymorph B form, as well as a process for its manufacture.

The above mentioned patents further disclose the use of this compound for the treatment of different diseases inter alia for the treatment of HSDD (Hypoactive Sexual Desire Disorder).

SUMMARY OF THE INVENTION

The aim of the invention is to provide new forms of flibanserin with advantageous properties for pharmaceutical use.

The above mentioned pharmacologically valuable properties of flibanserin disclosed in the prior art constitutes the basic prerequisite for effective use of the compound as pharmaceutical compositions. However, to be permitted for use as a medicament, an active substance must also satisfy further requirements, besides actually being effective for the desired indication. These parameters are largely to do with the physicochemical nature of the active substance.

Without being restrictive, examples of these parameters are the stability of effect of the starting substance under various environmental conditions, the stability during production of the pharmaceutical formulation and stability in the final compositions of the drug. The pharmaceutically active substance used to prepare the pharmaceutical compositions should therefore have great stability which is ensured even under different environmental conditions. This is absolutely essential to prevent pharmaceutical compositions being used which contain breakdown products, for example, in addition to the active substance itself. In such a case the content of active substance present in the pharmaceutical formulation might be lower than specified.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. In addition, the uptake of moisture may reduce the content of pharmaceutically active substance during manufacture if the pharmaceutical substance is exposed to the environment without being protected from moisture in any way. Preferably, therefore, a pharmaceutically active substance should be, if at all, only slightly hygroscopic.

Another criterion which may be of exceptional importance under certain circumstances depending on the choice of formulation or the choice of manufacturing process is the solubility of the active substance. If for example pharmaceutical solutions are prepared (e.g. for infusions) it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterised by high pharmacological potency but also satisfies the above-mentioned physicoehemical requirements as far as possible.

Accordingly, the aim of the present invention is to provide new crystalline salt forms of flibanserin, 1-[2-(4-(3-trifluoro-methyl-phenyl)piperazin-1-yl)ethyl]-2,3-dihydro-1H-benzimidazol-2-one, which are characterized by advantageous physicochemical properties, especially improved solubiliy in water and minimized hygroscopicity Another embodiment of the present invention relates to the process for manufacture of new crystalline salt forms of 1-[2-(4-(3-trifluoro-methyl-phenyl)piperazin-1-yl)ethyl]-2,3-dihydro-1H-benzimidazol-2-one.

Another embodiment of the present invention relates to pharmaceutical compositions containing the new crystalline salt forms of 1-[2-(4-(3-trifluoro-methyl-phenyl)piperazin-1-yl)ethyl]-2,3-dihydro-1H-benzimidazol-2-one and to their use as medicament.

DETAILED DESCRIPTION OF THE INVENTION

In a first aspect, the present invention relates to the following salts and/or crystalline forms and/or crystalline salt forms of the compound 1-[2-(4-(3-trifluoro-methyl-phenyl)piperazin-1-yl)ethyl]-2,3-dihydro-1H-benzimidazol-2-one.

I. Crystalline 1-[2-(4-(3-trifluoro-methyl-phenyl)piperazin-1-yl)ethyl]-2,3-dihydro-1H-benzimidazol-2-one chloride (form I) (=anhydrous form), characterized by a melting point of $T_{fus}$ (onset)=215±5° C. which occurs during thermal analysis using DSC. The DSC diagram is additionally characterised in that two further weakly endothermic signals can be observed at approx. 122° C. and 186° C. Particularly characteristic peaks in the X-ray powder diffractogram of this compound are d=15.99±0.05 Å, d=7.44±0.05 Å, d=3.98±0.05 Å and d=3.44±0.05 Å;

II. Crystalline 1-[2-(4-(3-trifluoro-methyl-phenyl)piperazin-1-yl)ethyl]-2,3-dihydro-1H-benzimidazol-2-one chloride (form III) (=solvate form), characterized by a melting point of $T_{fus}$ (onset)=217±5° C. which occurs during thermal analysis using DSC. The DSC is characterised in that two further weakly endothermic signals can be observed at approx. 56° C. and 121° C. Particularly characteristic peaks in the X-ray powder diffractogram of this compound are d=16.43±0.05 Å, d=5.08±0.05 Å, d=4.35±0.05 Å and d=7.66±0.05 Å;

III. Crystalline 1-[2-(4-(3-trifluoro-methyl-phenyl)piperazin-1-yl)ethyl]-2,3-dihydro-1H-benzimidazol-2-one bromide (form I) (=solvate form), characterized by a melting point of $T_{fus}$ (onset)=252±5° C. which occurs during thermal analysis using DSC. The DSC diagram is additionally characterised in that two further weakly endothermic signals can be observed at approx. 104° C. and 222° C. Particularly characteristic peaks in the X-ray powder diffractogram of this compound are d=3.48±0.05 Å, d=3.33±0.05 Å, d=4.28±0.05 Å and d=3.43±0.05 Å and d=16.03±0.05 Å;

IV. Crystalline 1-[2-(4-(3-trifluoro-methyl-phenyl)piperazin-1-yl)ethyl]-2,3-dihydro-1H-benzimidazol-2-one bromide (form III) (=solvate form), characterized by a melting point of $T_{fus}$ (onset)=252±5° C. which occurs during thermal analysis using DSC. The DSC diagram is additionally characterised in that two further weakly endothermic signals can be observed at approx. 89° C. and 218° C. Particularly characteristic peaks in the X-ray powder diffractogram of this compound are d=15.52±0.05 Å, d=5.15±0.05 Å, d=4.60±0.05 Å and d=4.36±0.05 Å and d=3.94±0.05 Å;

V. Crystalline 1-[2-(4-(3-trifluoro-methyl-phenyl)piperazin-1-yl)ethyl]-2,3-dihydro-1H-benzimidazol-2-one edisylate (form I) (=solvate form), characterized by a melting point of $T_{fus}$ (onset)=144±5° C. which occurs during thermal analysis using DSC. Particularly characteristic peaks in the X-ray powder diffractogram of this compound are d=14.34±0.05 Å, d=3.95±0.05 Å, d=4.64±0.05 Å and d=3.75±0.05 Å and d=9.50±0.05 Å;

VI. Crystalline 1-[2-(4-(3-trifluoro-methyl-phenyl)piperazin-1-yl)ethyl]-2,3-dihydro-1H-benzimidazol-2-one tosylate (form I) (hydrated form), characterized by a melting point of $T_{fus}$ (onset)=238±5° C. which occurs during thermal analysis using DSC. Particularly characteristic peaks in the X-ray powder diffractogram of this compound are d=5.11±0.05 Å, d=4.84±0.05 Å, d=3.93±0.05 Å and d=3.48±0.05 Å;

VII. Crystalline 1-[2-(4-(3-trifluoro-methyl-phenyl)piperazin-1-yl)ethyl]-2,3-dihydro-1H-benzimidazol-2-one mesylate (form I) (=monohydrate form, characterized by a melting point of $T_{fus}$ (onset)=207±5° C. which occurs during thermal analysis using DSC. The DSC diagram is additionally characterised in that two further weakly endothermic signals can be observed at approx. 60° C. Particularly characteristic peaks in the X-ray powder diffractogram of this compound are d=15.25±0.05 Å, d=4.18±0.05 Å, d=3.47±0.05 Å, d=4.95±0.05 Å and d=4.24±0.05 Å; Its solubility in water at room temperature is 1.1 mg/ml. The hygroscoplycity expressed in the uptake of water in the range of 10-90% relative humidity is 3.4%.

VIII. Crystalline 1-[2-(4-(3-trifluoro-methyl-phenyl)piperazin-1-yl)ethyl]-2,3-dihydro-1H-benzimidazol-2-one besylate (form I) (=monohydrate form), characterized by a melting point of $T_{fus}$ (onset)=247±5° C. which occurs during thermal analysis using DSC. The DSC diagram is additionally characterised in that two further weakly endothermic signal can be observed at approx. 111° C. Particularly characteristic peaks in the X-ray powder diffractogram of this compound are d=3.99±0.05 Å, d=4.69±0.05 Å, d=4.85±0.05 Å and d=6.42±0.05 Å; Its solubility in water at room temperature is 0.1 mg/ml. The hygroscoplycity expressed in the uptake of water in the range of 10-90% relative humidity is 0.15%.

IX. Crystalline 1-[2-(4-(3-trifluoro-methyl-phenyl)piperazin-1-yl)ethyl]-2,3-dihydro-1H-benzimidazol-2-one oxalate (form I) (=anhydrous form), characterized by a melting point of $T_{fus}$ (onset)=209±5° C. which occurs during thermal analysis using DSC. Particularly characteristic peaks in the X-ray powder diffractogram of this compound are d=7.09±0.05 Å, d=6.01±0.05 Å, d=4.92±0.05 Å, d=4.24±0.05 Å and d=4.08±0.05 Å; Its solubility in water at room temperature is 1.7 mg/ml. The hygroscoplycity expressed in the uptake of water in the range of 10-90% relative humidity is 0.7%.

X. Crystalline 1-[2-(4-(3-trifluoro-methyl-phenyl)piperazin-1-yl)ethyl]-2,3-dihydro-1H-benzimidazol-2-one oxalate (form V) (=dihydrate form), characterized by a melting point of $T_{fus}$ (onset)=254±5° C. which occurs during thermal analysis using DSC. The DSC diagram is additionally characterised in that two further weakly endothermic signal can be observed at approx. 112° C. and 198° C. Particularly characteristic peaks in the X-ray powder diffractogram of this compound are d=7.09±0.05 Å, d=5.67±0.05 Å, d=5.04±0.05 Å, d=4.87±0.05 Å and d=3.76±0.05 Å;

XI. Crystalline 1-[2-(4-(3-trifluoro-methyl-phenyl)piperazin-1-yl)ethyl]-2,3-dihydro-1H-benzimidazol-2-one saccharinate (form I) (=1.5 hydrated form), characterized by a melting point of $T_{fus}$ (onset)=90±5° C. which occurs during thermal analysis using DSC. Particularly characteristic peaks in the X-ray powder diffractogram of this compound are d=7.86±0.05 Å, d=5.90±0.05 Å, d=5.30±0.05 Å, d=5.14±0.05 Å and d=4.62±0.05 Å; Its solubility in water at room temperature is 0.3 mg/ml. The hygroscoplycity expressed in the uptake of water in the range of 10-90% relative humidity is 0.24%.

XII. Crystalline 1-[2-(4-(3-trifluoro-methyl-phenyl)piperazin-1-yl)ethyl]-2,3-dihydro-1H-benzimidazol-2-one phosphate (form I) (=hemihydrate form), characterized by a melting point of $T_{fus}$ (onset)=182±5° C. which occurs during thermal analysis using DSC. The DSC diagram is additionally characterised in that three further weakly endothermic signal can be observed at approx. 81° C. 141° C. and 164° C. Particularly characteristic peaks in the X-ray powder diffractogram of this compound are d=15.79±0.05 Å, d=5.06±0.05 Å, d=7.90±0.05 Å, d=3.75±0.05 Å;

XIII. Crystalline 1-[2-(4-(3-trifluoro-methyl-phenyl)piperazin-1-yl)ethyl]-2,3-dihydro-1H-benzimidazol-2-one maleate (form I) (=THF solvate), characterized by a melting point of $T_{fus}$ (onset)=98±5° C. which occurs during thermal analysis using DSC. The DSC diagram is additionally characterised in that a further weakly endothermic signal can be observed at approx. 78° C. Particularly characteristic peaks in the X-ray powder diffractogram of this compound are d=9.58±0.05 Å, d=7.71±0.05 Å, d=6.13±0.05 Å, d=5.93±0.05 Å and d=4.62±0.05 Å;

XIV. Crystalline 1-[2-(4-(3-trifluoro-methyl-phenyl)piperazin-1-yl)ethyl]-2,3-dihydro-1H-benzimidazol-2-one maleate (form III) (=anhydrous form), characterized by a melting point of $T_{fus}$ (onset)=172±5° C. which occurs during thermal analysis using DSC. Particularly characteristic peaks in the X-ray powder diffractogram of this compound are d=6.07±0.05 Å, d=5.16±0.05 Å, d=4.52±0.05 Å, d=4.10±0.05 Å and d=3.20±0.05 Å;

XV. Crystalline 1-[2-(4-(3-trifluoro-methyl-phenyl)piperazin-1-yl)ethyl]-2,3-dihydro-1H-benzimidazol-2-one ethansulfonate (form I) (=monohydrate form), characterized by a melting point of $T_{fus}$ (onset)=207±5° C. which occurs during thermal analysis using DSC. The DSC diagram is additionally characterised in that two further weakly endothermic signal can be observed at approx. 105° C. and 189° C. Particularly characteristic peaks in the X-ray powder diffractogram of this compound are d=15.30±0.05 Å, d=7.25±0.05 Å, d=5.00±0.05 Å, d=4.34±0.05 Å and d=4.23±0.05 Å; Its solubility in water at room temperature is 1.3 mg/ml. The hygroscoplycity expressed in the uptake of water in the range of 10-90% relative humidity is 0.32%.

XVI. Crystalline 1-[2-(4-(3-trifluoro-methyl-phenyl)piperazin-1-yl)ethyl]-2,3-dihydro-1H-benzimidazol-2-one camphorsulfonate (form I) (=anhydrous form), characterized by a melting point of $T_{fus}$ (onset)=217±5° C. which occurs during thermal analysis using DSC. The DSC diagram is additionally characterised in that two further weakly endothermic signal can be observed at approx. 177° C. Particularly characteristic peaks in the X-ray powder diffractogram of this compound are d=16.32±0.05 Å, d=5.69±0.05 Å, d=5.45±0.05 Å, d=5.50±0.05 Å and d=3.62±0.05 Å;

XVII. Crystalline 1-[2-(4-(3-trifluoro-methyl-phenyl)piperazin-1-yl)ethyl]-2,3-dihydro-1H-benzimidazol-2-one malonate (form I) (=dihydrate form), characterized by a melting point of $T_{fus}$ (onset)=103±5° C. which occurs during thermal analysis using DSC. The DSC diagram is additionally characterised in that two further weakly endothermic signal can be observed at approx. 79° C. Particularly characteristic peaks in the X-ray powder diffractogram of this compound are d=23.23±0.05 Å, d=8.56±0.05 Å, d=4.62±0.05 Å, d=4.19±0.05 Å and d=3.72±0.05 Å;

XVIII. Crystalline 1-[2-(4-(3-trifluoro-methyl-phenyl)piperazin-1-yl)ethyl]-2,3-dihydro-1H-benzimidazol-2-one molonate (form II) (=solvate form), characterized by the data listed in table 2.9;

XIX. Crystalline 1-[2-(4-(3-trifluoro-methyl-phenyl)piperazin-1-yl)ethyl]-2,3-dihydro-1H-benzimidazol-2-one malonate (form VI) (=dihydrate form), characterized by the data listed in table 2.10;

XX. Crystalline 1-[2-(4-(3-trifluoro-methyl-phenyl)piperazin-1-yl)ethyl]-2,3-dihydro-1H-benzimidazol-2-one salicylate (form I) (=anhydrous form), characterized by the data listed in table 2.11;

XXI. Crystalline 1-[2-(4-(3-trifluoro-methyl-phenyl)piperazin-1-yl)ethyl]-2,3-dihydro-1H-benzimidazol-2-one L-tartrate (=dihydrate form), characterized by a melting point of $T_{fus}$ (onset)=151±5° C. which occurs during thermal analysis using DSC. Particularly characteristic peaks in the X-ray powder diffractogram of this compound are d=5.46±0.05 Å, d=4.94±0.05 Å, d=4.30±0.05 Å, d=4.08±0.05 Å and d=3.74±0.05 Å;

XXII. Crystalline 1-[2-(4-(3-trifluoro-methyl-phenyl)piperazin-1-yl)ethyl]-2,3-dihydro-1H-benzimidazol-2-one hemifumarate (form I) (=anhydrous form), characterized by a melting point of $T_{fus}$ (onset)=195±5° C. which occurs during thermal analysis using DSC. Particularly characteristic peaks in the X-ray powder diffractogram of this compound are d=6.38±0.05 Å, d=5.19±0.05 Å, d=4.87±0.05 Å, d=3.72±0.05 Å and d=3.45±0.05 Å;

XXIII. Crystalline 1-[2-(4-(3-trifluoro-methyl-phenyl) piperazin-1-yl)ethyl]-2,3-dihydro-1H-benzimidazol-2-one fumarate (form II) (=dihydrate form), characterized by a melting point of $T_{fus}$ (onset)=193±5° C. which occurs during thermal analysis using DSC. The DSC diagram is additionally characterised in that two further weakly endothermic signal can be observed at approx. 157° C. Particularly characteristic peaks in the X-ray powder diffractogram of this compound are d=5.42±0.05 Å, d=4.73±0.05 Å, d=4.25±0.05 Å, d=4.06±0.05 Å and d=3.72±0.05 Å;

XXIV. Crystalline 1-[2-(4-(3-trifluoro-methyl-phenyl) piperazin-1-yl)ethyl]-2,3-dihydro-1H-benzimidazol-2-one glycolate (form I) (=hydrate form), characterized by a melting point of $T_{fus}$ (onset)=139±5° C. which occurs during thermal analysis using DSC. The DSC diagram is additionally characterised in that two further weakly endothermic signal can be observed at approx. 30° C. and 115° C. Particularly characteristic peaks in the X-ray powder diffractogram of this compound are d=3.96±0.05 Å, d=4.48±0.05 Å, d=3.93±0.05 Å, d=8.43±0.05 Å and d=3.74±0.05 Å;

XXV. Crystalline 1-[2-(4-(3-trifluoro-methyl-phenyl)piperazin-1-yl)ethyl]-2,3-dihydro-1H-benzimidazol-2-one citrate (form I) (=solvate form), characterized by a melting point of $T_{fus}$ (onset)=176±5° C. which occurs during thermal analysis using DSC. The DSC diagram is additionally characterised in that two further weakly endothermic signal can be observed at approx. 123° C. Particularly characteristic peaks in the X-ray powder diffractogram of this compound are d=15.61±0.05 Å, d=7.81±0.05 Å, d=7.47±0.05 Å, d=5.34±0.05 Å and d=4.87±0.05 Å;

XXVI. Crystalline 1-[2-(4-(3-trifluoro-methyl-phenyl) piperazin-1-yl)ethyl]-2,3-dihydro-1H-benzimidazol-2-one mandelate (form I) (=anhydrous form), characterized by a melting point of $T_{fus}$ (onset)=148±5° C. which occurs during thermal analysis using DSC. Particularly characteristic peaks in the X-ray powder diffractogram of this compound are d=4.87±0.05 Å, d=4.66±0.05 Å, d=4.10±0.05 Å, d=3.88±0.05 Å and d=3.73±0.05 Å;

XXVII. Crystalline 1-[2-(4-(3-trifluoro-methyl-phenyl) piperazin-1-yl)ethyl]-2,3-dihydro-1H-benzimidazol-2-one L-malate (form I) (=monohydrate form), characterized by a melting point of $T_{fus}$ (onset)=176±5° C. which occurs during thermal analysis using DSC. The DSC diagram is additionally characterised in that two further weakly endothermic signal can be observed at approx. 106° C. Particularly characteristic peaks in the X-ray powder diffractogram of this compound are d=7.82±0.05 Å, d=6.10±0.05 Å, d=5.22±0.05 Å, d=4.95±0.05 Å and d=3.79±0.05 Å;

XXVIII. Crystalline 1-[2-(4-(3-trifluoro-methyl-phenyl) piperazin-1-yl)ethyl]-2,3-dihydro-1H-benzimidazol-2-one succinate (form I) (=dihydrate form), characterized by the data listed in table 2.18;

XXIX. Crystalline 1-[2-(4-(3-trifluoro-methyl-phenyl) piperazin-1-yl)ethyl]-2,3-dihydro-1H-benzimidazol-2-one naphthalenesulfonate (form I) (=hemihydrate form), characterized by peaks in the X-ray powder diffractogram which occur at d=4.92±0.05 Å, d=3.43±0.05 Å, d=4.00±0.05 Å, and d=3.96±0.05 Å;

XXX. Crystalline 1-[2-(4-(3-trifluoro-methyl-phenyl)piperazin-1-yl)ethyl]-2,3-dihydro-1H-benzimidazol-2-one tosylate (form II) (=anhydrous form), characterized by a melting point of $T_{fus}$ (onset)=241±5° C. which occurs during thermal analysis using DSC. Particularly characteristic peaks in the X-ray powder diffractogram of this compound are d=4.94±0.05 Å, d=4.57±0.05 Å, d=4.32±0.05 Å, d=3.53±0.05 Å and d=3.35±0.05 Å; Its solubility in water at room temperature is 0.09 mg/ml. The hygroscoplycity expressed in the uptake of water in the range of 10-90% relative humidity is 0.25%.

XXXI. Crystalline 1-[2-(4-(3-trifluoro-methyl-phenyl) piperazin-1-yl)ethyl]-2,3-dihydro-1H-benzimidazol-2-one fumarate (form III) (=anhydrous form), characterized by a melting point of $T_{fus}$ (onset)=202±5° C. which occurs during thermal analysis using DSC. Particularly characteristic peaks in the X-ray powder diffractogram of this compound are d=5.33±0.05 Å, d=5.21±0.05 Å, d=4.53±0.05 Å, d=4.12±0.05 Å and d=3.69±0.05 Å; Its solubility in water at room temperature is 0.5 mg/ml. The hygroscoplycity expressed in the uptake of water in the range of 10-90% relative humidity is 0.28%.

XXXII. Crystalline 1-[2-(4-(3-trifluoro-methyl-phenyl) piperazin-1-yl)ethyl]-2,3-dihydro-1H-benzimidazol-2-one camphorsulfonate (form II) (=anhydrous form), characterized by a melting point of $T_{fus}$ (onset)=231±5° C. which occurs during thermal analysis using DSC. Particularly characteristic peaks in the X-ray powder diffractogram of this compound are d=5.47±0.05 Å, d=5.44±0.05 Å, d=4.76±0.05 Å, d=4.46±0.05 Å and d=3.70±0.05 Å; Its solubility in water at room temperature is 0.7 mg/ml. The hygroscoplycity expressed in the uptake of water in the range of 10-90% relative humidity is 0.13%.

XXXIII. Crystalline 1-[2-(4-(3-trifluoro-methyl-phenyl) piperazin-1-yl)ethyl]-2,3-dihydro-1H-benzimidazol-2-one glycolate (form II) (=hydrate form), characterized by a melting point of $T_{fus}$ (onset)=231±5° C. which occurs during thermal analysis using DSC. Particularly characteristic peaks in the X-ray powder diffractogram of this compound are d=5.75±0.05 Å, d=4.64±0.05 Å, d=4.43±0.05 Å, d=4.02±0.05 Å and d=3.97±0.05 Å; Its solubility in water at room temperature is 0.5 mg/ml. The hygroscoplycity expressed in the uptake of water in the range of 10-90% relative humidity is 0.20%.

In another embodiment the invention relates to a process for the preparation of the new crystalline salt forms of filbanserin as specified above under I) to XXIX).

According to the invention the compounds specified above can be obtained by
i) dissolving the free base of flibanserin and the acid providing the anion for salt formation in a suitable solvent (preferably TFE/water (80:20))
ii) mixing the free base of flibanserin with the acid at a predetermined base/acid molar ratio, which is selected from 1:1 or 2:1 depending on the acid
iii) removing tne solvent (e.g. evaporation under reduced pressure)
iv) adding a suitable crystallization solvent to the residue obtained by step iii), and heating the reaction mixture slowly up (e.g. at a healing rate of about 5° C./min) to about 50° C.; leaving it to stand for a further period of time (e.g. about 30 min)
v) slowly cooling down (e.g. at a cooling rate of about 5° C./h) the reaction mixture to a suitable crystallization temperature, (e.g. between 20° C. or 3° C.) and leaving it to stand until enough crystals are formed
vi) isolating the precipitated crystals.

In the process according to the invention the free base of the compound of formula (I) is dissolved in a suitable solvent, such as TFE/water (80:20). The acid used for the crystallization is dissolved as well in a suitable solvent, such as TFE/water (80:20) (depending on the acid). The free base of the compound of formula (I) is then mixed with the acid at a predetermined base/acid molar ratio, which is selected from 1:1 or 2:1 depending on the acid. Then, the solvent is evaporated under reduced pressure. After evaporation of the solvent has occurred, a suitable crystallization solvent is added to the reaction mixture, and the reaction mixture is slowly heated up to 50° C. (e.g. a heating rate of about 5° C./min). Without being limited, suitable solvents for the crystallization are etnanol, tetrahydrofuran, dichloromethane, n-mthylpyrrolidone, propyl acetate, methyl tert-butyl ether, 1,4 dioxane, 1,2-dimetoxyethane, water, 2,2,2,-trifluoroethanol, chloroform, methanol, nitrobenzene, nitromethane, cyclohexanone, propionitrile, ethyl phenyl ether, diisobutyl keton, isophorone, water/ethanol (20/80), water/n-methytpyrrolidone (80/20), water/2,2,2-trifluoroethanol (20/80), water/acteone (20/80) and water/DMSO (80/20). After staying for about 30 minutes at 50° C., the reaction mixture is slowly cooled down (e.g. at a cooling rate of 5° C./h) to a suitable crystallization temperature, which is for example between 20° C. or 3° C. The reaction mixture stays at this temperature until enough crystals are formed, which can then be collected, for example by filtration.

The salt forms of flibanserin as specified above under I) to XXIX) were investigated more thoroughly by X-ray powder diffraction and thermal analysis (DSC). The diagrams obtained are shown in FIGS. 1.1 to 1.23 Tables 1.1 to 1.23 contain the data obtained in the analysis.

Tables 2.1 to 2.18 contain the single crystal data obtained in the analysis.

TABLE 1

Thermal analysis, stoichiometry and single crystal data of the different salts of 1-[2-(4-(3-trifluoro-methyl-phenyl)piperazin-1-yl)ethyl]-2,3-dihydro-1H-benzimidazol-2-one

| salt form | salt form full name | ratio base/acid | thermal analysis $T_{fus}$ (onset) | single cyrstal data | XRPD data |
|---|---|---|---|---|---|
| HCl 1 | chloride, form I (=anhydrous form) | 1:1 | T = 215° C. add. endotherm. signals: T = 122° C. (following by an exotherm. signal) T = 186° C. (following by an exotherm. signal) | n.d. | See Table 1.1a |
| HCl 3 | chloride, form III (=solvate form) | 1:1 | T = 217° C. add. endotherm. signals: T = 56° C. T = 121° C. (following by an exotherm. signal) | n.d. | See Table 1.1b |
| HBr 1 | bromide from I (=solvate form) | 1:1 | T = 252° C. add. endotherm. signals: T = 104° C. T = 222° C. following by an exotherm. signal) | n.d. | See Table 1.2a |

TABLE 1-continued

Thermal analysis, stoichiometry and single crystal data of the different salts of 1-[2-(4-(3-trifluoro-methyl-phenyl)piperazin-1-yl)ethyl]-2,3-dihydro-1H-benzimidazol-2-one

| salt form | salt form full name | ratio base/acid | thermal analysis $T_{fus}$ (onset) | single cyrstal data | XRPD data |
|---|---|---|---|---|---|
| HBr 3 | bromide from III (=solvate form) | 1:1 | T = 252° C. add. endotherm. signals: T = 89° C. T = 218° C. (following by an exotherm. signal) | see Table 2.1 | See Table 1.2b |
| Eds1 | edisylate form I (=solvate form) | 1:1 | T = 144° C. | n.d. | See Table 1.3 |
| Tos 1 | tosylate form I (hydrated form) | 1:1 | T = 238° C. | n.d. | See Table 1.4 |
| Mes 1 | mesylate form I (=monohydrate form) | 1:1 | T = 207° C. add. endotherm. signal: $T_1$ = 60° C. | n.d. | See Table 1.5 |
| Bes 1 | besylate form I (=monohydrate form) | 1:1 | T = 247° C. add. endotherm. signal: T = 111° C. | n.d. | See Table 1.6 |
| Oxa 1 | oxalate form I (=anhydrous form) | 1:1 | T = 209° C. | see Table 2.2 | See Table 1.7a |
| Oxa 5 | oxalate form V (=dihydrate form) | 1:1 | T = 254° C. add. endotherm. signal: T = 112° C. T = 198° C. | see Table 2.3 | See Table 1.7b |
| Sac1 | sacharinate form I (1,5 hydrated form) | 1:1 | T = 90° C. | see Table 2.4 | See Table 1.8 |
| Pho | phosphate form I (=hemihydrate form) | 1:1 | T = 182° C. add. endotherm. signals T = 81° C. T = 141° C. T = 164° C. | n.d. | See Table 1.9 |
| Mae1 | maleate form I (=THF solvate) | 1:1 | T = 98° C. add. endotherm. signal T = 78° C. | see Table 2.5 | See Table 1.10a |
| Mae3 | maleate form III (=anhydrous form) | 1:1 | T = 172° C. | see Table 2.6 | See Table 1.10b |
| Ets | ethanesulfonate (=monhydrate form) | 1:1 | T = 207° C. add. endotherm. signals: T = 105° C. T = 189° C. (following by an exotherm. signal) | see Table 2.7 | See Table 1.11 |
| Cas1 | camphorsulfonate form I (=anhydrous form) | 1:1 | T = 217° C. add. endotherm. signal: T = 177° C. | n.d. | See Table 1.12 |
| Mao 1 | malonate form I (=dihydrate form) | 1:1 | T = 103° C. add. endotherm. signal: T = 79° C. | see Table 2.8 | See Table 1.13 |
| Mao 2 | malonate form II (=solvate form) | 1:1 | n.d. | see Table 2.9 | n.d. |
| Mao 6 | malonate form VI (=dihydrate form) | 1:1 | n.d. | see Table 2.10 | n.d. |
| Sal 1 | salicylate form I (=anhydrous form) | 1:1 | n.d. | see Table 2.11 | n.d. |
| L-Tart 1 | L-tartate form (=dihydrate form) | 1:1 | T = 151° C. | see Table 2.12 | See Table 1.14 |
| Fum 1 | fumarate form I (=anhydrous form) (co-crystal) | 2:1 | T = 195° C. | see Table 2.13 | See Table 1.15a |
| Fum 2 | fumarate form II (=dihydrate form) | 2:1 | T = 193° C. add. endotherm. signal: T = 157° C. | see Table 2.14 | See Table 1.15b |
| Gly 1 | glycolate form I (=hydrate form) | 1:1 | T = 139° C. add. endotherm. signals: T = 30° C. T = 115° C. (following by an exotherm. signal) | n.d. | See Table 1.16 |

TABLE 1-continued

Thermal analysis, stoichiometry and single crystal data of the different salts of 1-[2-(4-(3-trifluoro-methyl-phenyl)piperazin-1-yl)ethyl]-2,3-dihydro-1H-benzimidazol-2-one

| salt form | salt form full name | ratio base/acid | thermal analysis $T_{fus}$ (onset) | single cyrstal data | XRPD data |
|---|---|---|---|---|---|
| Cit1 | citrate form I (=solvate form) | 1:1 | T = 176° C. add. endotherm. signal: T = 123° C. | see Table 2.15 | See Table 1.17 |
| Man 1 | mandelate form I (=anhydrous form) | 1:1 | T = 148° C. | see Table 2.16 | See Table 1.18 |
| L-Mal 1 | L-malate form I (=monohydrate form) | 1:1 | T = 176° C. add. endotherm. signal: T = 106° C. | see Table 2.17 | See Table 1.19 |
| Suc 1 | succinate form I (=dihydrate form) | 1:1 | n.d. | see Table 2.18 | n.d. |
| Nas1 | naphtalene-sulfonate form I (=hemihydrate form) | 1:1 | n.d. | n.d. | See Table 1.20 |
| Tos 2 | tosylate form II (=anhydrous form) | 1:1 | T = 241° C. | n.d. | See Table 1.21 |
| Fum 3 | fumarate, form III (=anhydrous form) | 1:1 | T = 202° C. | n.d. | See Table 1.22 |
| Cas 2 | camphorsulfonate form II (=anhydrous form) | 1:1 | T = 231° C. | n.d. | See Table 1.23 |
| Gly 2 | glycolate form II (=hydrate form) | 1:1 | T = 145° C. | n.d. | See Table 1.24 |

* $T_{fus}$ (onset) = melting point;
n.d. = not determined

The values of the X-ray powder reflections and intensities (normalized) as recorded for the crystalline salt forms in accordance with the present invention are displayed in the preceding tables 1.1 to 1.23. For each crystalline salt form, the values (d [Å]) of the reflection peaks with the highest relative intensities the highest values of din the corresponding table characterizes this crystalline salt form. The value "2-theta [*]" denotes the angle of diffraction in degrees and the value "d [Å] spacing" denotes the specified distances in Å between the lattice planes.

TABLE 1.1a

X-ray powder reflections and intensity (normalized) of HCl1 = chloride, form I

| 2-theta [°] | d [Å] spacing | I/I$_0$ [%] |
|---|---|---|
| 5.18 | 17.05 | 32 |
| 5.52 | 15.99 | 100 |
| 6.23 | 14.20 | 8 |
| 7.01 | 12.59 | 10 |
| 8.75 | 10.10 | 38 |
| 9.18 | 9.62 | 13 |
| 9.50 | 9.30 | 11 |
| 10.36 | 8.53 | 15 |
| 10.94 | 8.08 | 11 |
| 11.06 | 7.99 | 11 |
| 11.88 | 7.44 | 63 |
| 13.41 | 6.59 | 38 |
| 13.93 | 6.35 | 17 |
| 14.18 | 6.24 | 18 |
| 14.97 | 5.91 | 22 |
| 15.18 | 5.83 | 17 |
| 15.49 | 5.71 | 16 |
| 16.22 | 5.46 | 28 |
| 16.94 | 5.23 | 25 |
| 17.14 | 5.17 | 32 |
| 17.55 | 5.05 | 34 |
| 18.33 | 4.83 | 21 |
| 19.64 | 4.52 | 27 |
| 20.22 | 4.39 | 17 |
| 21.00 | 4.23 | 48 |
| 21.38 | 4.15 | 22 |
| 22.32 | 3.98 | 62 |
| 22.64 | 3.92 | 21 |
| 23.00 | 3.86 | 16 |
| 23.52 | 3.78 | 19 |
| 24.51 | 3.63 | 11 |
| 25.85 | 3.44 | 54 |
| 26.30 | 3.38 | 33 |
| 27.04 | 3.29 | 41 |
| 27.66 | 3.22 | 13 |
| 27.78 | 3.21 | 17 |
| 28.11 | 3.17 | 24 |
| 28.31 | 3.15 | 23 |
| 28.80 | 3.10 | 13 |
| 29.23 | 3.05 | 19 |
| 29.48 | 3.02 | 16 |
| 30.13 | 2.96 | 17 |

TABLE 1.1b

X-ray powder reflections and intensity (normalized) of HCl3 = chloride, form III

| 2-theta [°] | d [Å] spacing | I/I$_0$ [%] |
|---|---|---|
| 5.37 | 16.43 | 100 |
| 6.90 | 12.79 | 24 |
| 8.70 | 10.16 | 58 |
| 9.10 | 9.71 | 46 |
| 10.21 | 8.66 | 47 |
| 11.54 | 7.66 | 80 |
| 11.84 | 7.47 | 45 |
| 12.13 | 7.29 | 30 |
| 13.32 | 6.64 | 57 |
| 14.03 | 6.30 | 47 |
| 14.82 | 5.97 | 38 |
| 14.90 | 5.94 | 38 |
| 15.30 | 5.78 | 46 |
| 15.38 | 5.75 | 48 |
| 15.50 | 5.71 | 48 |
| 16.23 | 5.45 | 38 |
| 16.61 | 5.33 | 38 |
| 16.86 | 5.25 | 48 |
| 17.02 | 5.20 | 46 |
| 17.44 | 5.08 | 99 |
| 18.20 | 4.87 | 32 |
| 18.93 | 4.68 | 42 |
| 19.23 | 4.61 | 54 |
| 19.73 | 4.50 | 42 |
| 20.40 | 4.35 | 96 |
| 20.92 | 4.24 | 66 |
| 21.22 | 4.18 | 37 |
| 21.34 | 4.16 | 35 |
| 22.00 | 4.04 | 63 |
| 22.21 | 4.00 | 54 |
| 22.33 | 3.98 | 47 |
| 22.87 | 3.88 | 56 |
| 23.47 | 3.79 | 44 |
| 24.06 | 3.69 | 24 |
| 24.25 | 3.67 | 24 |
| 25.18 | 3.53 | 33 |
| 25.63 | 3.47 | 82 |
| 26.11 | 3.41 | 42 |
| 26.68 | 3.34 | 53 |
| 26.98 | 3.30 | 40 |
| 27.05 | 3.29 | 38 |
| 27.64 | 3.22 | 44 |
| 27.91 | 3.19 | 39 |
| 28.44 | 3.13 | 33 |
| 29.03 | 3.07 | 33 |
| 29.92 | 2.98 | 34 |
| 30.73 | 2.91 | 30 |

TABLE 1.2a

X-ray powder reflections and intensity (normalized) of HBr1 = hydrobromide, form I

| 2-theta [°] | d [Å] spacing | I/I$_0$ [%] |
|---|---|---|
| 5.51 | 16.03 | 58 |
| 10.21 | 8.65 | 13 |
| 11.86 | 7.45 | 50 |
| 12.92 | 6.84 | 22 |
| 13.16 | 6.72 | 18 |
| 13.82 | 6.40 | 17 |
| 14.02 | 6.31 | 28 |
| 14.49 | 6.12 | 24 |
| 15.34 | 5.77 | 28 |
| 16.01 | 5.53 | 22 |
| 16.94 | 5.23 | 31 |
| 17.16 | 5.16 | 32 |
| 17.98 | 4.93 | 23 |
| 18.21 | 4.87 | 18 |
| 19.02 | 4.66 | 22 |
| 19.53 | 4.54 | 42 |
| 19.91 | 4.45 | 25 |
| 20.25 | 4.38 | 53 |
| 20.75 | 4.28 | 70 |
| 21.16 | 4.19 | 29 |
| 21.97 | 4.04 | 49 |
| 22.60 | 3.93 | 32 |
| 23.10 | 3.85 | 24 |
| 23.92 | 3.71 | 15 |
| 25.55 | 3.48 | 100 |
| 25.96 | 3.43 | 66 |
| 26.70 | 3.33 | 84 |
| 27.79 | 3.21 | 38 |
| 28.14 | 3.17 | 32 |
| 28.95 | 3.08 | 35 |
| 29.40 | 3.03 | 20 |
| 29.82 | 2.99 | 22 |
| 31.21 | 2.86 | 21 |
| 31.89 | 2.80 | 14 |
| 32.33 | 2.77 | 18 |
| 32.84 | 2.72 | 16 |
| 33.83 | 2.65 | 16 |
| 35.81 | 2.50 | 16 |
| 38.55 | 2.33 | 15 |

TABLE 1.2b

X-ray powder reflections and intensity (normalized) of HBr3 = hydrobromide, form III

| 2-theta [°] | d [Å] spacing | I/I$_0$ [%] |
|---|---|---|
| 5.69 | 15.52 | 100 |
| 7.13 | 12.38 | 24 |
| 12.20 | 7.25 | 54 |
| 13.24 | 6.68 | 31 |
| 14.13 | 6.26 | 35 |
| 14.85 | 5.96 | 27 |
| 16.24 | 5.45 | 24 |
| 17.21 | 5.15 | 56 |
| 18.05 | 4.91 | 26 |
| 19.29 | 4.60 | 63 |
| 19.93 | 4.45 | 28 |
| 20.37 | 4.36 | 71 |
| 20.97 | 4.23 | 43 |
| 21.54 | 4.12 | 24 |
| 22.13 | 4.01 | 36 |
| 22.54 | 3.94 | 64 |
| 23.25 | 3.82 | 24 |
| 23.58 | 3.77 | 21 |
| 24.04 | 3.70 | 26 |
| 25.38 | 3.50 | 29 |
| 25.74 | 3.46 | 56 |
| 26.26 | 3.39 | 35 |
| 26.50 | 3.36 | 31 |
| 26.92 | 3.30 | 32 |
| 27.89 | 3.19 | 37 |
| 28.31 | 3.15 | 26 |
| 30.21 | 2.95 | 33 |
| 30.76 | 2.90 | 18 |
| 31.36 | 2.85 | 21 |
| 32.31 | 2.77 | 17 |
| 32.91 | 2.72 | 21 |
| 35.08 | 2.56 | 16 |
| 35.99 | 2.49 | 17 |

TABLE 1.3

X-ray powder reflections and intensity (normalized) of Eds1 = edisylate, form I

| 2-theta [°] | d [Å] spacing | I/I₀ [%] |
|---|---|---|
| 6.15 | 14.34 | 100 |
| 7.01 | 12.59 | 19 |
| 7.70 | 11.47 | 23 |
| 8.73 | 10.11 | 21 |
| 9.29 | 9.50 | 56 |
| 9.69 | 9.12 | 26 |
| 10.30 | 8.58 | 21 |
| 11.03 | 8.01 | 5 |
| 11.34 | 7.79 | 38 |
| 12.10 | 7.31 | 27 |
| 13.15 | 6.72 | 31 |
| 13.78 | 6.42 | 40 |
| 14.30 | 6.19 | 36 |
| 15.32 | 5.78 | 37 |
| 16.13 | 5.49 | 21 |
| 17.15 | 5.17 | 49 |
| 17.85 | 4.96 | 43 |
| 18.64 | 4.75 | 45 |
| 19.11 | 4.64 | 86 |
| 20.04 | 4.43 | 24 |
| 20.58 | 4.31 | 57 |
| 20.88 | 4.25 | 37 |
| 21.06 | 4.21 | 32 |
| 21.43 | 4.14 | 55 |
| 22.06 | 4.03 | 23 |
| 22.48 | 3.95 | 99 |
| 22.84 | 3.89 | 29 |
| 23.34 | 3.81 | 27 |
| 23.69 | 3.75 | 87 |
| 24.28 | 3.66 | 43 |
| 24.76 | 3.59 | 28 |
| 25.15 | 3.54 | 23 |
| 25.89 | 3.44 | 22 |
| 25.98 | 3.43 | 24 |
| 26.56 | 3.35 | 31 |
| 27.10 | 3.29 | 20 |
| 27.18 | 3.28 | 20 |
| 27.81 | 3.20 | 24 |
| 28.16 | 3.17 | 28 |
| 28.70 | 3.11 | 20 |
| 28.78 | 3.10 | 19 |
| 29.62 | 3.01 | 19 |
| 29.70 | 3.00 | 18 |
| 30.64 | 2.91 | 19 |

TABLE 1.4

X-ray powder reflections and intensity (normalized) of Tos1 = tosylate, form I

| 2-theta [°] | d [Å] spacing | I/I₀ [%] |
|---|---|---|
| 3.29 | 26.82 | 20 |
| 11.03 | 8.01 | 17 |
| 12.99 | 6.80 | 17 |
| 13.76 | 6.43 | 39 |
| 14.02 | 6.31 | 52 |
| 14.24 | 6.21 | 36 |
| 14.61 | 6.06 | 20 |
| 14.99 | 5.90 | 16 |
| 16.26 | 5.45 | 15 |
| 17.34 | 5.11 | 100 |
| 18.31 | 4.84 | 90 |
| 18.71 | 4.74 | 44 |
| 19.21 | 4.62 | 50 |
| 19.52 | 4.54 | 31 |
| 21.16 | 4.19 | 13 |
| 22.59 | 3.93 | 84 |
| 23.07 | 3.85 | 15 |
| 23.61 | 3.76 | 14 |
| 25.36 | 3.51 | 35 |
| 25.59 | 3.48 | 55 |
| 26.22 | 3.40 | 19 |
| 27.27 | 3.27 | 25 |
| 27.76 | 3.21 | 26 |
| 28.59 | 3.12 | 13 |
| 29.26 | 3.05 | 18 |
| 30.10 | 2.97 | 11 |

TABLE 1.5

X-ray powder reflections and intensity (normalized) of Mes1 = mesylate, form I

| 2-theta [°] | d [Å] spacing | I/I₀ [%] |
|---|---|---|
| 5.79 | 15.25 | 100 |
| 7.02 | 12.58 | 24 |
| 7.89 | 11.19 | 21 |
| 9.42 | 9.38 | 14 |
| 9.80 | 9.02 | 16 |
| 11.58 | 7.63 | 34 |
| 12.23 | 7.23 | 47 |
| 13.17 | 6.71 | 25 |
| 14.10 | 6.27 | 39 |
| 14.56 | 6.07 | 29 |
| 15.78 | 5.61 | 23 |
| 16.12 | 5.49 | 59 |
| 16.60 | 5.33 | 15 |
| 17.36 | 5.10 | 15 |
| 17.89 | 4.95 | 92 |
| 19.13 | 4.63 | 23 |
| 19.62 | 4.52 | 20 |
| 20.22 | 4.39 | 52 |
| 20.66 | 4.29 | 64 |
| 20.91 | 4.24 | 73 |
| 21.21 | 4.18 | 97 |
| 22.54 | 3.94 | 13 |
| 23.05 | 3.85 | 28 |
| 23.60 | 3.76 | 31 |
| 24.33 | 3.65 | 20 |
| 25.60 | 3.47 | 95 |
| 26.15 | 3.40 | 20 |
| 26.50 | 3.36 | 20 |
| 26.98 | 3.30 | 16 |
| 27.66 | 3.22 | 56 |
| 28.23 | 3.16 | 16 |
| 29.22 | 3.05 | 12 |
| 29.68 | 3.01 | 23 |
| 30.19 | 2.96 | 11 |

TABLE 1.6

X-ray powder reflections and intensity (normalized) of Bes1 = besylate, form I

| 2-theta [°] | d [Å] spacing | I/I₀ [%] |
|---|---|---|
| 3.45 | 25.61 | 33 |
| 8.71 | 10.14 | 9 |
| 9.65 | 9.16 | 9 |
| 11.23 | 7.87 | 10 |
| 11.70 | 7.56 | 11 |
| 12.42 | 7.12 | 10 |
| 13.77 | 6.42 | 60 |
| 14.28 | 6.19 | 45 |
| 15.28 | 5.79 | 14 |
| 15.89 | 5.57 | 11 |

TABLE 1.6-continued

X-ray powder reflections and intensity (normalized) of Bes1 = besylate, form I

| 2-theta [°] | d [Å] spacing | I/I$_0$ [%] |
|---|---|---|
| 17.42 | 5.08 | 55 |
| 18.27 | 4.85 | 62 |
| 18.90 | 4.69 | 72 |
| 19.77 | 4.48 | 15 |
| 20.49 | 4.33 | 41 |
| 21.77 | 4.08 | 12 |
| 22.26 | 3.99 | 100 |
| 22.54 | 3.94 | 33 |
| 22.90 | 3.88 | 32 |
| 23.91 | 3.72 | 15 |
| 24.18 | 3.68 | 18 |
| 24.63 | 3.61 | 14 |
| 24.97 | 3.56 | 11 |
| 25.58 | 3.48 | 54 |
| 26.06 | 3.41 | 32 |
| 26.94 | 3.31 | 28 |
| 27.25 | 3.27 | 21 |
| 27.64 | 3.22 | 15 |
| 27.99 | 3.18 | 11 |
| 28.35 | 3.14 | 16 |
| 28.95 | 3.08 | 11 |
| 29.96 | 2.98 | 14 |
| 30.76 | 2.90 | 10 |

TABLE 1.7a

X-ray powder reflections and intensity (normalized) of Oxa 1, oxalate, form I

| 2-theta [°] | d [Å] spacing | I/I$_0$ [%] |
|---|---|---|
| 9.04 | 9.77 | 43 |
| 9.65 | 9.15 | 24 |
| 12.03 | 7.35 | 19 |
| 12.48 | 7.09 | 76 |
| 14.71 | 6.01 | 69 |
| 15.80 | 5.60 | 18 |
| 16.22 | 5.46 | 56 |
| 17.04 | 5.20 | 33 |
| 18.00 | 4.92 | 83 |
| 18.30 | 4.84 | 56 |
| 19.30 | 4.59 | 61 |
| 20.00 | 4.33 | 36 |
| 20.92 | 4.24 | 76 |
| 21.75 | 4.08 | 100 |
| 23.36 | 3.80 | 46 |
| 23.66 | 3.76 | 32 |
| 23.94 | 3.71 | 38 |
| 25.04 | 3.55 | 24 |
| 25.78 | 3.45 | 46 |
| 27.33 | 3.26 | 29 |
| 28.49 | 3.13 | 21 |
| 29.22 | 3.05 | 16 |

TABLE 1.7b

X-ray powder reflections and intensity (normalized) of Oxa 5, oxalate, form V

| 2-theta [°] | d [Å] spacing | I/I$_0$ [%] |
|---|---|---|
| 6.26 | 14.11 | 9 |
| 9.03 | 9.78 | 11 |
| 9.49 | 9.31 | 15 |
| 11.00 | 8.04 | 12 |
| 12.48 | 7.09 | 34 |
| 12.66 | 6.98 | 22 |
| 14.17 | 6.24 | 15 |
| 14.73 | 6.01 | 11 |
| 15.25 | 5.80 | 3 |
| 15.60 | 5.67 | 27 |
| 16.26 | 5.45 | 11 |
| 17.24 | 5.14 | 16 |
| 17.58 | 5.04 | 28 |
| 18.21 | 4.87 | 100 |
| 18.70 | 4.74 | 19 |
| 19.26 | 4.60 | 13 |
| 20.60 | 4.31 | 12 |
| 20.92 | 4.24 | 10 |
| 21.72 | 4.09 | 11 |
| 22.45 | 3.95 | 16 |
| 23.35 | 3.80 | 27 |
| 23.66 | 3.76 | 34 |
| 25.09 | 3.54 | 13 |
| 25.62 | 3.47 | 20 |
| 26.19 | 3.40 | 24 |
| 26.46 | 3.36 | 21 |
| 27.73 | 3.21 | 16 |
| 28.64 | 3.11 | 9 |
| 30.86 | 2.89 | 8 |

TABLE 1.8

X-ray powder reflections, and intensity (normalized) of Sac 1, sacharinate, form I

| 2-theta [°] | d [Å] spacing | I/I$_0$ [%] |
|---|---|---|
| 5.77 | 15.31 | 17 |
| 7.80 | 11.32 | 11 |
| 8.09 | 10.91 | 13 |
| 8.65 | 10.21 | 20 |
| 8.95 | 9.87 | 13 |
| 9.35 | 9.45 | 17 |
| 9.97 | 8.86 | 17 |
| 11.24 | 7.86 | 64 |
| 11.58 | 7.63 | 21 |
| 12.04 | 7.34 | 36 |
| 12.27 | 7.20 | 25 |
| 12.81 | 6.90 | 52 |
| 13.34 | 6.63 | 58 |
| 14.41 | 6.14 | 23 |
| 14.99 | 5.90 | 85 |
| 15.61 | 5.67 | 64 |
| 16.24 | 5.45 | 20 |
| 16.72 | 5.30 | 85 |
| 17.22 | 5.14 | 100 |
| 17.84 | 4.97 | 22 |
| 18.20 | 4.87 | 18 |
| 18.75 | 4.73 | 30 |
| 19.18 | 4.62 | 64 |
| 20.04 | 4.43 | 44 |
| 20.77 | 4.27 | 24 |
| 21.15 | 4.20 | 28 |
| 21.66 | 4.10 | 15 |
| 22.41 | 3.96 | 22 |
| 22.73 | 3.91 | 26 |
| 23.29 | 3.81 | 28 |
| 23.72 | 3.75 | 52 |
| 24.40 | 3.64 | 62 |
| 25.15 | 3.54 | 37 |
| 25.46 | 3.49 | 24 |
| 25.77 | 3.45 | 23 |
| 26.26 | 3.39 | 22 |
| 26.77 | 3.33 | 55 |
| 27.43 | 3.25 | 18 |
| 28.14 | 3.17 | 21 |
| 28.37 | 3.14 | 29 |
| 28.68 | 3.11 | 24 |
| 29.37 | 3.04 | 16 |

TABLE 1.8-continued

X-ray powder reflections, and intensity (normalized) of Sac 1, sacharinate, form I

| 2-theta [°] | d [Å] spacing | I/I₀ [%] |
|---|---|---|
| 29.79 | 3.00 | 18 |
| 29.97 | 2.98 | 18 |

TABLE 1.9

X-ray powder reflections and intensity (normalized) of Pho1 = phosphate, form I

| 2-theta [°] | d [Å] spacing | I/I₀ [%] |
|---|---|---|
| 5.59 | 15.79 | 100 |
| 6.12 | 14.42 | 18 |
| 6.77 | 13.04 | 36 |
| 7.30 | 12.10 | 17 |
| 7.65 | 11.54 | 15 |
| 8.35 | 10.58 | 16 |
| 9.25 | 9.55 | 24 |
| 10.00 | 8.83 | 24 |
| 10.47 | 8.44 | 17 |
| 10.86 | 8.14 | 20 |
| 11.19 | 7.90 | 60 |
| 11.90 | 7.43 | 28 |
| 11.98 | 7.38 | 22 |
| 12.10 | 7.30 | 35 |
| 13.90 | 6.37 | 28 |
| 14.70 | 6.02 | 28 |
| 15.86 | 5.58 | 22 |
| 16.34 | 5.42 | 23 |
| 16.77 | 5.28 | 27 |
| 17.10 | 5.18 | 40 |
| 17.50 | 5.06 | 89 |
| 18.65 | 4.75 | 26 |
| 19.50 | 4.55 | 27 |
| 19.79 | 4.48 | 29 |
| 20.57 | 4.31 | 37 |
| 21.00 | 4.23 | 27 |
| 21.77 | 4.08 | 6 |
| 22.15 | 4.01 | 32 |
| 22.38 | 3.97 | 38 |
| 23.30 | 3.81 | 36 |
| 23.68 | 3.75 | 54 |
| 23.89 | 3.72 | 35 |
| 24.54 | 3.62 | 26 |
| 25.03 | 3.55 | 16 |
| 25.36 | 3.51 | 27 |
| 25.88 | 3.44 | 20 |
| 26.84 | 3.32 | 14 |
| 27.36 | 3.26 | 15 |
| 27.89 | 3.19 | 18 |
| 28.16 | 3.17 | 22 |
| 28.50 | 3.13 | 20 |
| 29.18 | 3.06 | 13 |
| 30.37 | 2.93 | 14 |

TABLE 1.10a

X-ray powder reflections and intensity (normalized) of Mae 1, maleate form I

| 2-theta [°] | d [Å] spacing | I/I₀ [%] |
|---|---|---|
| 8.51 | 10.38 | 10 |
| 9.22 | 9.58 | 84 |
| 11.47 | 7.71 | 84 |
| 13.83 | 6.40 | 12 |
| 14.44 | 6.13 | 100 |
| 14.92 | 5.93 | 94 |
| 15.60 | 5.68 | 17 |
| 15.87 | 5.58 | 26 |
| 16.22 | 5.46 | 63 |
| 16.84 | 5.26 | 47 |
| 17.36 | 5.10 | 38 |
| 17.77 | 4.99 | 21 |
| 18.51 | 4.79 | 27 |
| 18.68 | 4.75 | 48 |
| 19.19 | 4.62 | 70 |
| 20.54 | 4.32 | 10 |
| 21.12 | 4.20 | 20 |
| 22.65 | 3.92 | 13 |
| 23.08 | 3.85 | 21 |
| 23.54 | 3.78 | 45 |
| 24.67 | 3.61 | 58 |
| 25.95 | 3.43 | 18 |
| 26.77 | 3.33 | 11 |
| 27.83 | 3.20 | 21 |
| 28.81 | 3.10 | 10 |
| 29.39 | 3.04 | 17 |
| 29.76 | 3.00 | 24 |
| 30.64 | 2.92 | 14 |
| 31.48 | 2.84 | 27 |

TABLE 1.10b

X-ray powder reflections and intensity (normalized) of Mae 3, maleate, form III

| 2-theta [°] | d [Å] spacing | I/I₀ [%] |
|---|---|---|
| 6.56 | 13.46 | 39 |
| 8.56 | 10.32 | 13 |
| 9.99 | 8.84 | 24 |
| 11.28 | 7.84 | 13 |
| 12.22 | 7.23 | 32 |
| 13.10 | 6.75 | 26 |
| 13.85 | 6.38 | 44 |
| 14.58 | 6.07 | 52 |
| 16.20 | 5.47 | 16 |
| 16.76 | 5.28 | 45 |
| 17.16 | 5.16 | 100 |
| 17.46 | 5.07 | 31 |
| 18.50 | 4.79 | 18 |
| 19.24 | 4.61 | 18 |
| 19.62 | 4.52 | 91 |
| 20.08 | 4.42 | 43 |
| 20.41 | 4.35 | 27 |
| 21.00 | 4.22 | 9 |
| 21.65 | 4.10 | 58 |
| 22.23 | 4.00 | 42 |
| 22.73 | 3.91 | 21 |
| 22.90 | 3.88 | 22 |
| 23.27 | 3.82 | 40 |
| 23.90 | 3.72 | 39 |
| 24.28 | 3.66 | 40 |
| 24.86 | 3.58 | 10 |
| 25.30 | 3.52 | 41 |
| 25.66 | 3.47 | 27 |
| 26.57 | 3.35 | 23 |
| 27.14 | 3.28 | 38 |
| 27.82 | 3.20 | 64 |
| 28.55 | 3.12 | 17 |
| 29.14 | 3.06 | 14 |
| 29.48 | 3.03 | 19 |
| 29.70 | 3.00 | 13 |
| 30.73 | 2.91 | 35 |

TABLE 1.11

X-ray powder reflections and intensity (normalized) of Ets 1, ethanesulfonate, form I

| 2-theta [°] | d [Å] spacing | $I/I_0$ [%] |
|---|---|---|
| 5.77 | 15.30 | 62 |
| 6.97 | 12.66 | 14 |
| 7.82 | 11.29 | 15 |
| 9.70 | 9.11 | 10 |
| 11.55 | 7.65 | 29 |
| 12.19 | 7.25 | 40 |
| 13.04 | 6.78 | 17 |
| 14.16 | 6.25 | 31 |
| 14.42 | 6.14 | 14 |
| 15.69 | 5.64 | 21 |
| 15.97 | 5.54 | 33 |
| 16.46 | 5.38 | 9 |
| 16.80 | 5.27 | 9 |
| 17.18 | 5.16 | 13 |
| 17.70 | 5.00 | 56 |
| 17.94 | 4.94 | 20 |
| 18.97 | 4.67 | 21 |
| 19.45 | 4.56 | 15 |
| 20.06 | 4.42 | 32 |
| 20.46 | 4.34 | 52 |
| 20.98 | 4.23 | 100 |
| 21.54 | 4.12 | 15 |
| 22.83 | 3.89 | 12 |
| 23.38 | 3.80 | 26 |
| 24.06 | 3.69 | 18 |
| 25.18 | 3.53 | 27 |
| 25.61 | 3.47 | 37 |
| 26.00 | 3.42 | 21 |
| 26.34 | 3.38 | 12 |
| 26.85 | 3.31 | 11 |
| 27.78 | 3.21 | 37 |
| 28.34 | 3.15 | 9 |

TABLE 1.12

X-ray powder reflections and intensity (normalized) of Cas1 = camphorsulfonate, form I

| 2-theta [°] | d [Å] spacing | $I/I_0$ [%] |
|---|---|---|
| 5.41 | 16.32 | 100 |
| 9.60 | 9.20 | 9 |
| 10.07 | 8.77 | 10 |
| 10.79 | 8.19 | 14 |
| 11.38 | 7.77 | 7 |
| 12.26 | 7.21 | 11 |
| 12.34 | 7.17 | 12 |
| 13.15 | 6.72 | 8 |
| 13.86 | 6.38 | 12 |
| 14.10 | 6.27 | 21 |
| 15.55 | 5.69 | 30 |
| 16.10 | 5.50 | 45 |
| 16.25 | 5.45 | 52 |
| 16.62 | 5.33 | 11 |
| 16.79 | 5.29 | 11 |
| 17.59 | 5.04 | 15 |
| 17.79 | 4.98 | 20 |
| 18.65 | 4.75 | 18 |
| 19.32 | 4.59 | 19 |
| 20.21 | 4.39 | 19 |
| 20.96 | 4.23 | 10 |
| 21.49 | 4.13 | 18 |
| 21.73 | 4.08 | 17 |
| 22.50 | 3.95 | 17 |
| 23.06 | 3.85 | 17 |
| 23.58 | 3.78 | 17 |
| 23.95 | 3.71 | 16 |
| 24.55 | 3.62 | 24 |
| 25.07 | 3.55 | 13 |
| 28.65 | 3.11 | 9 |
| 29.10 | 3.07 | 7 |
| 29.18 | 3.06 | 6 |

TABLE 1.13

X-ray powder reflections and intensity (normalized) of Mao 1, malonate, form I

| 2-theta [°] | d [Å] spacing | $I/I_0$ [%] |
|---|---|---|
| 3.80 | 23.23 | 99 |
| 7.63 | 11.57 | 37 |
| 7.93 | 11.13 | 45 |
| 10.32 | 8.56 | 60 |
| 13.06 | 6.77 | 61 |
| 13.36 | 6.62 | 43 |
| 13.91 | 6.36 | 35 |
| 14.49 | 6.1 | 57 |
| 15.21 | 5.82 | 37 |
| 15.89 | 5.57 | 42 |
| 16.78 | 5.28 | 57 |
| 17.96 | 4.93 | 39 |
| 19.18 | 4.62 | 60 |
| 20.34 | 4.36 | 49 |
| 20.74 | 4.28 | 32 |
| 21.20 | 4.19 | 100 |
| 21.69 | 4.09 | 31 |
| 22.27 | 3.99 | 45 |
| 22.86 | 3.89 | 47 |
| 23.34 | 3.81 | 47 |
| 23.90 | 3.72 | 68 |
| 24.71 | 3.60 | 65 |
| 25.65 | 3.47 | 50 |
| 26.35 | 3.38 | 26 |
| 26.84 | 3.32 | 28 |
| 26.94 | 3.31 | 27 |
| 27.86 | 3.20 | 24 |
| 28.38 | 3.14 | 23 |
| 28.94 | 3.08 | 21 |
| 29.10 | 3.06 | 22 |
| 29.18 | 3.06 | 21 |
| 30.30 | 2.95 | 28 |

TABLE 1.14

X-ray powder reflections and intensity (normalized) of L-Tar 1, L-tartrate, form I

| 2-theta [°] | d [Å] spacing | $I/I_0$ [%] |
|---|---|---|
| 10.04 | 8.80 | 15 |
| 10.55 | 8.37 | 23 |
| 11.82 | 7.48 | 13 |
| 13.10 | 6.75 | 12 |
| 15.32 | 5.77 | 34 |
| 15.94 | 5.55 | 20 |
| 16.22 | 5.46 | 59 |
| 17.17 | 5.16 | 11 |
| 17.92 | 4.94 | 67 |
| 18.55 | 4.78 | 44 |
| 19.05 | 4.65 | 30 |
| 19.61 | 4.52 | 17 |
| 20.18 | 4.40 | 14 |
| 20.64 | 4.30 | 73 |
| 21.23 | 4.18 | 45 |
| 21.74 | 4.08 | 99 |
| 23.08 | 3.85 | 17 |
| 23.76 | 3.74 | 100 |
| 24.31 | 3.66 | 9 |
| 25.23 | 3.53 | 28 |

TABLE 1.14-continued

X-ray powder reflections and intensity (normalized) of L-Tar 1, L-tartrate, form I

| 2-theta [°] | d [Å] spacing | I/I$_0$ [%] |
|---|---|---|
| 25.88 | 3.44 | 17 |
| 26.46 | 3.36 | 11 |
| 27.27 | 3.27 | 42 |
| 27.55 | 3.23 | 23 |
| 28.29 | 3.15 | 12 |
| 28.76 | 3.10 | 9 |
| 29.08 | 3.07 | 11 |
| 30.46 | 2.93 | 13 |
| 30.87 | 2.89 | 15 |

TABLE 1.15a

X-ray powder reflections and intensity (normalized) of Fum 1, fumarate, form I

| 2-theta [°] | d [Å] spacing | I/I$_0$ [%] |
|---|---|---|
| 8.51 | 10.38 | 18 |
| 9.13 | 9.68 | 31 |
| 10.35 | 8.54 | 37 |
| 11.11 | 7.95 | 12 |
| 11.39 | 7.76 | 13 |
| 12.07 | 7.32 | 20 |
| 13.87 | 6.38 | 39 |
| 14.54 | 6.08 | 23 |
| 15.30 | 5.79 | 35 |
| 15.57 | 5.68 | 28 |
| 16.15 | 5.48 | 23 |
| 17.07 | 5.19 | 42 |
| 17.75 | 4.99 | 22 |
| 18.19 | 4.87 | 61 |
| 18.53 | 4.78 | 20 |
| 18.76 | 4.72 | 28 |
| 19.78 | 4.48 | 2 |
| 20.77 | 4.27 | 34 |
| 21.44 | 4.14 | 13 |
| 21.92 | 4.05 | 23 |
| 22.92 | 3.88 | 24 |
| 23.91 | 3.72 | 100 |
| 24.27 | 3.66 | 33 |
| 24.69 | 3.60 | 21 |
| 25.24 | 3.52 | 14 |
| 25.77 | 3.45 | 45 |
| 26.24 | 3.39 | 14 |
| 27.17 | 3.28 | 18 |
| 27.71 | 3.22 | 10 |

TABLE 1.15b

X-ray powder reflections and intensity (normalized) of Fum 2, fumerate, form II

| 2-theta [°] | d [Å] spacing | I/I$_0$ [%] |
|---|---|---|
| 10.20 | 8.66 | 30 |
| 10.84 | 8.15 | 18 |
| 11.89 | 7.43 | 25 |
| 13.29 | 6.66 | 16 |
| 15.19 | 5.83 | 40 |
| 15.81 | 5.60 | 14 |
| 16.32 | 5.42 | 64 |
| 18.07 | 4.90 | 36 |
| 18.74 | 4.73 | 87 |
| 19.17 | 4.63 | 18 |
| 19.41 | 4.57 | 15 |
| 19.94 | 4.45 | 15 |
| 20.13 | 4.41 | 15 |
| 20.53 | 4.32 | 25 |
| 20.90 | 4.25 | 49 |
| 21.54 | 4.12 | 40 |
| 21.85 | 4.06 | 85 |
| 23.07 | 3.85 | 14 |
| 23.92 | 3.72 | 100 |
| 25.39 | 3.50 | 36 |
| 27.41 | 3.25 | 39 |
| 27.78 | 3.21 | 17 |
| 28.76 | 3.10 | 12 |
| 29.23 | 3.05 | 14 |
| 30.99 | 2.88 | 12 |
| 32.95 | 2.72 | 15 |
| 33.80 | 2.65 | 11 |
| 36.61 | 2.45 | 12 |
| 39.21 | 2.29 | 10 |

TABLE 1.16

X-ray powder reflections and intensity (normalized) of Gly1 = glycolate, form I

| 2-theta [°] | d [Å] spacing | I/I$_0$ [%] |
|---|---|---|
| 4.75 | 18.58 | 13 |
| 5.26 | 16.79 | 13 |
| 5.98 | 14.76 | 35 |
| 7.42 | 11.91 | 20 |
| 10.49 | 8.43 | 87 |
| 11.55 | 7.65 | 23 |
| 12.02 | 7.35 | 27 |
| 13.17 | 6.71 | 14 |
| 13.72 | 6.45 | 26 |
| 14.62 | 6.05 | 19 |
| 15.38 | 5.75 | 20 |
| 16.12 | 5.49 | 25 |
| 17.11 | 5.18 | 36 |
| 17.62 | 5.03 | 54 |
| 17.92 | 4.94 | 31 |
| 18.44 | 4.81 | 29 |
| 19.07 | 4.65 | 25 |
| 19.38 | 4.57 | 23 |
| 19.78 | 4.48 | 93 |
| 20.82 | 4.26 | 22 |
| 21.09 | 4.21 | 27 |
| 21.90 | 4.05 | 34 |
| 22.41 | 3.96 | 100 |
| 22.59 | 3.93 | 91 |
| 23.21 | 3.83 | 18 |
| 23.76 | 3.74 | 71 |
| 24.18 | 3.68 | 24 |
| 24.26 | 3.66 | 24 |
| 24.53 | 3.62 | 28 |
| 24.90 | 3.57 | 19 |
| 25.40 | 3.50 | 21 |
| 25.83 | 3.45 | 17 |
| 26.64 | 3.34 | 17 |
| 27.27 | 3.27 | 14 |
| 27.71 | 3.22 | 22 |
| 28.06 | 3.18 | 15 |
| 28.34 | 3.15 | 17 |
| 28.69 | 3.11 | 14 |
| 29.48 | 3.03 | 8 |
| 29.98 | 2.98 | 16 |
| 30.36 | 2.94 | 20 |

TABLE 1.17

X-ray powder reflections and intensity (normalized) of Cit 1, citrate, form I

| 2-theta [°] | d [Å] spacing | I/I$_0$ [%] |
|---|---|---|
| 5.66 | 15.61 | 100 |
| 6.64 | 13.29 | 18 |
| 8.93 | 9.89 | 8 |
| 11.31 | 7.81 | 26 |
| 11.83 | 7.47 | 25 |
| 13.50 | 6.55 | 6 |
| 13.86 | 6.38 | 7 |
| 14.65 | 6.04 | 9 |
| 16.58 | 5.34 | 27 |
| 16.95 | 5.22 | 10 |
| 17.61 | 5.03 | 9 |
| 18.21 | 4.87 | 52 |
| 18.95 | 4.68 | 18 |
| 19.26 | 4.60 | 7 |
| 20.87 | 4.25 | 15 |
| 21.70 | 4.09 | 19 |
| 22.75 | 3.90 | 7 |
| 23.06 | 3.85 | 6 |
| 23.88 | 3.72 | 8 |
| 24.28 | 3.66 | 10 |
| 24.61 | 3.61 | 13 |
| 25.07 | 3.54 | 7 |
| 25.82 | 3.45 | 5 |
| 26.26 | 3.39 | 6 |
| 27.00 | 3.30 | 13 |
| 27.75 | 3.21 | 8 |
| 28.05 | 3.18 | 7 |
| 28.55 | 3.12 | 7 |
| 29.38 | 3.04 | 6 |

TABLE 1.18

X-ray powder reflections and intensity (normalized) of Man 1, mandelate, form I

| 2-theta [°] | d [Å] spacing | I/I$_0$ [%] |
|---|---|---|
| 7.42 | 11.90 | 9 |
| 8.35 | 10.57 | 29 |
| 10.57 | 8.36 | 26 |
| 12.00 | 7.36 | 16 |
| 12.32 | 7.17 | 10 |
| 14.08 | 6.28 | 30 |
| 14.74 | 6.00 | 15 |
| 15.29 | 5.79 | 11 |
| 15.69 | 5.64 | 32 |
| 16.34 | 5.42 | 14 |
| 16.67 | 5.31 | 11 |
| 17.34 | 5.11 | 13 |
| 18.19 | 4.87 | 100 |
| 18.56 | 4.78 | 18 |
| 19.01 | 4.66 | 63 |
| 19.69 | 4.50 | 23 |
| 20.08 | 4.42 | 31 |
| 21.05 | 4.22 | 12 |
| 21.41 | 4.14 | 26 |
| 21.66 | 4.10 | 36 |
| 22.08 | 4.02 | 21 |
| 22.89 | 3.88 | 37 |
| 23.54 | 3.77 | 28 |
| 23.86 | 3.73 | 41 |
| 24.41 | 3.64 | 23 |
| 24.81 | 3.58 | 10 |
| 25.23 | 3.53 | 14 |
| 26.09 | 3.41 | 4 |
| 26.47 | 3.36 | 12 |

TABLE 1.19

X-ray powder reflections and intensity (normalized) of L-Mal 1, malate, form I

| 2-theta [°] | d [Å] spacing | I/I$_0$ [%] |
|---|---|---|
| 8.40 | 10.51 | 9 |
| 11.30 | 7.82 | 71 |
| 11.69 | 7.56 | 12 |
| 12.49 | 7.08 | 11 |
| 12.75 | 6.94 | 10 |
| 13.38 | 6.61 | 10 |
| 13.68 | 6.47 | 10 |
| 14.49 | 6.10 | 59 |
| 14.80 | 5.98 | 16 |
| 15.09 | 5.87 | 32 |
| 15.78 | 5.61 | 28 |
| 16.96 | 5.22 | 47 |
| 17.89 | 4.95 | 48 |
| 18.27 | 4.85 | 36 |
| 18.90 | 4.69 | 12 |
| 19.63 | 4.52 | 38 |
| 20.48 | 4.33 | 9 |
| 21.36 | 4.15 | 24 |
| 21.98 | 4.04 | 11 |
| 22.69 | 3.91 | 32 |
| 23.46 | 3.79 | 100 |
| 23.91 | 3.72 | 62 |
| 24.19 | 3.68 | 24 |
| 24.23 | 3.67 | 26 |
| 24.91 | 3.57 | 35 |
| 25.38 | 3.50 | 19 |
| 26.14 | 3.41 | 12 |
| 26.64 | 3.34 | 27 |
| 27.33 | 3.26 | 9 |

TABLE 1.20

X-ray powder reflections and intensity (normalized) of Nas1 = naphtalene-sulfonate, form I

| 2-theta [°] | d [Å] spacing | I/I$_0$ [%] |
|---|---|---|
| 3.17 | 27.83 | 17 |
| 12.71 | 6.95 | 11 |
| 12.93 | 6.84 | 9 |
| 13.97 | 6.33 | 25 |
| 14.14 | 6.26 | 24 |
| 14.44 | 6.13 | 20 |
| 14.83 | 5.96 | 20 |
| 15.06 | 5.88 | 11 |
| 15.89 | 5.57 | 40 |
| 17.64 | 5.02 | 46 |
| 18.02 | 4.92 | 100 |
| 18.33 | 4.83 | 29 |
| 19.05 | 4.65 | 43 |
| 19.43 | 4.56 | 31 |
| 20.51 | 4.32 | 14 |
| 21.69 | 4.09 | 11 |
| 22.17 | 4.00 | 59 |
| 22.41 | 3.96 | 53 |
| 23.22 | 3.83 | 25 |
| 23.99 | 3.70 | 9 |
| 25.58 | 3.48 | 13 |
| 25.88 | 3.43 | 63 |
| 26.57 | 3.35 | 11 |
| 26.80 | 3.32 | 12 |
| 27.07 | 3.29 | 25 |
| 27.37 | 3.25 | 27 |
| 28.18 | 3.16 | 16 |
| 29.01 | 3.07 | 7 |
| 29.64 | 3.01 | 10 |
| 29.95 | 2.98 | 10 |
| 30.47 | 2.93 | 8 |
| 31.57 | 2.83 | 10 |
| 33.33 | 2.69 | 8 |

TABLE 1.20-continued

X-ray powder reflections and intensity (normalized) of Nas1 = naphtalene-sulfonate, form I

| 2-theta [°] | d [Å] spacing | I/I$_0$ [%] |
|---|---|---|
| 35.92 | 2.50 | 10 |
| 36.96 | 2.43 | 8 |

TABLE 1.21

X-ray powder reflections and intensity (normalized) of Tos 2, tosylate, form II

| 2-theta [°] | d [Å] spacing | I/I$_0$ [%] |
|---|---|---|
| 4.89 | 18.04 | 20 |
| 6.29 | 14.03 | 6 |
| 7.91 | 11.16 | 5 |
| 10.59 | 8.35 | 13 |
| 12.64 | 7.00 | 8 |
| 12.89 | 6.86 | 10 |
| 13.78 | 6.42 | 4 |
| 14.75 | 6.00 | 4 |
| 15.43 | 5.74 | 20 |
| 15.76 | 5.62 | 4 |
| 16.79 | 5.28 | 5 |
| 17.21 | 5.15 | 7 |
| 17.96 | 4.94 | 100 |
| 18.73 | 4.73 | 10 |
| 19.01 | 4.67 | 4 |
| 19.39 | 4.57 | 24 |
| 19.97 | 4.44 | 11 |
| 20.53 | 4.32 | 47 |
| 20.85 | 4.26 | 10 |
| 21.27 | 4.17 | 4 |
| 21.77 | 4.08 | 6 |
| 22.10 | 4.02 | 6 |
| 22.76 | 3.90 | 3 |
| 23.07 | 3.85 | 3 |
| 23.97 | 3.71 | 11 |
| 24.48 | 3.63 | 6 |
| 24.91 | 3.57 | 4 |
| 25.19 | 3.53 | 21 |
| 25.95 | 3.43 | 4 |
| 26.61 | 3.35 | 43 |

TABLE 1.22

X-ray powder reflections and intensity (normalized) of Tos 2, fumarate, form III

| 2-theta [°] | d [Å] spacing | I/I$_0$ [%] |
|---|---|---|
| 9.64 | 9.17 | 68 |
| 10.65 | 8.30 | 3 |
| 11.53 | 7.67 | 5 |
| 12.41 | 7.13 | 3 |
| 14.39 | 6.15 | 19 |
| 15.15 | 5.84 | 30 |
| 15.87 | 5.58 | 26 |
| 16.61 | 5.33 | 92 |
| 17.01 | 5.21 | 96 |
| 17.83 | 4.97 | 44 |
| 18.84 | 4.71 | 66 |
| 19.37 | 4.58 | 18 |
| 19.59 | 4.53 | 80 |
| 19.89 | 4.46 | 77 |
| 20.33 | 4.36 | 33 |
| 20.79 | 4.27 | 14 |
| 21.55 | 4.12 | 86 |
| 21.97 | 4.04 | 19 |
| 22.82 | 3.89 | 7 |

TABLE 1.22-continued

X-ray powder reflections and intensity (normalized) of Tos 2, fumarate, form III

| 2-theta [°] | d [Å] spacing | I/I$_0$ [%] |
|---|---|---|
| 23.55 | 3.78 | 26 |
| 24.07 | 3.69 | 100 |
| 24.49 | 3.63 | 17 |
| 25.03 | 3.55 | 28 |
| 27.40 | 3.25 | 14 |
| 28.11 | 3.17 | 18 |
| 28.37 | 3.14 | 11 |

TABLE 1.23

X-ray powder reflections and intensity (normalized) of Cas 2, camphorsulfonate, form II

| 2-theta [°] | d [Å] spacing | I/I$_0$ [%] |
|---|---|---|
| 5.27 | 16.75 | 29 |
| 6.69 | 13.20 | 10 |
| 7.01 | 12.61 | 12 |
| 8.09 | 10.92 | 9 |
| 9.63 | 9.18 | 15 |
| 10.03 | 8.81 | 6 |
| 10.57 | 8.36 | 8 |
| 12.27 | 7.21 | 19 |
| 14.08 | 6.29 | 28 |
| 14.48 | 6.11 | 26 |
| 15.04 | 5.89 | 11 |
| 15.55 | 5.69 | 15 |
| 16.18 | 5.47 | 100 |
| 16.29 | 5.44 | 99 |
| 17.23 | 5.14 | 16 |
| 17.62 | 5.03 | 14 |
| 17.74 | 4.99 | 10 |
| 18.63 | 4.76 | 53 |
| 19.21 | 4.62 | 12 |
| 19.48 | 4.55 | 12 |
| 19.88 | 4.46 | 45 |
| 20.05 | 4.42 | 28 |
| 20.44 | 4.34 | 22 |
| 20.56 | 4.32 | 20 |
| 21.27 | 4.17 | 37 |
| 22.12 | 4.01 | 17 |
| 23.32 | 3.81 | 22 |
| 24.03 | 3.70 | 35 |
| 24.63 | 3.61 | 30 |
| 25.25 | 3.52 | 11 |

TABLE 1.24

X-ray powder reflections and intensity (normalized) of Gly 2, glycolate, form II

| 2-theta [°] | d [Å] spacing | I/I$_0$ [%] |
|---|---|---|
| 9.98 | 8.86 | 12 |
| 10.47 | 8.44 | 13 |
| 10.98 | 8.05 | 7 |
| 11.25 | 7.86 | 5 |
| 11.62 | 7.61 | 15 |
| 12.65 | 7.00 | 14 |
| 13.05 | 6.78 | 30 |
| 13.85 | 6.39 | 9 |
| 14.18 | 6.24 | 4 |
| 14.57 | 6.07 | 4 |
| 15.40 | 5.75 | 40 |
| 15.59 | 5.68 | 24 |
| 16.03 | 5.53 | 11 |
| 16.19 | 5.47 | 13 |

TABLE 1.24-continued

X-ray powder reflections and intensity (normalized) of Gly 2, glycolate,, form II

| 2-theta [°] | d [Å] spacing | I/I$_0$ [%] |
|---|---|---|
| 16.61 | 5.33 | 5 |
| 17.30 | 5.12 | 18 |
| 17.73 | 5.00 | 13 |
| 18.11 | 4.89 | 8 |
| 18.38 | 4.82 | 15 |
| 18.67 | 4.75 | 13 |
| 19.10 | 4.64 | 34 |
| 19.77 | 4.49 | 21 |
| 20.02 | 4.43 | 31 |
| 20.34 | 4.36 | 22 |
| 21.12 | 4.20 | 15 |
| 21.61 | 4.11 | 18 |
| 22.09 | 4.02 | 100 |
| 22.38 | 3.97 | 78 |
| 23.21 | 3.83 | 15 |
| 23.56 | 3.77 | 13 |

The single crystal data and structure refinement for the crystalline salt forms in accordance with the present invention are displayed in the preceding tables 2.1 to 2.18. The abbreviations used in those tables nave the following meanings:

Fw=formula weight;
T=Temperature of data collection;
λ=wavelength of X-ray source;
$D_m$=calculated density;
θ range=Theta range of data collection;
S=Goodness-o-fit on $F^2$;
R[I>2σ(I)]=Final R Indices [I>2sigma(I)]

TABLE 2.1

Single crystal data and structure refinement of bromide form III

| Empirical formula | $C_{20}H_{22}F_3N_4O^+$•Br$^-$•0.5 $H_2O$•0.5 $CH_3OH$ |
|---|---|
| Fw | 496.35 |
| T [K] | 120(2) |
| λ[Å] | 0.71073 |
| Crystal system | Monoclinic |
| Space group | P 2$_1$/c |
| Unit cell dimensions | |
| a [Å] | 6.9150(3) |
| b [Å] | 30.801(2) |
| c [Å] | 20.4990(8) |
| α [°] | 90 |
| β [°] | 95.728(2) |
| γ [°] | 90 |
| V [Å$^3$] | 4344.3 (3)(1) |
| Z | 4 |
| $D_m$ [g/cm$^3$] | 1.518 |
| F(000) | 2032 |
| Crystal size [mm$^3$] | 0.30 × 0.20 × 0.06 |
| θ range [°] | 2 → 27.5 |
| Reflections collected | 9029 |
| Independent reflections | 6180 [R$_{int}$ = 0.0424] |
| S | 1.15 |
| R [I > 2σ(I)] | R1 = 0.0605, wR2 = 0.1329 |
| R indices (all data) | R1 = 0.0766, wR2 = 0.1423 |

TABLE 2.2

Single crystal data and structure refinement of oxalate form I

| Empirical formula | $C_{20}H_{22}F_3N_4O^+$•$C_2HO_4^-$ |
|---|---|
| Fw | 480.44 |

TABLE 2.2-continued

Single crystal data and structure refinement of oxalate form I

| T [K] | 293(2) |
|---|---|
| λ[Å] | 0.71073 Å |
| Crystal system | Orthorhombic |
| Space group | P 2$_1$2$_1$2$_1$ |
| Unit cell dimensions | |
| a [Å] | 10.3900(4) |
| b [Å] | 11.3420(4) |
| c [Å] | 19.3230(6) |
| α [°] | 90 |
| β [°] | 90 |
| γ [°] | 90 |
| V [Å$^3$] | 2277.1(2) |
| Z | 4 |
| $D_m$ [g/cm$^3$] | 1.401 |
| F(000) | 1000 |
| Crystal size [mm$^3$] | 0.3 × 0.25 × 0.2 |
| θ range [°] | 3 → 27.5 |
| Reflections collected | 14241 |
| Independent reflections | 5179 [R$_{int}$ = 0.0243] |
| S | 1.058 |
| R [I > 2σ(I)] | R1 = 0.0379, wR2 = 0.0808 |
| R indices (all data) | R1 = 0.0465, wR2 = 0.0856 |

TABLE 2.3

Single crystal data and structure refinement of oxalate form V

| Empirical formula | $C_{20}H_{22}F_3N_4O^+$•0.5 $C_2O_4^{2-}$•$H_2O$ |
|---|---|
| Fw | 453.44 |
| T [K] | 120(2) |
| λ[Å] | 0.71073 |
| Crystal system | Monoclinic |
| Space group | P 2$_1$/c |
| Unit cell dimensions | |
| a [Å] | 7.6030(3) |
| b [Å] | 28.5050(10) |
| c [Å] | 10.6200(4) |
| α [°] | 90 |
| β [°] | 113.346(2) |
| γ [°] | 90 |
| V [Å$^3$] | 2113.17(14) |
| Z | 4 |
| $D_m$ [g/cm$^3$] | 1.425 |
| F(000) | 948 |
| Crystal size [mm$^3$] | 0.2 × 0.15 × 0.1 |
| θ range [°] | 1.5 → 24. |
| Reflections collected | 10041 |
| Independent reflections | 3302 [R$_{int}$ = 0.0791] |
| S | 4.655 |
| R [I > 2σ(I)] | R1 = 0.2415, wR2 = 0.5590 |
| R indices (all data) | R1 = 0.2468, wR2 = 0.5629 |

TABLE 2.4

Single crystal data and structure refinement of sacharinate form I

| Empirical formula | $C_{20}H_{22}F_3N_4O^+$•$C_7H_4NSO_3^-$•1.5 $H_2O$ |
|---|---|
| Fw | 600.61 |
| T [K] | 293(2) |
| λ[Å] | 0.71073 |
| Crystal system | Triclinic |
| Space group | P −1 |
| Unit cell dimensions | |
| a [Å] | 8.1930(2) |
| b [Å] | 11.7200(2) |
| c [Å] | 30.7140(7) |
| α [°] | 93.206(1) |
| β [°] | 92.430(1) |
| γ [°] | 103.257(1) |
| V [Å$^3$] | 2861.5(2) |

TABLE 2.4-continued

Single crystal data and structure refinement of sacharinate form I

| | |
|---|---|
| Z | 4 |
| $D_m$ [g/cm$^3$] | 1.394 |
| F(000) | 1252 |
| Crystal size [mm$^3$] | 0.4 × 0.35 × 0.2 |
| θ range [°] | 2 → 25.5 |
| Reflections collected | 15887 |
| Independent reflections | 10288 [$R_{int}$ = 0.0372] |
| S | 1.078 |
| R [I > 2σ(I)] | R1 = 0.0686, wR2 = 0.1316 |
| R indices (all data) | R1 = 0.1218, wR2 = 0.1551 |

TABLE 2.5

Single crystal data and structure refinement of maleate form I

| | |
|---|---|
| Empirical formula | $C_{20}H_{22}F_3N_4O^+ \cdot C_4H_3O_4^- \cdot C_4H_8O$ |
| Fw | 578.58 |
| T [K] | 293(2) |
| λ[Å] | 0.71073 |
| Crystal system | Orthorhombic |
| Space group | Pbca |
| Unit cell dimensions | |
| a [Å] | 19.9300(1) |
| b [Å] | 12.2540(2) |
| c [Å] | 24.2320(3) |
| α [°] | 90 |
| β [°] | 90 |
| γ [°] | 90 |
| V [Å$^3$] | 5917.99(12) |
| Z | 8 |
| $D_m$ [g/cm$^3$] | 1.299 |
| F(000) | 2432 |
| Crystal size [mm$^3$] | 0.3 × 0.2 × 0.1 |
| θ range [°] | 1.7 → 25 |
| Reflections collected | 35074 |
| Independent reflections | 5199 [$R_{int}$ = 0.0461] |
| S | 1.107 |
| R [I > 2σ(I)] | R1 = 0.0625, wR2 = 0.1701 |
| R indices (all data) | R1 = 0.0808, wR2 = 0.1901 |

TABLE 2.6

Single crystal data and structure refinement of maleate form III

| | |
|---|---|
| Empirical formula | $C_{20}H_{22}F_3N_4O^+ \cdot C_4H_3O_4$ |
| Fw | 506.48 |
| T [K] | 293(2) K |
| λ[Å] | 0.71073 |
| Crystal system | Monoclinic |
| Space group | C 2/c |
| Unit cell dimensions | |
| a [Å] | 27.2820(5) |
| b [Å] | 8.1960(2) |
| c [Å] | 20.8440(4) |
| α [°] | 90 |
| β [°] | 98.295(1) |
| γ [°] | 90 |
| V [Å$^3$] | 4612.03(13) |
| Z | 8 |
| $D_m$ [g/cm$^3$] | 1.459 |
| F(000) | 2112 |
| Crystal size [mm$^3$] | 0.35 × 0.2 × 0.1 |
| θ range [°] | 2.5 → 30 |
| Reflections collected | 11604 |
| Independent reflections | 6688 [$R_{int}$ = 0.0242] |
| S | 1.023 |
| R [I > 2σ(I)] | R1 = 0.0504, wR2 = 0.1108 |
| R indices (all data) | R1 = 0.0680, wR2 = 0.1219 |

TABLE 2.7

Single crystal data and structure refinement of ethanesulfonate form I

| | |
|---|---|
| Empirical formula | $C_{20}H_{22}F_3N_4O^+ \cdot C_2H_5SO_3^- \cdot H_2O$ |
| Fw | 518.55 |
| T [K] | 293(2) K |
| λ[Å] | 0.71073 |
| Crystal system | Monoclinic |
| Space group | P 2$_1$/c |
| Unit cell dimensions | |
| a [Å] | 15.3580(2) |
| b [Å] | 22.6680(7) |
| c [Å] | 7.0870(6) |
| α [°] | 90 |
| β [°] | 91.595(2) |
| γ [°] | 90 |
| V [Å$^3$] | 2466.3(2) |
| Z | 4 |
| $D_m$ [g/cm$^3$] | 1.397 Mg/m$^3$ |
| F(000) | 1088 |
| Crystal size [mm$^3$] | 0.3 × 0.2 × 0.2 |
| θ range [°] | 2 → 26 |
| Reflections collected | 11237 |
| Independent reflections | 4736 [$R_{int}$ = 0.0409] |
| S | 1.033 |
| R [I > 2σ(I)] | R1 = 0.0598, wR2 = 0.1222 |
| R indices (all data) | R1 = 0.0935, wR2 = 0.1389 |

TABLE 2.8

Single crystal data and structure refinement of malonate form I

| | |
|---|---|
| Empirical formula | $C_{20}H_{22}F_3N_4O^+ \cdot C_3H_3O_4^- \cdot 2H_2O$ |
| Fw | 530.50 |
| T [K] | 293(2) |
| λ[Å] | 0.71073 |
| Crystal system | Monoclinic |
| Space group | P 2$_1$/c |
| Unit cell dimensions | |
| a [Å] | 23.2150(2) |
| b [Å] | 12.7050(2) |
| c [Å] | 8.3990(4) |
| α [°] | 90 |
| β [°] | 92.422(1) |
| γ [°] | 90 |
| V [Å$^3$] | 2475.0(2) |
| Z | 4 |
| $D_m$ [g/cm$^3$] | 1.424 Mg/m$^3$ |
| F(000) | 1112 |
| Crystal size [mm$^3$] | 0.45 × 0.4 × 0.3 |
| θ range [°] | 2 → 26 |
| Reflections collected | 8896 |
| Independent reflections | 4849 [$R_{int}$ = 0.0207] |
| S | 1.033 |
| R [I > 2σ(I)] | R1 = 0.0456, wR2 = 0.1076 |
| R indices (all data) | R1 = 0.0595, wR2 = 0.1165 |

TABLE 2.9 a) Single crystal data and structure refinement of malonate form II

| | |
|---|---|
| Empirical formula | $C_{20}H_{22}F_3N_4O^+ \cdot C_3H_3O_4^{-2} \cdot 2\ C_4H_{10}O$ |
| Fw | 642.71 |
| T [K] | 120(2) |
| λ[Å] | 0.71073 |
| Crystal system | Monoclinic |
| Space group | P 2$_1$/c |
| Unit cell dimensions | |
| a [Å] | 9.2650(3) |
| b [Å] | 24.2380(2) |
| c [Å] | 30.128(8) |
| α [°] | 90 |

TABLE 2.9-continued a) Single crystal data and structure refinement of malonate form II

| | |
|---|---|
| β [°] | 101.620(2) |
| γ [°] | 90 |
| V [Å$^3$] | 6627.0(4) |
| Z | 8 |
| $D_m$ [g/cm$^3$] | 1.288 |
| F(000) | 2736 |
| Crystal size [mm$^3$] | 0.25 × 0.1 × 0.08 |
| θ range [°] | 1.5 → 24 |
| Reflections collected | 22364 |
| Independent reflections | 10286 [$R_{int}$ = 0.1143] |
| S | 1.093 |
| R [I > 2σ(I)] | R1 = 0.1070, wR2 = 0.1271 |
| R indices (all data) | R1 = 0.2167, wR2 = 0.1563 |

TABLE 2.9 b) Atomic coordinates and temperature factor (Uiso) of malonate form II

| atom | x | y | z | U iso |
|---|---|---|---|---|
| O1 | 0.06149(5) | 0.95243(10) | 0.12162(17) | 0.0575(4) |
| C2 | 0.06563(7) | 1.04882(15) | 0.1421(2) | 0.0460(4) |
| N3 | 0.02959(7) | 1.12484(13) | 0.0841(2) | 0.0534(4) |
| H3 | 0.0000 | 11.075 | 0.013 | 0.05 |
| C4 | 0.05036(8) | 1.22360(15) | 0.1289(2) | 0.0483(4) |
| C5 | 0.03015(10) | 1.32383(17) | 0.0973(3) | 0.0630(5) |
| H5 | −0.0037 | 13.353 | 0.0364 | 0.05 |
| C6 | 0.06249(11) | 1.40672(17) | 0.1605(3) | 0.0694(6) |
| H6 | 0.0501 | 14.753 | 0.1412 | 0.05 |
| C7 | 0.11273(10) | 1.39022(17) | 0.2513(3) | 0.0653(6) |
| H7 | 0.1334 | 14.478 | 0.2912 | 0.05 |
| C8 | 0.13280(9) | 1.28983(16) | 0.2841(2) | 0.0546(5) |
| H8 | 0.1665 | 12.785 | 0.3453 | 0.05 |
| C9 | 0.10068(7) | 1.20725(14) | 0.22200(19) | 0.0428(4) |
| N10 | 0.10868(6) | 1.09832(11) | 0.23008(17) | 0.0429(3) |
| C11 | 0.15342(7) | 1.04136(15) | 0.3200(2) | 0.0433(4) |
| H11A | 0.1395 | 0.9719 | 0.3469 | 0.05 |
| H11B | 0.1632 | 10.785 | 0.4183 | 0.05 |
| C12 | 0.20654(7) | 1.03133(14) | 0.22173(18) | 0.0389(4) |
| H12A | 0.1957 | 10.007 | 0.119 | 0.05 |
| H12B | 0.2223 | 11.008 | 0.2033 | 0.05 |
| N13 | 0.25191(5) | 0.96389(10) | 0.30396(15) | 0.0334(3) |
| H13 | 0.2547 | 0.9800 | 0.411 | 0.05 |
| C14 | 0.23667(7) | 0.84980(13) | 0.2895(2) | 0.0397(4) |
| H14A | 0.2288 | 0.833 | 0.1781 | 0.05 |
| H14B | 0.2017 | 0.8368 | 0.3457 | 0.05 |
| C15 | 0.28364(7) | 0.77827(14) | 0.3555(2) | 0.0420(4) |
| H15A | 0.2891 | 0.7896 | 0.4694 | 0.05 |
| H15B | 0.2725 | 0.7054 | 0.3384 | 0.05 |
| N16 | 0.33750(6) | 0.79918(10) | 0.27768(16) | 0.0380(3) |
| C17 | 0.35469(7) | 0.90831(13) | 0.3045(2) | 0.0416(4) |
| H17A | 0.391 | 0.9214 | 0.2552 | 0.05 |
| H17B | 0.3602 | 0.921 | 0.4181 | 0.05 |
| C18 | 0.30930(7) | 0.98259(13) | 0.2356(2) | 0.0395(4) |
| H18A | 0.3212 | 10.546 | 0.257 | 0.05 |
| H18B | 0.306 | 0.9734 | 0.1209 | 0.05 |
| C19 | 0.38090(7) | 0.72145(13) | 0.28732(18) | 0.0372(4) |
| C20 | 0.43295(7) | 0.73712(14) | 0.2127(2) | 0.0437(4) |
| H20 | 0.4394 | 0.8002 | 0.1602 | 0.05 |
| C21 | 0.47493(8) | 0.65993(15) | 0.2160(2) | 0.0491(4) |
| C22 | 0.52955(9) | 0.67841(19) | 0.1321(3) | 0.0676(6) |
| F23 | 0.54009(8) | 0.77815(16) | 0.0996(3) | 0.1027(7) |
| F24 | 0.57558(6) | 0.64307(19) | 0.2129(3) | 0.1119(7) |
| F25 | 0.52921(11) | 0.6298(3) | −0.0085(3) | 0.1296(9) |
| F1 | 0.5567(8) | 0.5924(14) | 0.126(2) | 0.089(5) |
| F2 | 0.5243(8) | 0.6933(16) | −0.003(2) | 0.083(5) |
| F3 | 0.5524(8) | 0.7631(16) | 0.188(2) | 0.081(5) |
| C26 | 0.46634(9) | 0.56455(15) | 0.2925(2) | 0.0573(5) |
| H26 | 0.4947 | 0.5128 | 0.2949 | 0.05 |
| C27 | 0.41504(9) | 0.54833(15) | 0.3645(2) | 0.0571(5) |
| H27 | 0.4086 | 0.4847 | 0.4154 | 0.05 |
| C28 | 0.37289(8) | 0.62526(14) | 0.3624(2) | 0.0462(4) |
| H28 | 0.3385 | 0.6125 | 0.4121 | 0.05 |
| O31 | 0.25950(6) | 0.98586(10) | 0.62415(13) | 0.0515(3) |
| C32 | 0.28074(7) | 1.05416(13) | 0.71758(18) | 0.0390(4) |
| O33 | 0.26985(6) | 1.05918(9) | 0.86187(13) | 0.0486(3) |
| C34 | 0.32323(7) | 1.13283(13) | 0.65329(19) | 0.0417(4) |
| H34A | 0.3411 | 11.716 | 0.7417 | 0.05 |
| H34B | 0.3534 | 10.949 | 0.6009 | 0.05 |
| C35 | 0.29546(8) | 1.20947(13) | 0.53724(19) | 0.0425(4) |
| O36 | 0.2674(4) | 1.1813(6) | 0.4212(7) | 0.0620(17) |
| O36 | 0.2496(4) | 1.1918(7) | 0.4706(10) | 0.120(3) |
| O37 | 0.31592(7) | 1.30312(10) | 0.54566(16) | 0.0606(4) |
| H37 | 0.2947 | 1.352 | 0.464 | 0.05 |
| O40 | 0.13507(9) | 0.68241(17) | 0.4657(2) | 0.0836(5) |
| H40A | 0.1390 | 0.744 | 0.528 | 0.05 |
| H40B | 0.1122 | 0.639 | 0.520 | 0.05 |
| O41 | 0.16352(9) | 0.85416(13) | 0.6539(2) | 0.0708(4) |
| H41A | 0.1533 | 0.848 | 0.747 | 0.05 |
| H41B | 0.1949 | 0.906 | 0.666 | 0.05 |

(hydrogen atoms were calculated according to well-established geometrical criteria)

TABLE 2.10 a) Single crystal data and structure refinement of malonate form VI

| | |
|---|---|
| Empirical formula | $C_{20}H_{22}F_3N_4O^+ \cdot C_3H_3O_4^{-2} \cdot H_2O$ |
| Fw | 530.50 |
| T [K] | 120(2) |
| λ[Å] | 0.71073 |
| Crystal system | Triclinic |
| Space group | P −1 |
| Unit cell dimensions | |
| a [Å] | 7.8050(2) |
| b [Å] | 8.0730(2) |
| c [Å] | 20.1470(4) |
| α [°] | 80.0090(8) |
| β [°] | 87.4660(8) |
| γ [°] | 74.5320(9) |
| V [Å$^3$] | 1204.92(3) |
| Z | 2 |
| $D_m$ [g/cm$^3$] | 1.462 |
| F(000) | 556 |
| Crystal size [mm$^3$] | 0.3 × 0.25 × 0.1 |
| θ range [°] | 2 → 37 |
| Reflections collected | 14593 |
| Independent reflections | 12114 [$R_{int}$ = 0.0408] |
| S | 1.062 |
| R [I > 2σ(I)] | R1 = 0.0742, wR2 = 0.1389 |
| R indices (all data) | R1 = 0.1184, wR2 = 0.1594 |

TABLE 2.10 b) Atomic coordinates and temperature factor (Uiso) of malonate form VI

| atom | x | y | z | U (iso) |
|---|---|---|---|---|
| O1A | 0.6256(4) | 0.27887(16) | 0.17045(13) | 0.0277(11) |
| C2A | 0.5192(7) | 0.2652(3) | 0.1409(2) | 0.0212(15) |
| N3A | 0.4241(5) | 0.29908(19) | 0.11247(15) | 0.0212(12) |
| H3A | 0.4286 | 0.3353 | 0.1127 | 0.02 |
| C4A | 0.3190(6) | 0.2679(2) | 0.0831(2) | 0.0179(14) |
| C5A | 0.2037(6) | 0.2833(3) | 0.04897(19) | 0.0242(16) |
| H5A | 0.1833 | 0.3211 | 0.0418 | 0.02 |
| C6A | 0.1185(6) | 0.2416(3) | 0.0255(2) | 0.0294(17) |
| H6A | 0.0385 | 0.2508 | 0.0016 | 0.02 |
| C7A | 0.1483(6) | 0.1864(3) | 0.0364(2) | 0.0294(17) |
| H7A | 0.0876 | 0.1587 | 0.0199 | 0.02 |
| C8A | 0.2654(6) | 0.1710(3) | 0.07092(19) | 0.0262(16) |
| H8A | 0.2868 | 0.1334 | 0.078 | 0.02 |
| C9A | 0.3485(6) | 0.2127(2) | 0.09428(19) | 0.0190(15) |
| N10A | 0.4703(5) | 0.21199(19) | 0.13030(15) | 0.0204(12) |

TABLE 2.10-continued b) Atomic coordinates and temperature factor (Uiso) of malonate form VI

| atom | x | y | z | U (iso) |
|---|---|---|---|---|
| C11A | 0.5469(5) | 0.1621(2) | 0.14896(18) | 0.0172(14) |
| H11A | 0.6436 | 0.1728 | 0.1675 | 0.02 |
| H11B | 0.5659 | 0.1392 | 0.1236 | 0.02 |
| C12A | 0.4662(6) | 0.1273(2) | 0.17793(18) | 0.0172(14) |
| H12A | 0.3589 | 0.1304 | 0.1659 | 0.02 |
| H12B | 0.494 | 0.0882 | 0.1753 | 0.02 |
| N13A | 0.4970(4) | 0.14286(18) | 0.22701(14) | 0.0165(11) |
| H13A | 0.5969 | 0.1372 | 0.2383 | 0.02 |
| C14A | 0.4135(6) | 0.1054(2) | 0.25244(19) | 0.0238(15) |
| H14A | 0.4441 | 0.0668 | 0.2488 | 0.02 |
| H14B | 0.3069 | 0.1083 | 0.2392 | 0.02 |
| C15A | 0.4389(6) | 0.1192(2) | 0.30237(19) | 0.0226(15) |
| H15A | 0.3777 | 0.0948 | 0.3175 | 0.02 |
| H15B | 0.5436 | 0.1128 | 0.3165 | 0.02 |
| N16A | 0.4004(5) | 0.17688(19) | 0.30840(15) | 0.0199(12) |
| C17A | 0.4908(6) | 0.2133(2) | 0.28613(19) | 0.0223(15) |
| H17A | 0.5963 | 0.2075 | 0.2996 | 0.02 |
| H17B | 0.4664 | 0.2523 | 0.2912 | 0.02 |
| C18A | 0.4638(6) | 0.2019(2) | 0.23563(18) | 0.0184(14) |
| H18A | 0.3598 | 0.21 | 0.2218 | 0.02 |
| H18B | 0.5272 | 0.2262 | 0.2214 | 0.02 |
| C19A | 0.3798(5) | 0.1932(2) | 0.35192(19) | 0.0182(14) |
| C20A | 0.3480(5) | 0.2486(2) | 0.3594(2) | 0.0200(15) |
| H20A | 0.3438 | 0.2749 | 0.3358 | 0.02 |
| C21A | 0.3225(6) | 0.2651(2) | 0.40129(19) | 0.0187(14) |
| C22A | 0.2861(7) | 0.3240(3) | 0.4078(2) | 0.0254(16) |
| F23A | 0.3146(4) | 0.35757(15) | 0.37532(12) | 0.0509(11) |
| F24A | 0.1446(4) | 0.33182(15) | 0.40826(14) | 0.0566(12) |
| F25A | 0.3606(4) | 0.34482(15) | 0.44665(12) | 0.0541(12) |
| C26A | 0.3277(6) | 0.2278(3) | 0.4358(2) | 0.0262(16) |
| H26A | 0.3117 | 0.2395 | 0.4646 | 0.02 |
| C27A | 0.3561(7) | 0.1734(3) | 0.4284(2) | 0.0358(18) |
| H27A | 0.3561 | 0.1472 | 0.4519 | 0.02 |
| C28A | 0.3849(6) | 0.1560(2) | 0.3871(2) | 0.0284(16) |
| H28A | 0.4082 | 0.1185 | 0.383 | 0.02 |
| O31A | 0.7669(4) | 0.04516(16) | 0.26795(14) | 0.0319(11) |
| C32A | 0.8398(6) | 0.0894(2) | 0.27126(19) | 0.0209(15) |
| O33A | 0.7893(4) | 0.13579(16) | 0.25753(13) | 0.0282(11) |
| C34A | 1.0035(5) | 0.0870(2) | 0.29359(19) | 0.0203(15) |
| H34A | 1.061 | 0.0976 | 0.2706 | 0.02 |
| H34B | 1.0222 | 0.1154 | 0.3177 | 0.02 |
| C35A | 1.0641(7) | 0.0322(2) | 0.3144(2) | 0.0245(16) |
| O36A | 0.9790(4) | −0.01052(16) | 0.30492(15) | 0.0352(12) |
| H36A | 0.8956 | −0.0003 | 0.2908 | 0.02 |
| O37A | 1.1868(4) | 0.02969(16) | 0.33793(14) | 0.0333(12) |
| O41A | 1.2576(4) | −0.05443(17) | 0.40344(13) | 0.0288(11) |
| H41A | 1.2167 | −0.0332 | 0.3826 | 0.02 |
| C42A | 1.2321(6) | −0.0346(3) | 0.4464(2) | 0.0277(16) |
| C43A | 1.2648(7) | 0.0266(3) | 0.4509(2) | 0.047(2) |
| H43A | 1.3679 | 0.0332 | 0.4492 | 0.02 |
| H43B | 1.2471 | 0.0399 | 0.4801 | 0.02 |
| H43C | 1.2004 | 0.0465 | 0.4262 | 0.02 |
| C44A | 1.3404(7) | −0.0664(3) | 0.4820(2) | 0.045(2) |
| H44A | 1.4413 | −0.0583 | 0.4787 | 0.02 |
| H44B | 1.3216 | −0.1061 | 0.478 | 0.02 |
| H44C | 1.328 | −0.0554 | 0.5123 | 0.02 |
| C45A | 1.0738(7) | −0.0465(3) | 0.4494(2) | 0.058(2) |
| H45A | 1.0073 | −0.0258 | 0.4258 | 0.02 |
| H45B | 1.0573 | −0.0353 | 0.4793 | 0.02 |
| H45C | 1.0544 | −0.0861 | 0.4452 | 0.02 |
| O51A | 1.5312(4) | −0.08854(17) | 0.39215(14) | 0.0309(11) |
| H51A | 1.4456 | −0.0785 | 0.3938 | 0.02 |
| C52A | 1.5851(6) | −0.0545(3) | 0.3599(2) | 0.0286(16) |
| C53A | 1.6192(7) | 0.0023(2) | 0.3799(2) | 0.051(2) |
| H53A | 1.5276 | 0.0201 | 0.3838 | 0.02 |
| H53B | 1.6655 | 0.0245 | 0.3595 | 0.02 |
| H53C | 1.6864 | −0.0009 | 0.4094 | 0.02 |
| C54A | 1.7245(6) | −0.0836(3) | 0.3520(2) | 0.0405(19) |
| H54A | 1.6987 | −0.1202 | 0.339 | 0.02 |
| H54B | 1.7946 | −0.0875 | 0.3809 | 0.02 |
| H54C | 1.7695 | −0.0617 | 0.331 | 0.02 |
| C55A | 1.4715(7) | −0.0522(3) | 0.3158(2) | 0.049(2) |
| H55A | 1.3826 | −0.0334 | 0.321 | 0.02 |
| H55B | 1.4464 | −0.0897 | 0.3049 | 0.02 |
| H55C | 1.5123 | −0.0318 | 0.2931 | 0.02 |
| O1B | 0.1417(4) | 0.19068(16) | 0.17087(13) | 0.0252(10) |
| C2B | 0.0323(6) | 0.2013(2) | 0.1414(2) | 0.0198(15) |
| N3B | −0.0561(5) | 0.16559(19) | 0.11321(15) | 0.0209(12) |
| H3B | −0.0436 | 0.1296 | 0.1133 | 0.02 |
| C4B | −0.1687(6) | 0.1934(2) | 0.08423(18) | 0.0188(15) |
| C5B | −0.2809(6) | 0.1751(3) | 0.05088(18) | 0.0236(15) |
| H5B | −0.2934 | 0.137 | 0.0434 | 0.02 |
| C6B | −0.3765(6) | 0.2155(3) | 0.02831(19) | 0.0258(16) |
| H6B | −0.4561 | 0.2045 | 0.0049 | 0.02 |
| C7B | −0.3584(6) | 0.2715(3) | 0.03916(19) | 0.0241(16) |
| H7B | −0.425 | 0.2977 | 0.0229 | 0.02 |
| C8B | −0.2446(6) | 0.2893(2) | 0.07324(18) | 0.0193(14) |
| H8B | −0.2318 | 0.3272 | 0.0808 | 0.02 |
| C9B | −0.1505(6) | 0.2498(2) | 0.09576(18) | 0.0146(14) |
| N10B | −0.0273(5) | 0.25355(18) | 0.13118(15) | 0.0172(12) |
| C11B | 0.0424(6) | 0.3050(2) | 0.14887(18) | 0.0216(15) |
| H11C | 0.0595 | 0.3277 | 0.1231 | 0.02 |
| H11D | 0.1399 | 0.2964 | 0.168 | 0.02 |
| C12B | −0.0455(6) | 0.3390(2) | 0.17676(17) | 0.0180(14) |
| H12C | −0.0201 | 0.3784 | 0.1744 | 0.02 |
| H12D | −0.1518 | 0.3347 | 0.1636 | 0.02 |
| N13B | −0.0190(5) | 0.32326(18) | 0.22561(15) | 0.0171(12) |
| H13B | 0.0805 | 0.3287 | 0.2378 | 0.02 |
| C14B | −0.1054(6) | 0.3604(2) | 0.25018(18) | 0.0216(15) |
| H14C | −0.2115 | 0.3571 | 0.2365 | 0.02 |
| H14D | −0.0755 | 0.3992 | 0.2467 | 0.02 |
| C15B | −0.0812(6) | 0.3463(2) | 0.29995(19) | 0.0237(16) |
| H15C | 0.0236 | 0.3521 | 0.3142 | 0.02 |
| H15D | −0.1418 | 0.3708 | 0.315 | 0.02 |
| N16B | −0.1215(4) | 0.28845(19) | 0.30597(15) | 0.0187(12) |
| C17B | −0.0337(6) | 0.2518(2) | 0.28316(17) | 0.0192(14) |
| H17C | −0.0624 | 0.2131 | 0.2872 | 0.02 |
| H17D | 0.0718 | 0.2559 | 0.2974 | 0.02 |
| C18B | −0.0546(6) | 0.2643(2) | 0.23363(18) | 0.0169(14) |
| H18C | −0.158 | 0.2566 | 0.2188 | 0.02 |
| H18D | 0.0099 | 0.2399 | 0.2198 | 0.02 |
| C19B | −0.1474(6) | 0.2726(2) | 0.34842(19) | 0.0190(15) |
| C20B | −0.1114(6) | 0.2197(2) | 0.36562(19) | 0.0224(15) |
| H20B | −0.0582 | 0.1955 | 0.35 | 0.02 |
| C21B | −0.1516(6) | 0.2022(3) | 0.4048(2) | 0.0267(16) |
| C22B | −0.1134(9) | 0.1451(2) | 0.4220(2) | 0.0395(19) |
| F23B | −0.0087(9) | 0.1436(3) | 0.4596(3) | 0.083(3) |
| F24B | −0.2331(9) | 0.1182(3) | 0.4324(3) | 0.084(3) |
| F25B | 0.0721(10) | 0.1111(2) | 0.39188(19) | 0.072(2) |
| F23B | 0.0097(19) | 0.1262(8) | 0.4107(7) | 0.045(6) |
| F24B | −0.083(2) | 0.1414(10) | 0.4649(9) | 0.042(7) |
| F25B | −0.211(3) | 0.1131(12) | 0.4113(8) | 0.068(9) |
| C26B | −0.2274(6) | 0.2364(3) | 0.4293(2) | 0.0284(16) |
| H26B | −0.2571 | 0.2236 | 0.4559 | 0.02 |
| C27B | −0.2578(6) | 0.2894(3) | 0.4136(2) | 0.0293(16) |
| H27B | −0.3057 | 0.3141 | 0.4305 | 0.02 |
| C28B | −0.2202(5) | 0.3075(2) | 0.37391(19) | 0.0223(15) |
| H28C | −0.244 | 0.3441 | 0.3637 | 0.02 |
| O31B | 0.6664(4) | 0.43895(16) | 0.33478(13) | 0.0302(11) |
| C32B | 0.5421(7) | 0.4349(2) | 0.3115(2) | 0.0221(15) |
| O33B | 0.4540(4) | 0.47697(16) | 0.30146(13) | 0.0276(11) |
| C34B | 0.4840(6) | 0.3795(2) | 0.29294(19) | 0.0213(15) |
| H34C | 0.5031 | 0.3526 | 0.3182 | 0.02 |
| H34D | 0.5424 | 0.3677 | 0.2705 | 0.02 |
| C35B | 0.3212(6) | 0.3755(3) | 0.27050(19) | 0.0196(15) |
| O36B | 0.2732(4) | 0.32836(16) | 0.25941(13) | 0.0249(10) |
| O37B | 0.2453(4) | 0.41894(16) | 0.26514(14) | 0.0278(11) |
| H37B | 0.2978 | 0.4458 | 0.2761 | 0.02 |
| O41B | 0.7322(4) | 0.51862(16) | 0.40487(12) | 0.0286(11) |
| H41B | 0.7136 | 0.497 | 0.3827 | 0.02 |
| C42B | 0.7157(7) | 0.4897(3) | 0.4455(2) | 0.0312(17) |
| C43B | 0.7507(8) | 0.5326(3) | 0.4831(2) | 0.062(2) |
| H43C | 0.6785 | 0.5626 | 0.4771 | 0.02 |
| H43D | 0.8497 | 0.5474 | 0.4842 | 0.02 |
| H43E | 0.7466 | 0.5153 | 0.5122 | 0.02 |
| C44B | 0.5603(7) | 0.4701(4) | 0.4409(2) | 0.089(3) |
| H44C | 0.5383 | 0.443 | 0.4163 | 0.02 |
| H44D | 0.4928 | 0.5015 | 0.434 | 0.02 |
| H44E | 0.5479 | 0.4529 | 0.4694 | 0.02 |
| C45B | 0.8230(8) | 0.4422(3) | 0.4545(3) | 0.073(3) |

TABLE 2.10-continued b) Atomic coordinates and temperature factor (Uiso) of malonate form VI

| atom | x | y | z | U (iso) |
|---|---|---|---|---|
| H45C | 0.8004 | 0.4156 | 0.4296 | 0.02 |
| H45D | 0.8146 | 0.4241 | 0.483 | 0.02 |
| H45E | 0.9236 | 0.4561 | 0.4568 | 0.02 |
| O51B | 1.0131(4) | 0.55326(16) | 0.39488(13) | 0.0263(10) |
| H51B | 0.9303 | 0.5415 | 0.3979 | 0.02 |
| C52B | 1.0615(6) | 0.5226(2) | 0.3591(2) | 0.0261(16) |
| C53B | 1.0829(7) | 0.4625(2) | 0.3718(2) | 0.0386(18) |
| H53C | 0.9879 | 0.4462 | 0.3741 | 0.02 |
| H53D | 1.1514 | 0.4593 | 0.4011 | 0.02 |
| H53E | 1.1233 | 0.443 | 0.3486 | 0.02 |
| C54B | 1.2073(6) | 0.5495(3) | 0.3542(2) | 0.046(2) |
| H54C | 1.1901 | 0.5884 | 0.3458 | 0.02 |
| H54D | 1.2467 | 0.5304 | 0.3306 | 0.02 |
| H54E | 1.2781 | 0.547 | 0.383 | 0.02 |
| C55B | 0.9471(7) | 0.5300(3) | 0.3152(2) | 0.0400(18) |
| H55C | 0.8535 | 0.5135 | 0.3188 | 0.02 |
| H55D | 0.9818 | 0.5118 | 0.2903 | 0.02 |
| H55E | 0.9329 | 0.5694 | 0.3086 | 0.02 |

(hydrogen atoms were calculated according to well-established geometrical criteria)

TABLE 2.11 a) Single crystal data and structure refinement of salicylate form I

| Empirical formula | $C_{20}H_{22}F_3N_4O^+ \cdot C_7H_5O_3^-$ |
|---|---|
| Fw | 528.53 |
| T [K] | 293(2) |
| λ [Å] | 0.71073 |
| Crystal system | Monoclinic |
| Space group | $P\,2_1/c$ |
| Unit cell dimensions | |
| a [Å] | 16.3790(2) |
| b [Å] | 15.4410(4) |
| c [Å] | 10.1810(4) |
| α [°] | 90 |
| β [°] | 98.1820(12) |
| γ [°] | 90 |
| V [Å$^3$] | 2548.6(2) |
| Z | 4 |
| $D_m$ [g/cm$^3$] | 1.377 |
| F(000) | 1104 |
| Crystal size [mm$^3$] | 0.4 × 0.3 × 0.2 |
| θ range [°] | 2.5 → 26 |
| Reflections collected | 12472 |
| Independent reflections | 4948 [$R_{int}$ = 0.0289] |
| S | 0.949 |
| R [I > 2σ(I)] | R1 = 0.0565, wR2 = 0.1471 |
| R indices (all data) | R1 = 0.0753, wR2 = 0.1647 |

TABLE 2.11 b) Atomic coordinates and temperature factor (Uiso) of salicylate, form I

| atom | x | y | z | U (iso) |
|---|---|---|---|---|
| O1 | 0.91497(11) | 0.00803(11) | 0.86442(19) | 0.0872(6) |
| C2 | 0.92301(13) | 0.08333(15) | 0.9039(2) | 0.0671(6) |
| N3 | 0.97769(12) | 0.11514(13) | 1.0059(2) | 0.0722(6) |
| H3 | 1.0131(17) | 0.0818(18) | 1.054(8) | 0.084(8) |
| C4 | 0.96828(12) | 0.20377(15) | 1.0166(2) | 0.0624(5) |
| C5 | 1.00965(14) | 0.26490(17) | 1.0998(3) | 0.0744(7) |
| H5 | 10.514 | 0.2491 | 11.672 | 0.08 |
| C6 | 0.98680(16) | 0.35012(18) | 1.0790(3) | 0.0828(7) |
| H6 | 1.014 | 0.3928 | 11.329 | 0.08 |
| C7 | 0.92424(17) | 0.37350(17) | 0.9796(3) | 0.0824(7) |
| H7 | 0.9107 | 0.4317 | 0.9676 | 0.08 |
| C8 | 0.88124(15) | 0.31250(15) | 0.8975(3) | 0.0709(6) |
| H8 | 0.8385 | 0.3283 | 0.8317 | 0.08 |
| C9 | 0.90464(12) | 0.22768(14) | 0.9177(2) | 0.0590(5) |
| N10 | 0.87721(10) | 0.15220(12) | 0.85117(18) | 0.0616(5) |
| C11 | 0.81040(12) | 0.14457(15) | 0.7420(2) | 0.0611(5) |
| H11A | 0.8186 | 0.0935 | 0.6899 | 0.08 |
| H11B | 0.8098 | 0.1949 | 0.6848 | 0.08 |
| C12 | 0.72893(12) | 0.13770(14) | 0.7952(2) | 0.0567(5) |
| H12A | 0.7233 | 0.0798 | 0.8296 | 0.08 |
| H12B | 0.7288 | 0.1781 | 0.8681 | 0.08 |
| N13 | 0.65689(9) | 0.15639(10) | 0.69194(15) | 0.0456(4) |
| H13 | 0.6660 | 0.2124 | 0.660 | 0.08 |
| C14 | 0.65126(12) | 0.09592(12) | 0.57744(19) | 0.0521(5) |
| H14A | 0.646 | 0.0371 | 0.6084 | 0.08 |
| H14B | 0.7015 | 0.0995 | 0.5375 | 0.08 |
| C15 | 0.57810(12) | 0.11730(13) | 0.47439(19) | 0.0530(5) |
| H15A | 0.5866 | 0.1736 | 0.4363 | 0.08 |
| H15B | 0.5742 | 0.0748 | 0.4036 | 0.08 |
| N16 | 0.50127(9) | 0.11822(9) | 0.53024(14) | 0.0463(4) |
| C17 | 0.50607(12) | 0.17499(14) | 0.6462(2) | 0.0553(5) |
| H17A | 0.4555 | 0.1702 | 0.685 | 0.08 |
| H17B | 0.5116 | 0.2346 | 0.6187 | 0.08 |
| C18 | 0.57805(12) | 0.15162(14) | 0.7483(2) | 0.0581(5) |
| H18A | 0.5804 | 0.1909 | 0.8231 | 0.08 |
| H18B | 0.5707 | 0.0934 | 0.7804 | 0.08 |
| C19 | 0.42806(11) | 0.12442(11) | 0.43852(18) | 0.0460(4) |
| C20 | 0.35149(12) | 0.12890(11) | 0.48298(19) | 0.0499(4) |
| H20 | 0.3489 | 0.1313 | 0.5736 | 0.08 |
| C21 | 0.27903(12) | 0.12987(12) | 0.3938(2) | 0.0539(5) |
| C22 | 0.19946(14) | 0.13183(16) | 0.4478(3) | 0.0684(6) |
| F23 | 0.19854(9) | 0.19130(12) | 0.54236(17) | 0.0973(5) |
| F24 | 0.18397(11) | 0.05872(12) | 0.5046(3) | 0.1286(8) |
| F25 | 0.13575(9) | 0.15083(16) | 0.35812(18) | 0.1216(7) |
| C26 | 0.28037(14) | 0.12594(15) | 0.2590(2) | 0.0663(6) |
| H26 | 0.2316 | 0.1253 | 0.1997 | 0.08 |
| C27 | 0.35586(16) | 0.12292(16) | 0.2143(2) | 0.0702(6) |
| H27 | 0.3578 | 0.1212 | 0.1235 | 0.08 |
| C28 | 0.42895(14) | 0.12245(14) | 0.3015(2) | 0.0591(5) |
| H28 | 0.4791 | 0.1208 | 0.2686 | 0.08 |
| O31 | 0.70266(9) | 0.30926(9) | 0.62125(18) | 0.0738(5) |
| C32 | 0.66099(13) | 0.37670(12) | 0.62665(19) | 0.0527(5) |
| O33 | 0.58513(11) | 0.37610(11) | 0.6255(2) | 0.0935(6) |
| C34 | 0.70438(14) | 0.46195(12) | 0.63243(18) | 0.0562(5) |
| C35 | 0.6612(2) | 0.53938(14) | 0.6406(2) | 0.0754(7) |
| O36 | 0.57910(18) | 0.53960(15) | 0.6404(3) | 0.1133(8) |
| H36 | 0.559 | 0.486 | 0.612 | 0.08 |
| C37 | 0.7032(3) | 0.61784(17) | 0.6487(3) | 0.1008(11) |
| H37 | 0.6747 | 0.6694 | 0.6551 | 0.08 |
| C38 | 0.7862(3) | 0.6191(2) | 0.6473(3) | 0.1212(15) |
| H38 | 0.8138 | 0.6719 | 0.6518 | 0.08 |
| C39 | 0.8304(2) | 0.5434(2) | 0.6394(3) | 0.1079(11) |
| H39 | 0.8872 | 0.5451 | 0.6395 | 0.08 |
| C40 | 0.78916(17) | 0.46572(17) | 0.6314(2) | 0.0780(7) |
| H40 | 0.8185 | 0.4146 | 0.6251 | 0.08 |

(hydrogen atoms were calculated according to well-established geometrical criteria)

TABLE 2.12

Single crystal data and structure refinement of L-tartate form I

| Empirical formula | $2\,C_{20}H_{22}F_3N_4O^+ \cdot C_4H_4O_6^{2-} \cdot 2\,H_2O$ |
|---|---|
| Fw | 966.94 |
| T [K] | 293(2) |
| λ [Å] | 0.71073 |
| Crystal system | Triclinic |
| Space group | P 1 |
| Unit cell dimensions | |
| a [Å] | 9.4030(2) |
| b [Å] | 10.7370(3) |
| c [Å] | 11.7620(3) |
| α [°] | 98.355(1) |
| β [°] | 93.917(1) |
| γ [°] | 109.172(1) |

TABLE 2.12-continued

Single crystal data and structure refinement of L-tartate form I

| | |
|---|---|
| V [Å$^3$] | 1101.14(5) |
| Z | 1 |
| D$_m$ [g/cm$^3$] | 1.458 |
| F(000) | 506 |
| Crystal size [mm$^3$] | 0.4 × 0.25 × 0.17 |
| θ range [°] | 2.5 → 27.5 |
| Reflections collected | 7358 |
| Independent reflections | 7358 [R$_{int}$ = 0.0000] |
| S | 1.028 |
| R [I > 2σ(I)] | R1 = 0.0444, wR2 = 0.1196 |
| R indices (all data) | R1 = 0.0491, wR2 = 0.1257 |

TABLE 2.13

Single crystal data and structure refinement of fumarate form I

| | |
|---|---|
| Empirical formula | 2 (C$_{20}$H$_{22}$F$_3$N$_4$O$^+$)·C$_4$H$_2$O$_4^{2-}$·C$_4$H$_4$O$_4$ |
| Fw | 1012.96 |
| T [K] | 293(2) |
| λ[Å] | 0.71073 |
| Crystal system | Triclinic |
| Space group | P −1 |
| Unit cell dimensions | |
| a [Å] | 9.5900(2) |
| b [Å] | 11.6620(2) |
| c [Å] | 12.2070(3) |
| α [°] | 67.0130(11) |
| β [°] | 68.8250(10) |
| γ [°] | 88.8640(12) |
| V [Å$^3$] | 1160.20(4) |
| Z | 1 |
| D$_m$ [g/cm$^3$] | 1.450 |
| F(000) | 528 |
| Crystal size [mm$^3$] | 0.35 × 0.35 × 0.2 |
| θ range [°] | 3 → 26 |
| Reflections collected | 7642 |
| Independent reflections | 4536 [R$_{int}$ = 0.0199] |
| S | 1.058 |
| R [I > 2σ(I)] | R1 = 0.0452, wR2 = 0.0999 |
| R indices (all data) | R1 = 0.0594, wR2 = 0.1091 |

TABLE 2.14

Single crystal data and structure refinement of fumarate form II

| | |
|---|---|
| Empirical formula | C$_{20}$H$_{22}$F$_3$N$_4$O$^+$·0.5 C$_4$H$_2$O$_4^{2-}$·H$_2$O·H$_2$O |
| Fw | 466.46 |
| T [K] | 120(2) |
| λ[Å] | 0.71073 |
| Crystal system | Triclinic |
| Space group | P −1 |
| Unit cell dimensions | |
| a [Å] | 9.0720(3) |
| b [Å] | 10.7140(2) |
| c [Å] | 11.7530(8) |
| α [°] | 96.708(2) |
| β [°] | 95.355(2) |
| γ [°] | 109.214(2) |
| V [Å$^3$] | 1060.71(11) |
| Z | 2 |
| D$_m$ [g/cm$^3$] | 1.460 |
| F(000) | 488 |
| Crystal size [mm$^3$] | 0.20 × 0.15 × 0.1 |
| θ range [°] | 2.5 → 26 |
| Reflections collected | 6160 |
| Independent reflections | 4054 [R$_{int}$ = 0.0662] |
| S | 1.061 |
| R [I > 2σ(I)] | R1 = 0.0618, wR2 = 0.1331 |
| R indices (all data) | R1 = 0.0825, wR2 = 0.1465 |

TABLE 2.15

Single crystal data and structure refinement of citrate form I

| | |
|---|---|
| Empirical formula | C$_{20}$H$_{22}$F$_3$N$_4$O$^+$·C$_6$H$_9$O$_8^-$·C$_2$H$_6$O |
| Fw | 628.60 |
| T [K] | 293(2) |
| λ[Å] | 0.71073 |
| Crystal system | Orthorhombic |
| Space group | Pca2$_1$ |
| Unit cell dimensions | |
| a [Å] | 25.4880(4) |
| b [Å] | 15.6530(8) |
| c [Å] | 7.6090(16) |
| α [°] | 90 |
| β [°] | 90 |
| γ [°] | 90 |
| V [Å$^3$] | 3035.7(7) |
| Z | 4 |
| D$_m$ [g/cm$^3$] | 1.375 |
| F(000) | 1320 |
| Crystal size [mm$^3$] | 0.25 × 0.25 × 0.18 |
| θ range [°] | 2.5 → 25 |
| Reflections collected | 17271 |
| Independent reflections | 5321 [R$_{int}$ = 0.0483] |
| S | 1.073 |
| R [I > 2σ(I)] | R1 = 0.0493, wR2 = 0.1044 |
| R indices (all data) | R1 = 0.0675, wR2 = 0.1126 |

TABLE 2.16

Single crystal data and structure refinement of mandelate form I

| | |
|---|---|
| Empirical formula | C$_{20}$H$_{22}$F$_3$N$_4$O$^+$·C$_8$H$_7$O$_3^-$ |
| Fw | 542.55 |
| T [K] | 293(2) |
| λ[Å] | 0.71073 |
| Crystal system | Orthorhombic |
| Space group | P 2$_1$2$_1$2$_1$ |
| Unit cell dimensions | |
| a [Å] | 9.7220(2) |
| b [Å] | 22.5720(3) |
| c [Å] | 23.9740(4) |
| α [°] | 90 |
| β [°] | 90 |
| γ [°] | 90 |
| V [Å$^3$] | 5261.0(2) |
| Z | 8 |
| D$_m$ [g/cm$^3$] | 1.370 |
| F(000) | 2272 |
| Crystal size [mm$^3$] | 0.35 × 0.3 × 0.25 |
| θ range [°] | 1 → 26 |
| Reflections collected | 28800 |
| Independent reflections | 10298 [R(int) = 0.0760] |
| S | 1.040 |
| R [I > 2σ(I)] | R1 = 0.0732, wR2 = 0.1539 |
| R indices (all data) | R1 = 0.1163, wR2 = 0.1765 |

TABLE 2.17

Single crystal data and structure refinement of L-malate form I

| | |
|---|---|
| Empirical formula | C$_{24}$H$_{22}$F$_3$N$_4$O$^+$·C$_4$H$_5$O$_5^-$·H$_2$O |
| Fw | 542.51 |
| T [K] | 293(2) |
| λ[Å] | 0.71073 |
| Crystal system | Triclinic |
| Space group | P 1 |
| Unit cell dimensions | |
| a [Å] | 7.8000(2) |
| b [Å] | 8.0610(2) |
| c [Å] | 21.1650(3) |

TABLE 2.17-continued

Single crystal data and structure refinement of L-malate form I

| | |
|---|---|
| α [°] | 82.578(1) |
| β [°] | 82.526(1) |
| γ [°] | 77.692(1) |
| V [Å$^3$] | 1282.05(3) Å$^3$ |
| Z | 2 |
| D$_m$ [g/cm$^3$] | 1.405 |
| F(000) | 568 |
| Crystal size [mm$^3$] | 0.25 × 0.25 × 0.2 |
| θ range [°] | 2 → 26 |
| Reflections collected | 8379 |
| Independent reflections | 8379 [R$_{int}$ = 0.0000] |
| S | 1.026 |
| R [I > 2σ(I)] | R1 = 0.0350, wR2 = 0.0815 |
| R indices (all data) | R1 = 0.0384, wR2 = 0.0844 |

TABLE 2.18 a) Single crystal data and structure refinement of succinate form I

| | |
|---|---|
| Empirical formula | 2 C$_{20}$H$_{22}$F$_3$N$_4$O$^+$·C$_4$H$_4$O$_4^{2-}$·2 H$_2$O |
| Fw | 934.94 |
| T [K] | 293(2) |
| λ[Å] | 0.71073 |
| Crystal system | Triclinic |
| Space group | P −1 |
| Unit cell dimensions | |
| a [Å] | 9.5450(4) |
| b [Å] | 10.7120(5) |
| c [Å] | 11.7330(7) |
| α [°] | 97.597(2) |
| β [°] | 93.690(2) |
| γ [°] | 110.663(3) |
| V [Å$^3$] | 1104.6(1) |
| Z | 1 |
| D$_m$ [g/cm$^3$] | 1.405 |
| F(000) | 490 |
| Crystal size [mm$^3$] | 0.3 × 0.3 × 0.2 |
| θ range [°] | 3.5 → 26 |
| Reflections collected | 6382 |
| Independent reflections | 4176 [R$_{int}$ = 0.0194] |
| S | 1.036 |
| R [I > 2σ(I)] | R1 = 0.0555, wR2 = 0.1386 |
| R indices (all data) | R1 = 0.0649, wR2 = 0.1484 |

TABLE 2.18 b) Atomic coordinates and temperature factor (Uiso) of succinate, form I

| atom | x | y | z | U (iso) |
|---|---|---|---|---|
| O1 | 0.11215(14) | −0.33344(13) | 0.08086(12) | 0.0588(4) |
| C2 | 0.20693(19) | −0.36147(17) | 0.02653(15) | 0.0473(4) |
| N3 | 0.18520(18) | −0.47601(15) | −0.04935(14) | 0.0510(4) |
| H3 | 0.097 | −0.541 | −0.0650 | 0.07 |
| C4 | 0.3180(2) | −0.46756(17) | −0.09559(14) | 0.0471(4) |
| C5 | 0.3527(2) | −0.5538(2) | −0.17731(17) | 0.0582(5) |
| H5 | 0.2808 | −0.6367 | −0.2123 | 0.07 |
| C6 | 0.4993(3) | −0.5117(2) | −0.20481(18) | 0.0655(5) |
| H6 | 0.5258 | −0.5667 | −0.2606 | 0.07 |
| C7 | 0.6070(3) | −0.3898(2) | −0.15142(19) | 0.0659(5) |
| H7 | 0.7047 | −0.3653 | −0.1712 | 0.07 |
| C8 | 0.5727(2) | −0.3037(2) | −0.06925(17) | 0.0575(5) |
| H8 | 0.6455 | −0.222 | −0.0328 | 0.07 |
| C9 | 0.42669(19) | −0.34370(17) | −0.04361(14) | 0.0461(4) |
| N10 | 0.35550(16) | −0.28081(14) | 0.03201(12) | 0.0471(3) |
| C11 | 0.4200(2) | −0.14335(17) | 0.09490(15) | 0.0486(4) |
| H11A | 0.3413 | −0.106 | 0.1011 | 0.07 |
| H11B | 0.495 | −0.0883 | 0.052 | 0.07 |
| C12 | 0.49289(19) | −0.13732(16) | 0.21523(14) | 0.0438(4) |
| H12A | 0.4149 | −0.1742 | 0.2638 | 0.07 |
| H12B | 0.5543 | −0.1928 | 0.2106 | 0.07 |

TABLE 2.18-continued b) Atomic coordinates and temperature factor (Uiso) of succinate, form I

| atom | x | y | z | U (iso) |
|---|---|---|---|---|
| N13 | 0.58818(14) | 0.00287(13) | 0.26891(11) | 0.0378(3) |
| H13 | 0.687(3) | 0.048(3) | 0.204(3) | 0.109(9) |
| C14 | 0.6605(2) | 0.00347(17) | 0.38462(14) | 0.0457(4) |
| H14A | 0.7202 | −0.0534 | 0.3767 | 0.07 |
| H14B | 0.5831 | −0.0343 | 0.4333 | 0.07 |
| C15 | 0.7605(2) | 0.14425(18) | 0.44207(15) | 0.0489(4) |
| H15A | 0.7997 | 0.141 | 0.5196 | 0.07 |
| H15B | 0.8455 | 0.1773 | 0.3987 | 0.07 |
| N16 | 0.68001(16) | 0.23859(14) | 0.44916(12) | 0.0452(3) |
| C17 | 0.6059(2) | 0.23599(17) | 0.33567(16) | 0.0501(4) |
| H17A | 0.6818 | 0.2708 | 0.2849 | 0.07 |
| H17B | 0.5479 | 0.2942 | 0.3435 | 0.07 |
| C18 | 0.50283(19) | 0.09428(17) | 0.28235(15) | 0.0460(4) |
| H18A | 0.4242 | 0.0608 | 0.3312 | 0.07 |
| H18B | 0.4552 | 0.0956 | 0.2072 | 0.07 |
| C19 | 0.75610(19) | 0.36736(17) | 0.51691(14) | 0.0452(4) |
| C20 | 0.7328(2) | 0.48246(18) | 0.49104(16) | 0.0505(4) |
| H20 | 0.6692 | 0.4758 | 0.4252 | 0.07 |
| C21 | 0.8033(2) | 0.60673(18) | 0.56230(16) | 0.0517(4) |
| C22 | 0.7781(2) | 0.7274(2) | 0.5290(2) | 0.0703(6) |
| F23 | 0.8472(13) | 0.7647(11) | 0.4342(8) | 0.100(3) |
| F24 | 0.6390(9) | 0.7062(9) | 0.5010(11) | 0.132(4) |
| F25 | 0.8386(14) | 0.8364(12) | 0.6034(12) | 0.126(4) |
| F23 | 0.7798(13) | 0.8151(14) | 0.6255(14) | 0.122(4) |
| F24 | 0.6396(8) | 0.6996(6) | 0.4736(8) | 0.087(2) |
| F25 | 0.8708(10) | 0.7912(12) | 0.4664(10) | 0.130(4) |
| C26 | 0.8986(2) | 0.6210(2) | 0.66037(17) | 0.0588(5) |
| H26 | 0.9447 | 0.7044 | 0.7082 | 0.07 |
| C27 | 0.9232(3) | 0.5083(2) | 0.68525(18) | 0.0701(6) |
| H27 | 0.9883 | 0.5162 | 0.7506 | 0.07 |
| C28 | 0.8541(2) | 0.3836(2) | 0.61586(17) | 0.0625(5) |
| H28 | 0.8732 | 0.3092 | 0.6354 | 0.07 |
| O31 | 0.78415(16) | 0.08581(15) | 0.12641(13) | 0.0662(4) |
| C32 | 0.8705(2) | 0.0184(2) | 0.11696(17) | 0.0535(4) |
| O33 | 0.8627(2) | −0.0710(2) | 0.17358(17) | 0.0949(6) |
| C34 | 0.9814(3) | 0.0534(3) | 0.0300(3) | 0.0867(8) |
| H34A | 0.9416 | 0.0936 | −0.0273 | 0.07 |
| H34B | 10.741 | 0.1224 | 0.0697 | 0.07 |
| O35 | 1.1282(2) | −0.1195(2) | 0.26152(16) | 0.0836(5) |
| H35A | 1.023(5) | −0.114(4) | 0.246(4) | 0.165(16) |
| H35B | 1.107(4) | −0.204(4) | 0.196(3) | 0.135(12) |

(hydrogen atoms were calculated according to well-established geometrical criteria)

A further object of the present invention is the use of the above salts end crystalline salt forms for the manufacture of a medicament for the treatment or prevention of the following diseases.

The indication of the above salts and crystalline salt forms of the present invention may include all known indications for flibanserin, e.g. in the treatment of patients suffering from central nervous system disorders, in particular in affective disorders (e.g. depression like major depressive disorder, childhood depression, dysthymia, seasonal affective disorder, dysthymic disorder and minor depressive disorder; bipolar disorders), anxiety (incl. panic disorder with or without agoraphobia, agoraphobia without history of name disorder, specific phobia (simple phobia), social phobia (social anxiety disorder), obsessive-compulsive disorder (OCD), post-traumatic stress disorder, acute stress disorder, generalized anxiety disorder and anxiety disorder not otherwise specified), sleep and sexual disorders (e.g. Hypoactive Sexual Desire Disorder, premenstrual disorders like premenstrual dysphoria, premenstrual syndrome, premenstrual dysphoric disorder; sexual aversion disorder, sexual arousal disorder, orgasmic disorder, sexual pain disorders like dyspareunia, vaginismus, noncoital sexual pain disorder, sexual dysfunction due to a general medical condition and substance-induced sexual dysfunction), psychosis, schizophrenia (including the disorganized type, the catatonic type, the paranoid type, the undifferentiated type, the residual type of schizophrenia, schizoaffective disorder, schizophreniform disorder, delusional disorder, brief psychotic disorder, shared psychotic disorder, psychotic disorder due to a general medical condition, substance-induced psychotic disorder, and psychotic disorder not otherwise specified), personality disorders, mental organic disorders, mental disorders in childhood, aggressiveness, age associated memory impairment, for neuroprotection, the treatment and/or prevention of neurodegenerative diseases as well as cerebral ischaemia of various origins (e.g. epilepsy, hypoglycaemia, hypoxia, anoxia, brain trauma, brain oedema, amyotropic lateral sclerosis, Huntington's disease, Alzheimer's disease, hypotension, cardiac infarct, brain pressure (elevated intracranial pressure), ischaemic and haemorrhagic stroke (stroke), global cerebral ischaemia during stoppage of the heart, diabetic polyneuropathy, tinnitus, perinatal asphyxia, cardiac hypertrophia (thickening of the heart muscle) and cardiac insufficiency (weakness of the heart muscle), anorexia nervosa (incl. binge-eating/purging type of anorexia nervosa and the restricting type of anorexia nervosa). Attention Deficit Hyperactivity Disorder (ADHD) (incl. ADHD predominantly combined type, ADHD predominantly inattentive type, and ADHD predominantly hyperactive-impulsive type), obesity (incl. exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity), urinary inconhnence (incl. overactive bladder syndrome, urgency, urge urinary incontinence, stress urinary incontinence, mixed urinary incontinence) chronic pain (incl. neuropathic pain, diabetic neuropathy, post-herpetic neuralgia (PHN), carpal tunnel syndrome (CTS), HIV neuropathy, phantom limb pain, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain and geriatric pain), Valvular Heart Disease (incl. valvular stenosis, valvular regurgitation, atresia of one of the valves, mitral valve prolapse), insomnia (icluding primary and secondary insomnia), and vasomotor symptoms.

Preferably, salts and crystalline salt forms can be used for the treatment of disorders of sexual desire, more-preferably for HSDD (Hypoactive Sexual Desire Disorder).

The present invention also relates to pharmaceutical compositions comprising the above-mentioned salts or crystalline salt forms of the present invention.

The above salts and crystalline salt forms of the present invention, may be incorporated into the conventional pharmaceutical preparation in solid, liquid or spray form. The composition may, for example, be presented in a form suitable for oral, rectal, parenteral administration or for nasal inhalation: preferred forms includes for example, capsules, tablets, coated tablets, ampoules, suppositories and nasal spray.

The active ingredient may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic glicerides of fatty acids, benzalconium chloride, sodium phosphate, EDTA, polysorbate 80. The compositions are advantageously formulated in dosage units, each dosage unit besng adapted to supply a single dose of the active ingredient. The dosis range applicable per day is between 0.1 to 400, preferably between 1.0 to 300, more preferably between 2 to 200 mg.

Each dosage unit may conveniently contain from 0.01 mg to 100 mg, preferably from 0.1 to 50 mg.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example colidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g of, a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g of, with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

BRIEF DESCRIPTION OF THE FIGURES

FIG. 1.1a: X-ray powder diffraction diagram of HCl 1=chloride, form I;

FIG. 1.1b: X-ray powder diffraction diagram of HCl 3=chloride, form III;

FIG. 1.2a: X-ray powder diffraction diagram of HBr 1=hydrobromid, form I;

FIG. 1.2b: X-ray powder diffraction diagram of HBr 3=hydrobromid, form III;

FIG. 1.3: X-ray powder diffraction diagram of Eds 1=edisylate, form I;

FIG. 1.4: X-ray powder diffraction diagram of Tos 1=losylate, form I;

FIG. 1.5: X-ray powder diffraction diagram of Mes 1=mesylate, form I;

FIG. 1.6: X-ray powder diffraction diagram of Bes 1=besylate, form I;

FIG. 1.7a: X-ray powder diffraction diagram of Oxa 1=oxalate, form I;

FIG. 1.7b: X-ray powder diffraction diagram of Oxa 5=oxalate, form V;

FIG. 1.8: X-ray powder diffraction diagram of Sac 1=sacchannate, form I;

FIG. 1.9: X-ray powder diffraction diagram of Pho 1=phosphate, form I;

FIG. 1.10a: X-ray powder diffraction diagram of Mae 1=maleate, form I;

FIG. 1.10b: X-ray powder diffraction diagram of Mae 3=maleate, form III;

FIG. 1.11: X-ray powder diffraction diagram of Ets 1=ethanesulfonate, form I;

FIG. 1.12 X-ray powder diffraction diagram of Cas 1=camphorsulfonate, form I;

FIG. 1.13. X-ray powder diffraction diagram of Mao 1=matonate, form I;

FIG. 1.14: X-ray powder direction diagram of L-Tar 1=L-tartrate, form I;

FIG. 1.15a: X-ray powder diffraction diagram of Fum 1=fumarate, form I;

FIG. 1.15b: X-ray powder diffraction diagram of Fum 2=fumarate, form II;

FIG. 1.16 X-ray powder diffraction diagram of Gly 1=glycolate, form I;

FIG. 1.17: X-ray powder diffraction diagram of Cit 1=citrate, form I;

FIG. 1.18: X-ray powder diffraction diagram of Man 1=mandelate, form I;

FIG. 1.19: X-ray powder direction diagram of L-Mal 1=malate, form I;

FIG. 1.20 X-ray powder diffraction diagram of Nas 1=naphtalene-sulfonate, form I;

FIG. 1.21 X-ray powder diffraction diagram of TOS 2=tosylate, form II;

FIG. 1.22 X-ray powder diffraction diagram of Fum 3=fumarate, form III;

FIG. 1.23 X-ray powder diffraction diagram of Cas 2=camphorsulfonate, form II;

FIG. 1.24 X-ray powder diffraction diagram of Gly 3=glycolate, form II.

EXAMPLES

Analytical Methods for the Characterization of the Salts

The harvested crystals may be characterized by X-ray powder diffraction and thermal analysis (DSC). If suitable single crystals grow, single crystal X-ray structure analysis may be performed. The following equipment was used to characterize the crystalline salts forms.

X-ray Powder Diffraction (=XRPD)

XRPD patterns were obtained using a high throughput XRPD set-up. The plates were mounted on a Bruker GADDS dsffractometer equipped with a Hi-Star area detector. The diffractometer was calibrated using Silver Behenate for the long d-spacings and corundum for the short d-spacings.

The data collection was carried out at room temperature using monochromatic CuKα radiation in the region 2Θ between 1.5 and 41.5°. The diffraction pattern of eacn well was collected wth an exposure time of 3-4 minutes.

Single Crystal X-ray Structure Analysts

Suitable single crystals were selected and glued to a glass fibre, which is mounted on a X-ray diffraction goniometer. X-ray diffraction data were collected for the mounted crystals at a temperature of 233 K using a KappaCCD system and MoKα radiation generated by a FR590 X-ray generator (Bruker Nonius Delft, The Netherlands).

Unit-cell parameters and crystal structure were determined and refined using the software package maXus (Mackay et al., 1997).

Thermal Analysis (DSC)

Melting properties were obtained from differential scanning calorimetry (=DSC) thermograms recorded on a DSC822e (Mettler-Toledo GmbH, Switzerland). The DSC822e was calibrated for temperature and enthalpy with a small piece of indium ($T_{fus}$=156.6° C., $\Delta H_{fus}$=28.45 J/g). Samples were sealed in standard 40 μl aluminium pans and heated in the DSC from 25 to 300° C. with a heating rate of 20° C./min. Dry nitrogen gas was used to purge the DSC equipment during measurements at a flow rate of 50 ml/min. The melting temperature used was the $T_{fus}$ (onset) temperature of the corresponding melting peak tn the DSC diagram. The accuracy of the melting points specified is about ±5° C.

Hygroscopicity

IGAsorp water sorption monitor from Hiden Isochema was used for the analysis of the hygroscopical behaviour at room temperature.

humidity profile: from 10-90% r.h. in steps of 10%, sorption as well as desorption profiles were registered weight-in quantity: 10-20 mg Solubility Solubility of the different crystalline salt forms in water was determined by adding approx. 5 mg of compound into 5 ml of water at room temperature. The mixture was vigorously shaken for 2 hours at room temperature. Afterwards the undissolved solid was removed by filtering through a 0.45 μm PTFE filter, in the filtrate the dissolved amount of compound was determined by UV-spectroscopy.

Synthesis of the Salt Forms

The process is illustrated by the following example of manufacturing process of the salts and crystalline salt forms, as can be done in parallel in 96 well assay plates (maximum volume of each well is about 200 μl).

Approximately 1 g of the free base of flibanserin were dissolved in 10 ml TFE/water 80:20. The acids used to prepare the salts were dissolved in different solvents such that the molar ratio of the flibanserin to the respective acid was set according to the information given in Table 3 under "ratio base/acid". Fumaric acid was dissolved in THF/water 80:20. HCl in water and all other acids used were dissolved in TFE/water 80:20. However it is to mention that all other solvents which are able to dissolve the acid used could have been used. The 96 well plates were then placed in a vacuum chamber (1 kPa) at room temperature for 24 h in otder to evaporate the solvent. Afterwards, different solvents were added in each well according to the information given in Table 3 under "crystallization solvent", and the well plates were sealed and heated up to 50° C. at a heating rate of approx. 5° C./min. The plate stayed then for an additional 30 minutes at 50° C. Afterwards, the plate was cooled at a cooling rate of 5° C./h to a final temperature of 3 or 20° C. according to the information given in Table 3 under "$T_{final}$[° C.]". At this temperature, the plates remained for a holding time of 24 h. The plates were then opened and the solids were collected by filtration. All salts specified in table 3 were synthesized according to the above specification.

TABLE 3

Conditions for the preparation of the different salts of 1-[2-(4-(3-trifluoro-methyl-phenyl)piperazin-1-yl)ethyl]-2,3-dihydro-1H-benzimidazol-2-one

| salt form | salt form full name | used acid | ratio base/a | crystallization solvent | $T_{final}$ [° C.] |
|---|---|---|---|---|---|
| HCl | chloride, form I | hydrochloric acid | 1:1 | ethanol/water (80:20) | 3 |
| HCl3 | chloride, form III | hydrochloric acid | 1:1 | water/NMP* (80:20) | 20 |
| HBr 1 | bromide from I | hydrobromic acid | 1:1 | dichlormethane | 20 |
| HBr 3 | bromide from III | hydrobromic acid | 1:1 | methanol | 20 |
| Eds1 | edisylate form I | ethane-1,2 disulfonic acid | 1:1 | methanol | 20 |
| Tos 1 | tosylate form I | p-toluenesulfonic acid | 1:1 | THF* | 20 |
| Mes 1 | mesylate form I | methanesulfonic acid | 1:1 | TBME* | 20 |
| Bes 1 | besylate form I | benzenesulfonic acid | 1:1 | TBME* | 20 |
| Oxa 1 | oxalate form I | oxalic acid | 1:1 | 1,2 Dimethoxyethane | 20 |
| Oxa 5 | oxalate form V | oxalic acid | 1:1 | water/acetone (20:80) | 3 |
| Sac1 | sacharinate form I | sacharine | 1:1 | dichloromethane | 3 |
| Pho | phosphate form I | phsophoric acid | 1:1 | cyclohexanone | 20 |
| Mae1 | maleate form I | maleaic acid | 1:1 | THF* | 3 |
| Mae3 | maleate form III | maleaic acid | 1:1 | propyl acetate | 20 |
| Ets | ethanesulfonate | ethanesulfonic acid | 1:1 | 1,2 Dimethoxyethane | 20 |
| Cas1 | camphorsulfonate form I | campher-10 sulfonic acid | 1:1 | cyclohexane | 20 |
| Mao 1 | malonate form I | malonic acid | 1:1 | acetone/water (80:20) | 3 |
| Mao 2 | malonate form II | malonic acid | 1:1 | tert-Butanol | 3 |
| Mao 6 | malonic form VI | malonic acid | 1:1 | Nitromethane | 3 |
| Sal 1 | salicylate form I | salicylic acid | 1:1 | DMSO*/water (20:80) | 3 |
| L-Tart 1 | L-tartate form | L-tartaric acid | 1:1 | ethanol | 20 |
| Fum 1 | fumerate form I | fumaric acid | 2:1 | chloroform | 20 |
| Fum 2 | fumerate form II | fumaric acid | 2:1 | nitromethane | 20 |
| Gly 1 | glycolate form I | glycolic acid | 1:1 | TBME* | 20 |
| Cit1 | citrate form I | citric acid | 2:1 | ethanol/water (80:20) | 20 |
| Man 1 | mandelate form I | L-mandelic acid | 1:1 | ethanol | 20 |
| L-Mal 1 | L-malate form I | L-malic acid | 1:1 | ethanol | 3 |
| Suc 1 | succinate form I | succinic acid | 1:1 | $H_2O$ | 20 |
| Nas1 | naphtalene-sulfonate form I | naphtalene-2-sulfonic acid | 1:1 | 2-butanone | 3 |
| Tos 2 | tosylate form II (=anhydrous form) | p-toluenesulfonic acid | 1:1 | ethanol | 20 |
| Fum 3 | fumarate, form III (=anhydrous form) | fumaric acid | 1:1 | chloroform | 20 |
| Cas 2 | camphorsulfonate form II (=anhydrous form) | campher-10 sulfonic acid | 1:1 | ethanol | 20 |
| Gly 2 | glycolate form II (=hydrate form) | glycolic acid | 1:1 | TBME* | 20 |

*THF = tetrahydrofurane
*DMSO = dimethylsulfoxide
*NMP = 1-methyl-2-pyrrolidinone
*TBME = tert-butyl methyl ether
*TFE = 2,2,2,-Trifluoroethanol Examples of Formulations The Examples which follow illustrate the present invention without restricting its scope:

Examples of Pharmaceutical Formulations

| A) | Tablets | per tablet |
|---|---|---|
| | active substance | 100 mg |
| | lactose | 240 mg |
| | corn starch | 340 mg |
| | polyvinylpyrrolidone | 45 mg |
| | magnesium stearate | 15 mg |
| | | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | active substance | 5 mg |
| | corn starch | 41.5 mg |
| | lactose | 30 mg |
| | polyvinylpyrrolidone | 3 mg |
| | magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | active substance | 150 mg |
| | Corn starch | 268.5 mg |
| | Magnesium stearate | 1.5 mg |
| | | 420 mg |

The substance and corn starch are mixed ana moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion.

| F) | Suppositories | |
|---|---|---|
| | active substance | 50 mg |
| | solid fat | 1650 mg |
| | | 1700 mg |

The hard fat is melted. At 40° C. the ground active substance is homogeneously dispersed. It is cooled to 38° C. and poured into slightly chilled suppository moulds.

The invention claimed is:

1. A salt of the compound 1-[2-(4-(3-trifluoro-methyl-phenyl)piperazin-1-yl)ethyl]-2,3-dihydro-1H-benzimidazol-2-one selected from the group consisting of:
   I. crystalline 1-[2-(4-(3-trifluoro-methyl-phenyl)piperazin-1-yl)ethyl]-2,3-dihydro-1H-benzimidazol-2-one chloride having a melting point of $T_{fus}$ (onset)=215±5° C. and characteristic peaks in the x-ray powder diffractogram of d=15.99±0.05 Å, 7.44±0.05 Å, 3.98±0.05 Å, and 3.44±0.05 Å;
   II. crystalline 1-[2-(4-(3-trifluoro-methyl-phenyl)piperazin-1-yl)ethyl]-2,3-dihydro-1H-benzimidazol-2-one chloride having a melting point of $T_{fus}$ (onset)=217±5° C. and characteristic peaks in the x-ray powder diffractogram of d=16.43±0.05 Å, 5.08±0.05 Å, 4.35±0.05 Å, 3.47±0.05 Å, and 7.66±0.05 Å;
   III. crystalline 1-[2-(4-(3-trifluoro-methyl-phenyl)piperazin-1-yl)ethyl]-2,3-dihydro-1H-benzimidazol-2-one bromide having a melting point of $T_{fus}$ (onset)=252±5° C. and by the peaks in the X-ray powder diffractogram which occur at d=3.48±0.05 Å, d=3.33±0.05 Å, d=4.28±0.05 Å, d=3.43±0.05 Å and d=16.03±0.05 Å;
   IV. crystalline 1-[2-(4-(3-trifluoro-methyl-phenyl)piperazin-1-yl)ethyl]-2,3-dihydro-1H-benzimidazol-2-one bromide having a melting point of $T_{fus}$ (onset)=252±5° C. and by the peaks in the X-ray powder diffractogram which occur at d=15.52±0.05 Å, d=5.15±0.05 Å, d=4.60±0.05 Å, d=4.36±0.05 Å and d=3.94±0.05 Å;

V. crystalline 1-[2-(4-(3-trifluoro-methyl-phenyl)piperazin-1-yl)ethyl]-2,3-dihydro-1H-benzimidazol-2-one edisylate having a melting point of $T_{fus}$ (onset)=144±5° C.;

VI. crystalline 1-[2-(4-(3-trifluoro-methyl-phenyl)piperazin-1-yl)ethyl]-2,3-dihydro-1H-benzimidazol-2-one tosylate having a melting point of $T_{fus}$ (onset)=238±5° C.;

VII. crystalline 1-[2-(4-(3-trifluoro-methyl-phenyl)piperazin-1-yl)ethyl]-2,3-dihydro-1H-benzimidazol-2-one mesylate having a melting point of $T_{fus}$ (onset)=207±5° C.;

VIII. a crystalline 1-[2-(4-(3-trifluoro-methyl-phenyl)piperazin-1-yl)ethyl]-2,3-dihydro-1H-benzimidazol-2-one besylate having a melting point of $T_{fus}$ (onset)=247±5° C.;

IX. a crystalline 1-[2-(4-(3-trifluoro-methyl-phenyl)piperazin-1-yl)ethyl]-2,3-dihydro-1H-benzimidazol-2-one oxalate having a melting point of $T_{fus}$ (onset)=209±5° C.;

X. a crystalline 1-[2-(4-(3-trifluoro-methyl-phenyl)piperazin-1-yl)ethyl]-2,3-dihydro-1H-benzimidazol-2-one oxalate having a melting point of $T_{fus}$ (onset)=254±5° C.;

XI. crystalline 1-[2-(4-(3-trifluoro-methyl-phenyl)piperazin-1-yl)ethyl]-2,3-dihydro-1H-benzimidazol-2-one sacharinate having a melting point of $T_{fus}$ (onset)= 90±5° C.;

XII. a crystalline 1-[2-(4-(3-trifluoro-methyl-phenyl)piperazin-1-yl)ethyl]-2,3-dihydro-1H-benzimidazol-2-one phosphate having a melting point of $T_{fus}$ (onset)= 182±5° C.;

XIII a crystalline 1-[2-(4-(3-trifluoro-methyl-phenyl)piperazin-1-yl)ethyl]-2,3-dihydro-1H-benzimidazol-2-one maleate having a melting point of $T_{fus}$ (onset)=98±5° C.;

XIV. a crystalline 1-[2-(4-(3-trifluoro-methyl-phenyl)piperazin-1-yl)ethyl]-2,3-dihydro-1H-benzimidazol-2-one maleate having a melting point of $T_{fus}$ (onset)=172±5° C.;

XV. crystalline 1-[2-(4-(3-trifluoro-methyl-phenyl)piperazin-1-yl)ethyl]-2,3-dihydro-1H-benzimidazol-2-one ethansulfonate having a melting point of $T_{fus}$ (onset)= 207±5° C.;

XVI. crystalline 1-[2-(4-(3-trifluoro-methyl-phenyl)piperazin-1-yl)ethyl]-2,3-dihydro-1H-benzimidazol-2-one camphorsulfonate having a melting point of $T_{fus}$ (onset)= 217±5° C.;

XVII. crystalline 1-[2-(4-(3-trifluoro-methyl-phenyl)piperazin-1-yl)ethyl]-2,3-dihydro-1H-benzimidazol-2-one malonate having a melting point of $T_{fus}$ (onset)=103±5° C.;

XVIII. crystalline 1-[2-(4-(3-trifluoro-methyl-phenyl)piperazin-1-yl)ethyl]-2,3-dihydro-1H-benzimidazol-2-one malonate the following data:

| | |
|---|---|
| Empirical formula | $C_{20}H_{22}F_3N_4O^+ \cdot C_3H_3O_4^{-2} \cdot 2\, C_4H_{10}O$ |
| Fw | 642.71 |
| T [K] | 120(2) |
| λ [Å] | 0.71073 |
| Crystal system | Monoclinic |
| Space group | P 2₁/c |
| Unit cell dimensions | |
| a [Å] | 9.2650(3) |
| b [Å] | 24.2380(2) |
| c [Å] | 30.128(8) |
| α [°] | 90 |
| β [°] | 101.620(2) |
| γ [°] | 90 |
| V [Å³] | 6627.0(4) |
| Z | 8 |
| $D_m$ [g/cm³] | 1.288 |
| F(000) | 2736 |
| Crystal size [mm³] | 0.25 × 0.1 × 0.08 |
| θ range [°] | 1.5 → 24 |
| Reflections collected | 22364 |
| Independent reflections | 10286 [$R_{int}$ = 0.1143] |
| S | 1.093 |
| R [I > 2σ(I)] | R1 = 0.1070, wR2 = 0.1271 |
| R indices (all data) | R1 = 0.2167, wR2 = 0.1563 |

XIX. crystalline 1-[2-(4-(3-trifluoro-methyl-phenyl)piperazin-1-yl)ethyl]-2,3-dihydro-1H-benzimidazol-2-one malonate, having the following characteristics:

| | |
|---|---|
| Empirical formula | $C_{20}H_{22}F_3N_4O^+ \cdot C_3H_3O_4^{-2} \cdot H_2O$ |
| Fw | 530.50 |
| T [K] | 120(2) |
| λ [Å] | 0.71073 |
| Crystal system | Triclinic |
| Space group | P −1 |
| Unit cell dimensions | |
| a [Å] | 7.8050(2) |
| b [Å] | 8.0730(2) |
| c [Å] | 20.1470(4) |
| α [°] | 80.0090(8) |
| β [°] | 87.4660(8) |
| γ [°] | 74.5320(9) |
| V [Å³] | 1204.92(3) |
| Z | 2 |
| $D_m$ [g/cm³] | 1.462 |
| F(000) | 556 |
| Crystal size [mm³] | 0.3 × 0.25 × 0.1 |
| θ range [°] | 2 → 37 |
| Reflections collected | 14593 |
| Independent reflections | 12114 [$R_{int}$ = 0.0408] |
| S | 1.062 |
| R [I > 2σ(I)] | R1 = 0.0742, wR2 = 0.1389 |
| R indices (all data) | R1 = 0.1184, wR2 = 0.1594 |

XX. crystalline 1-[2-(4-(3-trifluoro-methyl-phenyl)piperazin-1-yl)ethyl]-2,3-dihydro-1H-benzimidazol-2-one salicylate the following data:

| | |
|---|---|
| Empirical formula | $C_{20}H_{22}F_3N_4O^+ \cdot C_7H_5O_3^-$ |
| Fw | 528.53 |
| T [K] | 293(2) |
| λ [Å] | 0.71073 |
| Crystal system | Monoclinic |
| Space group | P 2₁/c |
| Unit cell dimensions | |
| a [Å] | 16.3790(2) |
| b [Å] | 15.4410(4) |
| c [Å] | 10.1810(4) |
| α [°] | 90 |
| β [°] | 98.1820(12) |
| γ [°] | 90 |
| V [Å³] | 2548.6(2) |
| Z | 4 |
| $D_m$ [g/cm³] | 1.377 |
| F(000) | 1104 |
| Crystal size [mm³] | 0.4 × 0.3 × 0.2 |
| θ range [°] | 2.5 → 26 |
| Reflections collected | 12472 |
| Independent reflections | 4948 [$R_{int}$ = 0.0289] |
| S | 0.949 |

| | |
|---|---|
| R [I > 2σ(I)] | R1 = 0.0565, wR2 = 0.1471 |
| R indices (all data) | R1 = 0.0753, wR2 = 0.1647 |

XXI. crystalline 1-[2-(4-(3-trifluoro-methyl-phenyl)piperazin-1-yl)ethyl]-2,3-dihydro-1H-benzimidazol-2-one L-tartrate having a melting point of $T_{fus}$ (onset)=151±5° C.;

XXII. crystalline 1-[2-(4-(3-trifluoro-methyl-phenyl)piperazin-1-yl)ethyl]-2,3-dihydro-1H-benzimidazol-2-one hemifumarate having a melting point of $T_{fus}$ (onset)=195±5° C.;

XXIII. crystalline 1-[2-(4-(3-trifluoro-methyl-phenyl)piperazin-1-yl)ethyl]-2,3-dihydro-1H-benzimidazol-2-one fumarate having a melting point of $T_{fus}$ (onset)=193±5° C.;

XXIV. crystalline 1-[2-(4-(3-trifluoro-methyl-phenyl)piperazin-1-yl)ethyl]-2,3-dihydro-1H-benzimidazol-2-one glycolate (form I) (=hydrate form) having a melting point of $T_{fus}$ (onset)=139±5° C.;

XXV. crystalline 1-[2-(4-(3-trifluoro-methyl-phenyl)piperazin-1-yl)ethyl]-2,3-dihydro-1H-benzimidazol-2-one citrate having a melting point of $T_{fus}$ (onset)=176±5° C.;

XXVI. crystalline 1-[2-(4-(3-trifluoro-methyl-phenyl)piperazin-1-yl)ethyl]-2,3-dihydro-1H-benzimidazol-2-one mandelate having a melting point of $T_{fus}$ (onset)=148±5° C.;

XXVII. crystalline 1-[2-(4-(3-trifluoro-methyl-phenyl)piperazin-1-yl)ethyl]-2,3-dihydro-1H-benzimidazol-2-one L-malate having a melting point of $T_{fus}$ (onset)=176±5° C.;

XXVIII. crystalline 1-[2-(4-(3-trifluoro-methyl-phenyl)piperazin-1-yl)ethyl]-2,3-dihydro-1H-benzimidazol-2-one succinate the following data:

XXIX. crystalline 1-[2-(4-(3-trifluoro-methyl-phenyl)piperazin-1-yl)ethyl]-2,3-dihydro-1H-benzimidazol-2-one naphthalenesulfonate peaks in the X-ray powder diffractogram which occur at d=4.92±0.05 Å, d=3.43±0.05 Å, d=4.00±0.05 Å and d=3.96±0.05 Å;

| | |
|---|---|
| Empirical formula | 2 $C_{20}H_{22}F_3N_4O^+ \cdot C_4H_4O_4^{2-} \cdot$ 2 $H_2O$ |
| Fw | 934.94 |
| T [K] | 293(2) |
| λ [Å] | 0.71073 |
| Crystal system | Triclinic |
| Space group | P −1 |
| Unit cell dimensions | |
| a [Å] | 9.5450(4) |
| b [Å] | 10.7120(5) |
| c [Å] | 11.7330(7) |
| α [°] | 97.597(2) |
| β [°] | 93.690(2) |
| γ [°] | 110.663(3) |
| V [Å$^3$] | 1104.6(1) |
| Z | 1 |
| $D_m$ [g/cm$^3$] | 1.405 |
| F(000) | 490 |
| Crystal size [mm$^3$] | 0.3 × 0.3 × 0.2 |
| θ range [°] | 3.5 → 26 |
| Reflections collected | 6382 |
| Independent reflections | 4176 [$R_{int}$ = 0.0194] |
| S | 1.036 |
| R [I > 2σ(I)] | R1 = 0.0555, wR2 = 0.1386 |
| R indices (all data) | R1 = 0.0649, wR2 = 0.1484 |

XXX. crystalline 1-[2-(4-(3-trifluoro-methyl-phenyl)piperazin-1-yl)ethyl]-2,3-dihydro-1H-benzimidazol-2-one tosylate (form II) (=anhydrous form) having a melting point of $T_{fus}$ (onset)=241±5° C.;

XXXI. crystalline 1-[2-(4-(3-trifluoro-methyl-phenyl)piperazin-1-yl)ethyl]-2,3-dihydro-1H-benzimidazol-2-one fumarate (form III) (=anhydrous form) having a melting point of $T_{fus}$ (onset)=202±5° C.;

XXXII. crystalline 1-[2-(4-(3-trifluoro-methyl-phenyl)piperazin-1-yl)ethyl]-2,3-dihydro-1H-benzimidazol-2-one camphorsulfonate (form II) (=anhydrous form) having a melting point of $T_{fus}$ (onset)=231±5° C.;

XXXIII. crystalline 1-[2-(4-(3-trifluoro-methyl-phenyl)piperazin-1-yl)ethyl]-2,3-dihydro-1H-benzimidazol-2-one glycolate (form II) (=hydrate form) having a melting point of $T_{fus}$ (onset)=231±5° C.

2. A pharmaceutical composition comprising the crystalline salt forms according to claim 1 and a pharmaceutically acceptable excipient.

3. The salt of the compound of claim 1 wherein the crystalline 1-[2-(4-(3-trifluoro-methyl-phenyl)piperazin-1-yl)ethyl]ethyl]-2,3-dihydro-1H-benzimidazol-2-one chloride having a melting point of $T_{fus}$ (onset)=215±5° C. and characteristic peaks in the x-ray powder diffractogram of d=15.99±0.05 Å, 7.44±0.05 Å, 3.98±0.05 Å, and 3.44±0.05 Å is an anhydrous form.

4. The salt of the compound of claim 1 wherein the crystalline 1-[2-(4-(3-trifluoro-methyl-phenyl)piperazin-1-yl)ethyl]ethyl]-2,3-dihydro-1H-benzimidazol-2-one chloride having a melting point of $T_{fus}$ (onset)=217±5° C. and characteristic peaks in the x-ray powder diffractogram of d=16.43±0.05 Å, 5.08±0.05 Å, 4.35±0.05 Å, 3.47±0.05 Å, and 7.66±0.05 Å is a solvate.

5. The salt of the compound of claim 3 wherein the crystalline 1-[2-(4-(3-trifluoro-methyl-phenyl)piperazin-1-yl)ethyl]ethyl]-2,3-dihydro-1H-benzimidazol-2-one chloride having a melting point of $T_{fus}$ (onset)=215±5° C. and characteristic peaks in the x-ray powder diffractogram of d=15.99±0.05 Å, 7.44±0.05 Å, 3.98±0.05 Å, and 3.44±0.05 Å is crystallized from a mixture of water and ethanol.

6. The salt of the compound of claim 4 wherein the crystalline 1-[2-(4-(3-trifluoro-methyl-phenyl)piperazin-1-yl)ethyl]ethyl]-2,3-dihydro-1H-benzimidazol-2-one chloride having a melting point of $T_{fus}$ (onset)=217±5° C. and characteristic peaks in the x-ray powder diffractogram of d=16.43±0.05 Å, 5.08±0.05 Å, 4.35±0.05 Å, 3.47±0.05 Å, and 7.66±0.05 Å is crystallized from a mixture of water and 1-methyl-2-pyrrolidinone.

7. The salt of the compound of claim 1 wherein the crystalline 1-[2-(4-(3-trifluoro-methyl-phenyl)piperazin-1-yl)ethyl]ethyl]-2,3-dihydro-1H-benzimidazol-2-one chloride having a melting point of $T_{fus}$ (onset)=215±5° C. and characteristic peaks in the x-ray powder diffractogram of d=15.99±0.05 Å, 7.44±0.05 Å, 3.98±0.05 Å, and 3.44±0.05 Å is further characterized by having weakly endothermic signals at approximately 122° C. and 186° C.

8. The salt of the compound of claim 1 wherein the crystalline 1-[2-(4-(3-trifluoro-methyl-phenyl)piperazin-1-yl)ethyl]ethyl]-2,3-dihydro-1H-benzimidazol-2-one chloride having a melting point of $T_{fus}$ (onset)=217±5° C. and characteristic peaks in the x-ray powder diffractogram of d=16.43±0.05 Å, 5.08±0.05 Å, 4.35±0.05 Å, 3.47±0.05 Å, and 7.66±0.05 Å is further characterized by having weakly endothermic signals at approximately 56° C. and 121° C.

\* \* \* \* \*